US012454722B2

(12) United States Patent
Nygren

(10) Patent No.: US 12,454,722 B2
(45) **Date of Patent: *Oct. 28, 2025**

(54) MULTIPLEXED METHOD FOR THE IDENTIFICATION AND QUANTITATION OF MINOR ALLELES AND POLYMORPHISMS

(71) Applicant: Agena Bioscience, Inc., San Diego, CA (US)

(72) Inventor: Anders Olof Herman Nygren, San Diego, CA (US)

(73) Assignee: AGENA BIOSCIENCE, INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/142,512

(22) Filed: May 2, 2023

(65) Prior Publication Data

US 2023/0383340 A1 Nov. 30, 2023

Related U.S. Application Data

(63) Continuation of application No. 17/098,993, filed on Nov. 16, 2020, now Pat. No. 11,680,289, which is a continuation of application No. 16/669,311, filed on Oct. 30, 2019, now Pat. No. 10,865,439, which is a continuation of application No. 16/255,718, filed on Jan. 23, 2019, now Pat. No. 10,513,728, which is a continuation of application No. 15/136,024, filed on Apr. 22, 2016, now Pat. No. 10,233,489.

(60) Provisional application No. 62/280,951, filed on Jan. 20, 2016, provisional application No. 62/152,697, filed on Apr. 24, 2015.

(51) Int. Cl.
*C12Q 1/68* (2018.01)
*C12Q 1/6827* (2018.01)
*C12Q 1/6858* (2018.01)
*C12Q 1/686* (2018.01)

(52) U.S. Cl.
CPC ......... *C12Q 1/6858* (2013.01); *C12Q 1/6827* (2013.01); *C12Q 1/686* (2013.01)

(58) Field of Classification Search
CPC .................................................... C12Q 1/6858
See application file for complete search history.

(56) References Cited

U.S. PATENT DOCUMENTS

| | | | |
|---|---|---|---|
| 4,515,781 | A | 5/1985 | Torrence et al. |
| 4,582,789 | A | 4/1986 | Sheldon et al. |
| 4,683,195 | A | 7/1987 | Mullis et al. |
| 4,689,405 | A | 8/1987 | Frank et al. |
| 4,711,955 | A | 12/1987 | Ward et al. |
| 5,003,059 | A | 3/1991 | Brennan |
| 5,013,830 | A | 5/1991 | Ohtsuka et al. |
| 5,037,882 | A | 8/1991 | Steel |
| 5,059,654 | A | 10/1991 | Hou et al. |
| 5,064,754 | A | 11/1991 | Mills |
| 5,118,605 | A | 6/1992 | Urdea |
| 5,237,016 | A | 8/1993 | Ghosh et al. |
| 5,242,974 | A | 9/1993 | Holmes |
| 5,364,760 | A | 11/1994 | Chu et al. |
| 5,380,833 | A | 1/1995 | Urdea |
| 5,399,857 | A | 3/1995 | Doroshenko et al. |
| 5,412,083 | A | 5/1995 | Giese et al. |
| 5,480,784 | A | 1/1996 | Kacian et al. |
| 5,489,507 | A | 2/1996 | Chehab |
| 5,510,270 | A | 4/1996 | Fodor et al. |
| 5,512,439 | A | 4/1996 | Hornes et al. |

(Continued)

FOREIGN PATENT DOCUMENTS

| | | | |
|---|---|---|---|
| CN | 1670222 | A | 9/2005 |
| CN | 101194023 | A | 6/2008 |

(Continued)

OTHER PUBLICATIONS

Chinese Search Report issued in Chinese Patent Application No. 201680013462.4, mailed on Sep. 7, 2020, 2 pages of English Translation.
Ex Parte Quayle Action mailed on Apr. 20, 1999, in U.S. Appl. No. 08/617,256, filed Mar. 18, 1996.
Extended European Search Report mailed on Oct. 15, 2012, in European Patent Application No. 09826542.4, filed on Oct. 27, 2009, 8 pages.
Final Office Action mailed on Apr. 15, 1996, in U.S. Appl. No. 08/406,199, filed Mar. 17, 1995.
Final Office Action mailed on Apr. 19, 2005, in U.S. Appl. No. 09/686,148, filed Oct. 10, 2000, 6 pages.
Final Office Action mailed on Apr. 5, 1994, in U.S. Appl. No. 08/001,323, filed Jan. 7, 1993.

(Continued)

*Primary Examiner* — Kenneth R Horlick
(74) *Attorney, Agent, or Firm* — LOZA & LOZA, LLP

(57) ABSTRACT

Provided herein are products and processes for detecting the presence or absence of minor nucleic acid species in a sample containing a mixture of minor nucleic acid species and one or more major nucleic acid species, where the amount (frequency or copy number) of the minor nucleic acid species is less than that of the major nucleic acid species. Certain methods include amplifying the mixture and extending the resulting amplicons using chain terminating reagents and extension primers that specifically hybridize to the amplicons, where a chain terminating reagent specific for the major nucleic acid species has a concentration that is less than a chain terminating reagent that is specific for a minor nucleic acid species. Skewing the concentrations of the chain terminating reagents in favor of high concentrations of the chain terminating reagents specific for the minor nucleic acid species relative to a chain terminating reagent specific for a major nucleic acid species improves the detection limit (sensitivity) of detecting minor nucleic acid species present at low frequency or copy number in the mixture. In addition, the signals generated from the extension product of the major nucleic acid species amplicon can serve as a positive control and permit quantification of the minor nucleic acid species relative to the major nucleic acid species in the mixture.

21 Claims, 7 Drawing Sheets

(56) References Cited

U.S. PATENT DOCUMENTS

| | | | |
|---|---|---|---|
| 5,547,835 | A | 8/1996 | Koester |
| 5,605,798 | A | 2/1997 | Koester |
| 5,622,824 | A | 4/1997 | Koester |
| 5,650,489 | A | 7/1997 | Lam |
| 5,691,141 | A | 11/1997 | Koester |
| 5,700,642 | A | 12/1997 | Monforte et al. |
| 5,710,028 | A | 1/1998 | Eyal et al. |
| 5,770,272 | A | 6/1998 | Biemann et al. |
| 5,800,984 | A | 9/1998 | Vary |
| 5,851,765 | A | 12/1998 | Koester |
| 5,869,242 | A | 2/1999 | Kamb |
| 5,872,003 | A | 2/1999 | Koester |
| 5,885,775 | A | 3/1999 | Haff et al. |
| 5,888,819 | A | 3/1999 | Goelet et al. |
| 5,925,520 | A | 7/1999 | Tully et al. |
| 5,965,363 | A | 10/1999 | Monforte et al. |
| 5,976,798 | A | 11/1999 | Parker et al. |
| 5,989,871 | A | 11/1999 | Grossman et al. |
| 6,004,744 | A | 12/1999 | Goelet et al. |
| 6,043,031 | A | 3/2000 | Koester et al. |
| 6,074,823 | A | 6/2000 | Koester |
| 6,194,144 | B1 | 2/2001 | Koester |
| 6,197,498 | B1 | 3/2001 | Koester |
| 6,221,601 | B1 | 4/2001 | Koester et al. |
| 6,221,605 | B1 | 4/2001 | Koester |
| 6,225,450 | B1 | 5/2001 | Koester |
| 6,235,478 | B1 | 5/2001 | Koester |
| 6,238,871 | B1 | 5/2001 | Koester |
| 6,258,538 | B1 | 7/2001 | Koester et al. |
| 6,268,144 | B1 | 7/2001 | Koester |
| 6,277,573 | B1 | 8/2001 | Koester |
| 6,300,076 | B1 | 10/2001 | Koester |
| 6,428,955 | B1 | 8/2002 | Koester |
| 6,500,621 | B2 | 12/2002 | Koester |
| 6,602,662 | B1 | 8/2003 | Koester et al. |
| 6,613,509 | B1 | 9/2003 | Chen |
| 7,074,563 | B2 | 7/2006 | Koester |
| 7,108,974 | B2 | 9/2006 | Ecker et al. |
| 7,198,893 | B1 | 4/2007 | Koester et al. |
| 7,217,510 | B2 | 5/2007 | Ecker et al. |
| 7,226,739 | B2 | 6/2007 | Ecker et al. |
| 7,255,992 | B2 | 8/2007 | Ecker et al. |
| 7,419,787 | B2 | 9/2008 | Koester |
| 7,759,065 | B2 | 7/2010 | Koester |
| 8,003,317 | B2 | 8/2011 | Beaulieu et al. |
| 8,153,377 | B2 | 4/2012 | Cantor et al. |
| 8,349,566 | B2 | 1/2013 | Beaulieu et al. |
| 8,586,708 | B2 | 11/2013 | Ting et al. |
| 9,068,223 | B2 | 6/2015 | Beaulieu et al. |
| 9,896,724 | B2 | 2/2018 | Beaulieu et al. |
| 10,233,489 | B2 | 3/2019 | Nygren |
| 10,513,728 | B2 | 12/2019 | Nygren |
| 10,604,791 | B2 | 3/2020 | Honisch et al. |
| 10,640,817 | B2 | 5/2020 | Nygren |
| 10,865,439 | B2 | 12/2020 | Nygren |
| 11,111,530 | B2 | 9/2021 | Beaulieu et al. |
| 11,667,958 | B2 | 6/2023 | Honisch et al. |
| 11,680,289 | B2 | 6/2023 | Nygren |
| 2003/0022225 | A1 | 1/2003 | Monforte et al. |
| 2003/0027169 | A1 | 2/2003 | Zhang et al. |
| 2003/0119004 | A1 | 6/2003 | Wenz et al. |
| 2003/0203381 | A1 | 10/2003 | Kambara et al. |
| 2004/0259105 | A1 | 12/2004 | Fan et al. |
| 2005/0079521 | A1 | 4/2005 | Beaulieu et al. |
| 2005/0233381 | A1 | 10/2005 | Liu et al. |
| 2005/0287533 | A1 | 12/2005 | Ehrich et al. |
| 2005/0287592 | A1 | 12/2005 | Kless |
| 2006/0003352 | A1 | 1/2006 | Lipkin et al. |
| 2006/0166201 | A1 | 7/2006 | Schatz et al. |
| 2007/0202514 | A1 | 8/2007 | Koester et al. |
| 2007/0292861 | A1 | 12/2007 | Thompson |
| 2008/0167197 | A1 | 7/2008 | Schmidt et al. |
| 2008/0305479 | A1 | 12/2008 | Van Den et al. |
| 2011/0165133 | A1 | 7/2011 | Rabinovich et al. |
| 2012/0015826 | A1 | 1/2012 | Beaulieu et al. |
| 2012/0046178 | A1 | 2/2012 | Van Den et al. |
| 2012/0156685 | A1 | 6/2012 | Cantor et al. |
| 2013/0017960 | A1 | 1/2013 | Honisch et al. |
| 2013/0237428 | A1 | 9/2013 | Beaulieu et al. |
| 2014/0011195 | A1 | 1/2014 | Honisch et al. |
| 2016/0102347 | A1 | 4/2016 | Beaulieu et al. |
| 2016/0312278 | A1 | 10/2016 | Nygren |
| 2018/0298433 | A1 | 10/2018 | Nygren |
| 2019/0153526 | A1 | 5/2019 | Nygren |
| 2020/0123601 | A1 | 4/2020 | Nygren |
| 2020/0318169 | A1 | 10/2020 | Honisch et al. |
| 2021/0062254 | A1 | 3/2021 | Nygren |
| 2022/0106637 | A1 | 4/2022 | Beaulieu et al. |
| 2023/0407375 | A1 | 12/2023 | Honisch et al. |

FOREIGN PATENT DOCUMENTS

| | | | |
|---|---|---|---|
| CN | 103333952 | A | 10/2013 |
| CN | 103602740 | A | 4/2014 |
| CN | 103717751 | A | 4/2014 |
| CN | 103131787 | B | 5/2014 |
| CN | 104685064 | A | 6/2015 |
| EP | 0269520 | A2 | 6/1988 |
| EP | 0655501 | A1 | 5/1995 |
| EP | 1176212 | A1 | 1/2002 |
| JP | H07-159404 | A | 6/1995 |
| JP | H08-256764 | A | 10/1996 |
| JP | 2011-501008 | A | 1/1999 |
| JP | 2004-527732 | A | 9/2004 |
| JP | 2005-336107 | A | 12/2005 |
| JP | 2006-320271 | A | 11/2006 |
| JP | 2008-531052 | A | 8/2008 |
| JP | 2014-515264 | A | 6/2014 |
| WO | 89/10977 | A1 | 11/1989 |
| WO | 91/11533 | A1 | 8/1991 |
| WO | 92/13969 | A1 | 8/1992 |
| WO | 94/00562 | A1 | 1/1994 |
| WO | 94/16101 | A2 | 7/1994 |
| WO | 96/30545 | A1 | 10/1996 |
| WO | 96/32504 | A2 | 10/1996 |
| WO | 97/37041 | A2 | 10/1997 |
| WO | 03/104420 | A2 | 12/2003 |
| WO | 2004/007773 | A1 | 1/2004 |
| WO | 2005/012578 | A1 | 2/2005 |
| WO | 2006/133840 | A1 | 12/2006 |
| WO | 2010/054110 | A2 | 5/2010 |
| WO | 2010/056513 | A2 | 5/2010 |
| WO | 2011/034115 | A1 | 3/2011 |
| WO | 2012/159089 | A1 | 11/2012 |
| WO | 2014/018080 | A1 | 1/2014 |
| WO | 2016/172571 | A1 | 10/2016 |
| WO | 2016/172579 | A1 | 10/2016 |

OTHER PUBLICATIONS

Final Office Action mailed on Aug. 3, 2018, in U.S. Appl. No. 13/551,486, filed Jul. 17, 2012, 24 pages.

Final Office Action mailed on Aug. 22, 1995, in U.S. Appl. No. 08/178,216, filed Jan. 6, 1994.

Final Office Action mailed on Aug. 27, 2003, in U.S. Appl. No. 09/686,148, filed Oct. 10, 2000, 8 pages.

Final Office Action mailed on Dec. 26, 2001, in U.S. Appl. No. 09/179,536, filed Oct. 26, 1998.

Final Office Action mailed on Dec. 30, 2015, in U.S. Appl. No. 13/551,486, filed Jul. 17, 2012, 23 pages.

Final Office Action mailed on Feb. 26, 2014, in U.S. Appl. No. 13/551,486, filed Jul. 17, 2012, 30 pages.

Final Office Action mailed on Jan. 20, 2017, in U.S. Appl. No. 13/551,486, filed Jul. 17, 2012, 21 pages.

Final Office Action mailed on Jun. 15, 2017, in U.S. Appl. No. 13/551,486, filed Jul. 17, 2012, 19 pages.

Final Office Action mailed on Nov. 16, 2009, in U.S. Appl. No. 12/163,923, filed Jun. 27, 2008, 6 pages.

Final Office Action mailed on Sep. 7, 2021, in U.S. Appl. No. 16/793,732, filed Feb. 18, 2020, 31 pages.

Final Office Action mailed on Nov. 6, 1997, in U.S. Appl. No. 08/617,256, filed Mar. 18, 1996.

(56) References Cited

OTHER PUBLICATIONS

Non-Final Office Action mailed on Jun. 29, 1993, in U.S. Appl. No. 08/001,323, filed Jan. 7, 1993.
Non-Final Office Action mailed on Sep. 8, 2000, in U.S. Appl. No. 09/495,444, filed Jan. 31, 2000.
Non-Final Office Action mailed on May 27, 2022, in U.S. Appl. No. 16/793,732, filed Feb. 18, 2020, 31 pages.
Non-Final Office Action mailed on Apr. 10, 2014, in U.S. Appl. No. 13/126,684, filed Oct. 12, 2011, 18 pages.
Office Action mailed on Apr. 10, 2002, in U.S. Appl. No. 09/879,341, filed Jun. 11, 2001.
Office Action mailed on Apr. 28, 2020, in U.S. Appl. No. 16/669,311, filed Oct. 30, 2019, 5 pages.
Office Action mailed on Aug. 8, 2001, in U.S. Appl. No. 09/297,576, filed Jun. 28, 1999.
Office Action mailed on Aug. 17, 1998, in U.S. Appl. No. 08/744,481, filed Nov. 6, 1996.
Office Action mailed on Aug. 21, 2000, in U.S. Appl. No. 09/431,613, filed Nov. 2, 1999.
Office Action mailed on Aug. 26, 2022, in U.S. Appl. No. 17/098,993, filed Nov. 16, 2020, 5 pages.
Office Action mailed on Aug. 5, 2005, in U.S. Appl. No. 10/375,714, filed Feb. 24, 2003, 8 pages.
Office Action mailed on Dec. 19, 2001, in U.S. Appl. No. 09/796,416, filed Feb. 28, 2001.
Office Action mailed on Feb. 6, 2009, in U.S. Appl. No. 12/163,923, filed Jun. 27, 2008, 6 pages.
Office Action mailed on Feb. 16, 2000, in U.S. Appl. No. 09/287,682, filed Apr. 6, 1999.
Office Action mailed on Feb. 20, 2008, in U.S. Appl. No. 11/541,871, filed Oct. 2, 2006, 9 pages.
Office Action mailed on Feb. 23, 1995, in U.S. Appl. No. 08/178,216, filed Jan. 6, 1994.
Office Action mailed on Feb. 28, 2013, in U.S. Appl. No. 13/551,486, filed Jul. 17, 2012, 27 pages.
Office Action mailed on Jan. 9, 2018, in U.S. Appl. No. 13/551,486, filed Jul. 17, 2012, 19 pages.
Office Action mailed on Jan. 27, 2021, in U.S. Appl. No. 16/793,732, filed Feb. 18, 2020, 24 pages.
Office Action mailed on Jul. 6, 2000, in U.S. Appl. No. 09/179,536, filed Oct. 26, 1998.
Non-Final Office Action mailed on Jul. 8, 2015, in U.S. Appl. No. 13/551,486, filed Jul. 17, 2012, 23 pages.
Non-Final Office Action mailed on Jul. 25, 2002, in U.S. Appl. No. 09/179,536, filed Oct. 26, 1998.
Non-Final Office Action mailed on Jul. 3, 2007, in U.S. Appl. No. 11/432,171, filed May 11, 2006, 11 pages.
Non-Final Office Action mailed on Jun. 6, 2019, in U.S. Appl. No. 15/568,701, filed Oct. 23, 2017, 6 pages.
Non-Final Office Action mailed on Jun. 28, 2000, in U.S. Appl. No. 09/287,681, filed Apr. 6, 1999.
Non-Final Office Action mailed on Jun. 28, 2002, in U.S. Appl. No. 09/724,877, filed Nov. 28, 2000.
Non-Final Office Action mailed on Mar. 8, 2019, in U.S. Appl. No. 13/551,486, filed Jul. 17, 2012, 25 pages.
Non-Final Office Action mailed on Mar. 28, 2001, in U.S. Appl. No. 09/179,536, filed Oct. 26, 1998.
Non-Final Office Action mailed on May 5, 2000, in U.S. Appl. No. 09/287,679, filed Apr. 6, 1999.
Non-Final Office Action mailed on May 8, 2002, in U.S. Appl. No. 09/297,576, filed Jun. 28, 1999.
Non-Final Office Action mailed on May 11, 2009, in U.S. Appl. No. 12/125,857, filed May 22, 2008, 11 pages.
Non-Final Office Action mailed on May 13, 2019, in U.S. Appl. No. 16/255,718, filed Jan. 23, 2019, 5 pages.
Non-Final Office Action mailed on May 20, 2009, in U.S. Appl. No. 12/163,915, filed Jun. 27, 2008, 12 pages.
Non-Final Office Action mailed on May 29, 2018, in U.S. Appl. No. 15/136,024, filed Apr. 22, 2016, 6 pages.
Non-Final Office Action mailed on Nov. 3, 2010, in U.S. Appl. No. 12/795,155, filed Jun. 7, 2010, 11 pages.
Non-Final Office Action mailed on Nov. 20, 2002, in U.S. Appl. No. 09/686,148, filed Oct. 10, 2000, 9 pages.
Non-Final Office Action mailed on Oct. 4, 2016, in U.S. Appl. No. 13/551,486, filed Jul. 17, 2012, 16 pages.
Non-Final Office Action mailed on Sep. 5, 2013, in U.S. Appl. No. 13/551,486, filed Jul. 17, 2012, 26 pages.
Non-Final Office Action mailed on Sep. 8, 2000, in U.S. Appl. No. 09/504,245, filed Feb. 15, 2000.
Non-Final Office Action mailed on Sep. 14, 1995, in U.S. Appl. No. 08/406,199, filed Mar. 17, 1995.
Non-Final Office Action mailed on Sep. 22, 2000, in U.S. Appl. No. 09/287,679, filed Apr. 6, 1999.
Non-Final Office Action mailed on Feb. 16, 2000, in U.S. Appl. No. 09/287,141, filed Apr. 6, 1999.
Non-Final Office Action mailed on May 5, 1997, in U.S. Appl. No. 08/617,256, filed Mar. 18, 1996.
Notice of Allowance mailed on Apr. 1, 1999, in U.S. Appl. No. 08/744,481, filed Nov. 6, 1996.
Notice of Allowance mailed on Apr. 28, 2006, in U.S. Appl. No. 09/686,148, filed Oct. 10, 2000, 7 pages.
Notice of Allowance mailed on Aug. 2, 2019, in U.S. Appl. No. 16/255,718, filed Jan. 23, 2019, 6 pages.
Notice of Allowance mailed on Aug. 18, 2020, in U.S. Appl. No. 16/669,311, filed Oct. 30, 2019, 6 pages.
Notice of Allowance mailed on Dec. 9, 2019, in U.S. Appl. No. 13/551,486, filed Jul. 17, 2012, 10 pages.
Notice of Allowance mailed on Feb. 23, 2010, in U.S. Appl. No. 12/125,857, filed May 22, 2008, 10 pages.
Notice of Allowance mailed on Feb. 25, 2000, in U.S. Appl. No. 09/287,681, filed Apr. 6, 1999.
Notice of Allowance mailed on Feb. 25, 2008, in U.S. Appl. No. 11/432,171, filed May 11, 2006, 7 pages.
Notice of Allowance mailed on Feb. 3, 2023, in U.S. Appl. No. 17/098,993, filed Nov. 16, 2020, 6 pages.
Notice of Allowance mailed on Jan. 2, 2001, in U.S. Appl. No. 08/744,481, filed Nov. 6, 1996.
Notice of Allowance mailed on Jan. 3, 2020, in U.S. Appl. No. 15/568,701, filed Oct. 23, 2017, 7 pages.
Notice of Allowance mailed on Jan. 10, 2006, in U.S. Appl. No. 10/375,714, filed Feb. 24, 2003, 7 pages.
Notice of Allowance mailed on Jun. 14, 2000, in U.S. Appl. No. 09/287,682, filed Apr. 6, 1999.
Notice of Allowance mailed on May 17, 2002, in U.S. Appl. No. 09/796,416, filed Feb. 28, 2001.
Notice of Allowance mailed on Nov. 3, 2000, in U.S. Appl. No. 09/495,444, filed Jan. 31, 2000.
Notice of Allowance mailed on Nov. 16, 2000, in U.S. Appl. No. 09/287,679, filed Apr. 6, 1999.
Notice of Allowance mailed on Nov. 27, 2002, in U.S. Appl. No. 09/879,341, filed Jun. 11, 2001.
Notice of Allowance mailed on Oct. 8, 2008, in U.S. Appl. No. 11/541,871, filed Oct. 2, 2006, 5 pages.
Notice of Allowance mailed on Oct. 10, 2000, in U.S. Appl. No. 09/431,613, filed Nov. 2, 1999.
Notice of Allowance mailed on Oct. 20, 2000, in U.S. Appl. No. 09/504,245, filed Feb. 15, 2000.
Notice of Allowance mailed on Oct. 21, 1998, in U.S. Appl. No. 08/617,256, filed Mar. 18, 1996.
Notice of Allowance mailed on Oct. 22, 2018, in U.S. Appl. No. 15/136,024, filed Apr. 22, 2016, 5 pages.
Notice of Allowance mailed on Sep. 8, 2000, in U.S. Appl. No. 09/397,766, filed Sep. 15, 1999.
Notice of Allowance mailed on Sep. 10, 1999, in U.S. Appl. No. 08/617,256, filed Mar. 18, 1996.
Notice of Allowance mailed on Sep. 19, 2002, in U.S. Appl. No. 09/724,877, filed Nov. 28, 2000.
Notice of Allowance mailed on Feb. 3, 1998, in U.S. Appl. No. 08/617,256, filed Mar. 18, 1996.
Notice of Allowance mailed on May 30, 2000, in U.S. Appl. No. 09/287,141, filed Apr. 6, 1999.

(56) References Cited

OTHER PUBLICATIONS

Office Action mailed on Apr. 22, 2016, in U.S. Appl. No. 13/790,996, filed Mar. 8, 2013.
Office Action mailed on Aug. 1, 2003, in U.S. Appl. No. 08/467,208, filed Jun. 6, 1995.
Office Action mailed on Aug. 19, 1998, in U.S. Appl. No. 08/467,208, filed Jun. 6, 1995.
Office Action mailed on Aug. 22, 2019, in U.S. Appl. No. 13/126,684, filed Oct. 12, 2011, 23 pages.
Office Action mailed on Aug. 27, 2002, in U.S. Appl. No. 09/783,881, filed Feb. 13, 2001.
Office Action mailed on Dec. 16, 2016, in U.S. Appl. No. 13/790,996, filed Mar. 8, 2013.
Office Action mailed on Dec. 26, 2014, in U.S. Appl. No. 13/126,684, filed Oct. 12, 2011.
Office Action mailed on Feb. 7, 2019, in U.S. Appl. No. 13/790,996, filed Mar. 8, 2013.
Office Action mailed on Jan. 12, 1999, in U.S. Appl. No. 08/467,208, filed Jun. 6, 1995.
Office Action mailed on Jan. 17, 2017, in U.S. Appl. No. 13/126,684, filed Oct. 12, 2011.
Office Action mailed on Jan. 17, 2018, in U.S. Appl. No. 13/790,996, filed Mar. 8, 2013.
Office Action mailed on Jan. 29, 2016, in U.S. Appl. No. 13/126,684, filed Oct. 12, 2011.
Office Action mailed on Jan. 6, 2016, in U.S. Appl. No. 13/790,996, filed Mar. 8, 2013.
Office Action mailed on Jul. 16, 2001, in U.S. Appl. No. 08/467,208, filed Jun. 6, 1995.
Office Action mailed on Jul. 18, 2017, in U.S. Appl. No. 13/126,684, filed Oct. 12, 2011.
Office Action mailed on Jul. 29, 2002, in U.S. Appl. No. 08/467,208, filed Jun. 6, 1995.
Office Action mailed on Jul. 31, 2000, in U.S. Appl. No. 08/467,208, filed Jun. 6, 1995.
Office Action mailed on Jun. 19, 2015, in U.S. Appl. No. 13/790,996, filed Mar. 8, 2013.
Office Action mailed on Jun. 27, 2017, in U.S. Appl. No. 13/790,996, filed Mar. 8, 2013.
Office Action mailed on Jun. 28, 2018, in U.S. Appl. No. 13/126,684, filed Oct. 12, 2011.
Office Action mailed on Mar. 20, 1997, in U.S. Appl. No. 08/467,208, filed Jun. 6, 1995.
Office Action mailed on Mar. 26, 2001, in U.S. Appl. No. 08/467,208, filed Jun. 6, 1995.
Office Action mailed on Nov. 15, 2017, in U.S. Appl. No. 13/126,684, filed Oct. 12, 2011.
Office Action mailed on Nov. 16, 2018, in U.S. Appl. No. 13/126,684, filed Oct. 12, 2011.
Office Action mailed on Oct. 13, 1999, in U.S. Appl. No. 08/467,208, filed Jun. 6, 1995.
Office Action mailed on Oct. 28, 1997, in U.S. Appl. No. 08/467,208, filed Jun. 6, 1995.
Office Action mailed on Oct. 3, 2014, in U.S. Appl. No. 13/790,996, filed Mar. 8, 2013, 19 pages.
Office Action mailed on Oct. 3, 2016, in U.S. Appl. No. 13/126,684, filed Oct. 12, 2011.
Office Action mailed on Oct. 4, 2016, in U.S. Appl. No. 13/551,486, filed Jul. 17, 2012.
Office Action mailed on Sep. 8, 2005, in U.S. Appl. No. 08/467,208, filed Jun. 6, 1995.
Office Action mailed on Sep. 9, 2004, in U.S. Appl. No. 08/467,208, filed Jun. 6, 1995.
Office Action mailed on Sep. 8, 2014, in U.S. Appl. No. 13/099,236, filed May 2, 2011.
International Preliminary Report on Patentability mailed on May 12, 2011, in International Patent Application No. PCT/US2009/062239, filed on Oct. 27, 2009, 8 pages.
International Preliminary Report on Patentability mailed on Nov. 2, 2017, in International Patent Application No. PCT/US2016/028971, filed on Apr. 22, 2016, 10 pages.
International Preliminary Report on Patentability mailed on Nov. 2, 2017, in International Patent Application No. PCT/US2016/028980, filed on Apr. 22, 2016, 8 pages.
International Preliminary Report on Patentability mailed on Nov. 28, 2013, in International Patent Application No. PCT/US2012/038710, filed on May 18, 2012, 7 pages.
International Search Report and Written Opinion mailed on Jul. 9, 2010, in International Patent Application No. PCT/US2009/062239, filed on Oct. 27, 2009, 10 pages.
International Search Report and Written Opinion mailed on Jul. 15, 2016, in International Patent Application No. PCT/US2016/028971, filed on Apr. 22, 2016, 12 pages.
International Search Report and Written Opinion mailed on Jun. 22, 2016, in International Patent Application No. PCT/US2016/028980, filed on Apr. 22, 2016, 10 pages.
International Search Report and Written Opinion mailed on Sep. 5, 2012, in International Patent Application No. PCT/US2012/038710, filed on May 18, 2012, 10 pages.
Adler, et al., "Cell Membrane Coating with Glutaraldehyde: Application to a versatile Solid-Phase Assay for Thyroid Membrane Proteins and Molecules Interacting with Thyroid Membranes", Analytical Biochemistry, 1985, 148:320-327.
Anker, et al. "Tetranucleotide Repeat Polymorphism at the Human Thyroid Peroxidase (hTPO) Locus", Human Molecular Genetics, 1992, 1:137.
Banerjee, et al., "inhA, a Gene Encoding a Target for Isoniazid and Ethionamide in *MycoBacterium tuberculosis*", Science, Jan. 14, 1994, 263:227-230.
Beckmann, et al., "Survey of Human and Rat Microsatellites", Genomics, 1992, 12:627-631.
Binladen, et al., "The Use of Coded PCR Primers Enables High-Throughput Sequencing of Multiple Homolog Amplification Products by 454 Parallel Sequencing". Plos One, 2007, 2(2): e197:1-9.
Bird, Adrian, "DNA Methylation Patterns and Epigenetic Memory", Genes Development, 2002, 16:6-21.
Caruthers, et al., "Chemical Synthesis of Deoxyoligonucleotides by the Phosphoramidite Method", Methods in Enzymology, 1987, 154:287-313.
Caruthers, Marvin H., "Gene Synthesis Machines: DNA Chemistry and Its Use", Science, Oct. 18, 1985, 230:281-285.
Caskey, et al., "Triplet Repeat Mutations in Human Disease", Science, May 8, 1992, 256(5058):784-789.
Chakrabarti, et al., "Sequence of Simian Immunodeficiency Virus from Macaque and Its Relationship to Other Human and Simian Retroviruses", Nature, Aug. 6, 1987, 328:543-547.
Chee, M., "Enzymatic Multiples DNA Sequencing", Nucleic Acids Research, 1991, 19(12):3301-3305.
Cook, et al., "Synthesis and Hybridization of a Series of Biotinylated Oligonucleotides", Nucleic Acids Research, 1988, 16:4077-4095.
Deisingh, et al., "Sequences of *E. coli* O157:H7 detected by a PCR-acoustic wave sensor combination", Analyst, 2001, 126(12):2153-2158.
Ding, et al., "MS Analysis of Single-nucleotide Differences in Circulating Nucleic Acids: Application to Noninvasive Prenatal Diagnosis", PNAS, 2004, 101(29):10762-10767.
Ding, Chunming, "Qualitative and Quantitative DNA and RNA Analysis by Matrix-Assisted Laser Desorption/ionization Time-of-Flight Mass Spectrometry", Methods in Molecular Biology, 2006, 336:59-71.
Doktycz, et al., "Analysis of Polymerase Chain Reaction-Amplified DNA Products by Mass Spectrometry Using Matrix-Assisted Laser Desorption and Electrospray: Current Status", Analytical Biochemistry, 1995, 230:205-214.
Donovan, et al., "Increase in the Stability of Avidin Produced by Binding of Biotin. A Differential Scanning Calorimetric Study of Denaturation by Heat", Biochemistry, 1973, 12(3):512-517.
Dubiley, et al., "Polymorphism Analysis and Gene Detection by Minisequencing on an Array of Gel-Immobilized Primers", Nucleic Acids Research, 1999, 27(18):1-6.

(56) References Cited

OTHER PUBLICATIONS

Duffield, et al., "Simultaneous Determination of Multiple mRNA Levels Utilizing MALDI-TOF Mass Spectrometry and Biotinylated Dideoxynucleotides", RNA, Jun. 2010, 16(6):1285-1291.
Eckstein, "Oligonucleotides and Analogues: A Practical Approach", Oxford University Press, 1991, 56-57,137-139, 256-259.
Edwards, "Dinucleotide Repeat Polymorphism in Human GLUT2/ liver Facilitative Glucose Transporter Gene on Chromosome 3", Nucleic Acids Research, 1991, 19(17):4791.
Fan, et al., "Parallel Genotyping of Human Snps Using Generic High-Density Oligonucleotide Tag Arrays 11", Genome Research, Jan. 1, 2000, 10(6):853-860.
Fitzgerald, et al., "Basic Matrices for the Matrix-Assisted Laser Desorption/Ionization Mass Spectrometry of Proteins and Oligonucleotides", Analytical Chemistry, 1993, 65:3204-3211.
Ganem, et al., "Detection of Oligonucleotide Duplex Forms by lon-Spray Mass Spectrometry", Tetrahedron Letters, 1993, 34(9):1445-1448.
Gardner, et al., "Acyclic and Dideoxy Terminator Preferences Denote Divergent Sugar Recognition by Archaeon and Taq DNA Polymerases", Nucleic Acids Res., Jan. 15, 2002, 30(2):605-613.
German, et al., " Blood's Syndrome. XII. Report from the Registry for 1987", Clinical Genetics, 1989, 35:57-69.
Gust, et al., "Taxonomic Classification of Hepatitis a Virus", Intervirology, 1983, 20:1-7.
Guyader, et al., "Genome Organization and Transactivation of the Human Immunodeficiency Virus Type 2", Nature, Apr. 16, 1987, 326(6114):662-669.
Haff, et al., "Multiplex Genotyping of PCR Products with Mass Tag-Labeled Primers", Nucleic Acids Research, 1997, 25(18):3749-3750.
Haff, et al., "Single-Nucleotide Polymorphism Identification Assays Using a Thermostable DNA Polymerase and Delayed Extraction MALDI-TOF Mass Spectrometry", Genome Research, Apr. 1, 1997, 7(4):378-388.
Hartmer, et al., "RNase T1 Mediated Base-Specific Cleavage and MALDI-TOF MS for High-Throughput Comparative Sequence Analysis", Nucleic Acids Res., 2003, 31(9): e47:1-10.
Heym, et al., "Implications of Multidrug Resistance for the Future of Short-Course Chemotherapy of Tuberculosis: A Molecular Study", Lancet, 1994, 344(8918):293-298.
Hirsch, et al., "Easily Reversible Desthiobiotin Binding to Streptavidin, Avidin, and Other Biotin-Binding Proteins: Uses for Protein Labeling, Detection, and Isolation", Analytical Biochemistry, Sep. 2, 2015, 308(2):343-357.
Hirschhorn, et al., "SBE-TAGS: An Array-Based Method for Efficient Single-Nucleotide Polymorphism Genotyping 11", PNAS, Oct. 24, 2000, 97(22):12164-12169.
Hitchcock, et al., "Cleavage of Deoxyoxanosine-Containing Oligodeoxyribonucleotides by Bacterial Endonuclease V", Nucleic Acids Research, 2004, 32(13):4071-4080.
Holmberg, et al., "The Biotin-streptavidin Interaction can be Reversibly Broken Using Water at Elevated Temperatures", Electrophoresis, 2005, 26:501-510.
Jacobson, et al., "Applications of Mass Spectrometry to DNA Sequencing", Genet. Anal. Tech. Appl., 1991, 8(8):223-229.
Jeffreys, et al., "Hypervariable 'Minisatellite' Regions in Human DNA", Nature, Mar. 7, 1985, 314:67-73.
Khrapko, et al., "A Method for DNA Sequencing by Hybridization with Oligonucleotide Matrix", J. DNA Sequencing and Mapping, 1991, 1:375-388.
Kim, et al., "Digital Genotyping Using Molecular Affinity and Mass Spectrometry", Nature Review Genetics, 2003, 4:1001-1008.
Kim, et al., "Multiplex Genotyping of the Human Beta2-Adrenergic Receptor Gene Using Solid-Phase Capturable Dideoxynucleotides and Mass Spectrometry", Analytical Biochemistry, May 1, 2003, 316(2):251-258.
Kim, et al., "Solid Phase Capturable Dideoxynucleotides for Multiplex Genotyping Using Mass Spectrometry", Nucleic Acids Research, Aug. 15, 2002, 30(16): e85. (6 pages.).
Lefmann, et al., "Novel Mass Spectrometry-Based Tool for Genotypic Identification of Mycobacteria", Journal of Clinical Microbiology, Jan. 1, 2004, 42(1):339-346.
Leonard, et al., "High-Resolution Structure of Mutagenic Lesion in DNA", Proc. Nat. Acad. Sci. Biochemistry, 1990, 87:9573-9576.
Li, et al., "Single Nucleotide Polymorphism Determination Using Primer Extension and Time-of-flight Mass Spectrometry", Electrophoresis, Jun. 1999, 20(6):1258-1265.
Litt, et al., "Dinucleotide Repeat Polymorphism at the D11S35 Locus", Nucleic Acids Research, 1990, 18:5921.
Litt, et al., "Dinucleotide Repeat Polymorphism at the D6S89 Locus", Nucleic Acids Research, 1990, 18:4301.
Luty, et al., "Dinucleotide Repeat Polymorphism at the D14S45 Locus", Nucleic Acids Research, 1991, 19(15):4308.
Luty, et al., "Five Polymorphic Microsatellite VNTRs on the Human XChromosome", Am. J. Hum. Genet., 1990, 46:776-783.
Matthews, et al., "Analytical Strategies for the Use of DNA Probes", Analytical Chemistry, 1988, 169:1-25.
McKinnon, P.J., "Ataxia-Telangiectasia: An Inherited Disorder of Ionizing-Radiation Sensitivity in Man", Human Genetics, 1987, 75(3):197-208.
Mizusawa, et al., "Improvement of the Dideoxy Chain Termination Method of DNA Sequencing by Use of Deoxy-7-Deazaguanosine Triphosphate in Place of DGTP", Nucleic Acids Research, 1986, 14(3):1319-1325.
Morris, et al., "Molecular Mechanisms of Multiple Drug Resistance in Clinical Isolates of *Mycobacterium tuberculosis*", The Journal of Infectious Diseases, 1995, 171:954-960.
Morrison, et al., "Organic Chemistry", Published by Allyn and Bacon., Boston, Massachusetts, USA, 1973, 406-409.
Mosko, et al., "Ultrasensitive Detection of Multiplexed Somatic Mutations Using MALDI-TOF Mass Spectrometry", The Journal of Molecular Diagnostics, 2016, 18:23-31.
Muddiman, et al., "Length and Base Composition of PCR-Amplified Nucleic Acids Using Mass Measurements from Electrospray Ionization Mass Spectrometry", Analytical Chemistry, Apr. 15, 1997, 69(8):1543-1549.
Mullis, "The Unusual Origin of the Polymerase Chain Reaction", Scientific American, 1990, 262(4):56-61.
Naito, et al., "Molecular Mass Measurement of Polymerase Chain Reaction Products Amplified from Human Blood DNA by Electrospray Ionization Mass Spectrometry", Rapid Communications in Mass Spectrometry, 1995, 9:1484-1486.
Nakamura, et al., "Variable Number of Tandem Repeat (VNTR) Markers for Human Gene Mapping", Science, 1987, 235:1616-1622.
Naomi, et al., "Rapid Mass Spectrometric Identification of Human Genomic Polymorphisms Using Multiplexed Photocleavable Mass-Tagged Probes and Solid Phase Capture", Organic and Biomolecular Chemistry, Jan. 1, 2007, 5(12):1878-1885.
Nguyen, et al., "Mild Conditions for Releasing Mono and Bis-Biotinylated Macromolecules from Immobilized Streptavidin", Biomolecular Engineering, Oct. 1, 2005, 22(4):147-150.
Nishimura, et al., "A Tetranucleotide Repeat for The F13B Locus", Nucleic Acids Research, 1992, 20(5):1167.
Nordhoff, et al., "Matrix-assisted Laser Desorption/Ionization Mass Spectrometry of Nucleic Acids with Wavelengths in the Ultraviolet and Infrared", Rapid Communications in Mass Spectrometry, Dec. 1992, 6(12):771-776.
Oeth, et al., "SEQUENOM® Application Note, Document No. 8876-006, R04", Nov. 10, 2006, 12 pages.
Overberg, et al., "Matrix-Assisted Laser Desorption of Large Biomolecules with a TEA-CO.sub.2-Laser", Rapid Communications in Mass Spectrometry, 1991, 5(3):128-131.
Palejwala, et al., "Quantitative Multiplex Sequence Analysis of Mutational Hot Spots. Frequency and Specificity of Mutations Induced by a Site-Specific Ethenocytosine in M13 Viral DNA", Biochemistry, 1993, 32:4105-4111.
Pieles, et al., "Matrix-assisted Laser Desorption Ionization Time-of-flight Mass Spectrometry: A Powerful Tool for The Mass and Sequence Analysis of Natural and Modified Oligonucleotides", Nucleic Acid Research, 1993, 21(14):3191-3196.

(56) References Cited

OTHER PUBLICATIONS

Pierce, et al., "Comparison of the GenMark Diagnostics eSensor Respiratory Viral Panel to Real-Time PCR for Detection of Respiratory Viruses in Children", Journal of Clinical Microbiology, Nov. 2012, 50(11):3458-3465.
Ploos, et al., "Tetranucleotide Repeat Polymorphism in the VWF Gene", Nucleic Acids Research, 1990, 18(16):4957.
Polymeropoulos, et al., "Trinucleotide Repeat Polymorphism at the Human Pancreatic Phospholipase A-2 Gene (PLA2)", Nucleic Acids Research, 1990, 18(24):7468.
Polymeropoulos, et al., "Tetranucleotide Repeat Polymorphism at the Human C- Fes/fps Proto-Oncogene (FES)", Nucleic Acids Research, 1991, 19(14):4018.
Polymeropoulos, et al., "Tetranucleotide Repeat Polymorphism at the Human Aromatase Cytochrome p. 450 Gene (CYP19)", Nucleic Acids Research, 1991, 19(1):195.
Polymeropoulos, et al., "Tetranucleotide Repeat Polymorphism at the Human Coagulation Factor XIII a Subunit Gene(F13A1)", Nucleic Acids Research, 1991, 19(15):4306.
Ratner, et al., "Complete Nucleotide Sequence of AIDS Virus, HTLV-III", Nature, 1985, 313:227-284.
Reymer, et al., "A Lipoprotein Lipase Mutation (Asn291Ser) Is Associated with Reduced HDL Cholesterol Levels in Premature Atherosclerosis", Nature Genetics, 1995, 10(1):28-34.
Rosli, et al., "Quantitative Recovery of Biotinylated Proteins from Streptavidin-Based Affinity Chromatography Resins", Methods in Molecular Biology, 2008, 418:89-100.
Rybak, et al., "Purification of Biotinylated Proteins on Streptavidin Resin: A Protocol for Quantitative Elution", Proteomics, 2004, 4(8):2296-2299.
Sano, et al., "Intersubunit Contacts Made by Tryptophan 120 with Biotin Are Essential for Both Strong Biotin Binding and Biotin-Induced Tighter Subunit Association of Streptavidin", PNAS, 1995, 92(8):3180-3184.
Schächter, et al., "Genetic Associations with Human Longevity at the APOE and ACE loci", Nature Genetics, 1994, 6:29-32.
Schlesinger, "Macromolecular Sequencing and Synthesis: Selected Methods and Applications", Alan R. Liss, Inc., New York, 1988, 127-149.
Singer-Sam, "A Sensitive, Quantitative Assay for Measurement of Allele-specific Transcripts Differing by a Single Nucleotide", Genome Research, 1992, 1:160-163.
Si-Yuan, et al., "Principal and Development of SNP Genotyping Technology", Letters in Biotechnology, English Abstract Only, May 2003, 14(3):218-221.
Smith, et al., "Immobilization of Nucleic Acids Using Biotin-Strept(avidin) Systems", Topics in Current Chemistry, 2005, 261:63-90.
Stahl, et al., "Solid Phase DNA Sequencing Using the Biotin-Avidin System", Nucleic Acids Research, 1988, 16(7):3025-3039.
Stanssens, et al., "High-Throughput MALDI-TOF Discovery of Genomic Sequence Polymorphisms", Genome Research, 2004, 14(1):126-133.
Takenaka, et al., "Multiplex Single-Base 1-39 Extension Typing to Identify Nuclear Genes Required for RNA Editing in Plant Organelles", Nucleic Acid Research, Dec. 5, 2008, 37(2): e13.
Tautz, et al., "Hypervariability of Simple Sequences as a General Source for Polymorphic DNA Markers", Nucleic Acids Research, 1989, 17(16):6463-6471.
Thompson, et al., " Electrospray Ionisation-Cleavable Tandem Nucleic Acid Mass Tag-Peptide Nucleic Acid Conjugates: Synthesis and Applications to Quantitative Genomic Analysis Using Electrospray Ionisation-MS/MS ", Nucleic Acid Research, Jan. 26, 2007, 35(4): e28 1-13.
Tost, et al., "Genotyping Single Nucleotide Polymorphisms by Mass Spectrometry", Mass Spectrometry Reviews, 2002, 21(6):388-418.
Trainor, "Dna Sequencing, Automation, and the Human Genome", Anal. Chem., 1990, 62:418-426.
Tsang, et al., "Mass Spectrometry-Based Detection of Hemoglobin E Mutation by Allele-Specific Base Extension Reaction", Clinical Chemistry, 2007, 53(12):2205-2209.
Tuschihashi, et al., "Progress in High Throughput SNP Genotyping Methods", The Pharmacogenomics Journal, Jan. 1, 2002, 2(2):103-110.
Uhlmann, et al., "Antisense Oligonucleotides: A New Therapeutic Principle, Chemical Reviews", Chemical Reviews, 1990, 90(4):544-583.
Vallone, et al., "Genotyping SNPs Using a UV-Photocleavable Oligonucleotide in MALDI-TOF Mvallon", Methods in Molecular Biology, 2005, 297:169-178.
Vivante, et al., "High-Throughput, Sensitive and Quantitative Assay for the Detection of BCR-ABL Kinase Domain Mutations", Leukemia, 2007, 21(6):1318-1321.
Wain, et al., "Nucleotide Sequence of the AIDS Virus, LAV", Cell, 1985, 40(1):9-17.
Wang, et al., "Large-Scale Identification, Mapping, and Genotyping of Single-Nucleotide Polymorphisms in the Human Genome", Science, 1998, 280(5366): 1077-1082.
Weber, et al., "Abundant Class of Human DNA Polymorphisms Which Can Be Typed Using the Polymerase Chain Reaction", American Journal of Human Genetics, 1989, 44(3):388-396.
Weissenbach, et al., "A Second-Generation Linkage Map of the Human Genome", Nature, 1992, 359(6398):794-801.
Wenzel, et al., "Genosnip: SNP Genotyping by MALDI-TOF MS Using Photocleavable Oligonucleotides", Nucleosides, nucleotides nucleic acids, 2003, 22(5-8):1579-1581.
Wu, et al., "Matrix-Assisted Laser Desorption Time-of-Flight Mass Spectrometry of Oligonucleotides Using 3-Hydroxypicolinic Acid as an Ultraviolet-Sensitive Matrix", Rapid Communications in Mass Spectrometry, 1993, 7(2):142-146.
Wunschel, et al., "Analysis of Double-Stranded Polymerase Chain Reaction Products from the Bacillus Cereus Group by Electrospray Ionization Fourier Transform lon Cyclotron Resonance Mass Spectrometry", Rapid Communications in Mass Spectrometry, 1996, 10(1):29-35.
Yao, et al., "Interaction of Deoxyinosine 3'-Endonuclease from *Escherichia coli* with DNA Containing Deoxyinosine", Journal of Biological Chemistry, 1995, 270(48):28609-28616.
Yao, et al., "Purification and Characterization of a Novel Deoxyinosine-Specific Enzyme, Deoxyinosine 3' Endonuclease, from *Escherichia coli*", Journal of Biological Chemistry, 1994, 269(23):16260-16268.
Yao, et al., "Strand-Specific Cleavage of Mismatch-Containing DNA by Deoxyinosine 3'- Endonuclease from *Escherichia coli*", Journal of Biological Chemistry, 1994, 269(50):31390-31396.
Ying, et al., "Design of a Reversible Biotin Analog and Applications in Protein Labeling, Detection, and Isolation", Chemical Communications, 2011, 47:8593-8595.
Yolov, et al., "Synthesis of RNA Using T7 Rna Polymerase and Immobilized DNA in a Stream Type Reactor", Biooraanicheskala Khhimia, Jun. 1991, 17(6):789-794.
Zuliani, et al., "Tetranucleotide Repeat Polymorphism in the LPL Gene", Nucleic Acids Research, 1990, 18(16):4958.
Office Action mailed on Jan. 9, 2001, in U.S. Appl. No. 09/431,613, filed Nov. 2, 1999.
Office Action mailed on May 8, 2002, in U.S. Appl. No. 09/783,881, filed Feb. 13, 2001.
Hammond et al., "Rapid Mass Spectrometric Identification of Human Genomic Polymorphisms Using Multiplexed Photocleavable Mass-Tagged Probes and Solid Phase Capture", Organic & Biomolecular Chemistry, May 10, 2007, pp. 1878-1885.
Mengel-Jergensen et al., "Typing of Multiple Single-Nucleotide Polymorphisms Using Ribonuclease Cleavage of DNA/RNA Chimeric Single-Base Extension Primers and Detection by MALDI-TOF Mass Spectrometry", Analytical Chemistry, vol. 77, No. 16, Aug. 15, 2005, pp. 5229-5235.
Sanchez et al., "Typing of Y Chromosome SNPs with Multiplex PCT Methods", Methods in Molecular Biology, vol. 297, Dec. 31, 2005, pp. 209-228.
Office Action in co-pending U.S. Appl. No. 18/139,303, dated Dec. 13, 2024, 18 pages.

(56) References Cited

OTHER PUBLICATIONS

Final Office Action in co-pending U.S. Appl. No. 18/139,303, dated Apr. 22, 2024, 15 pages.

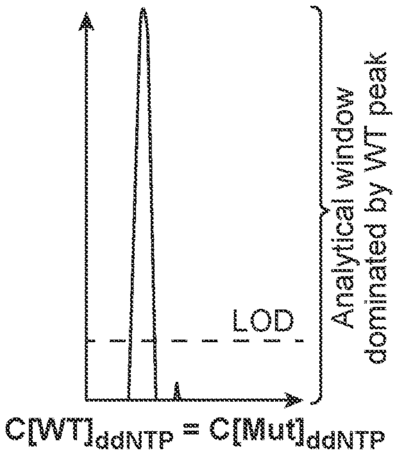
FIG. 1A
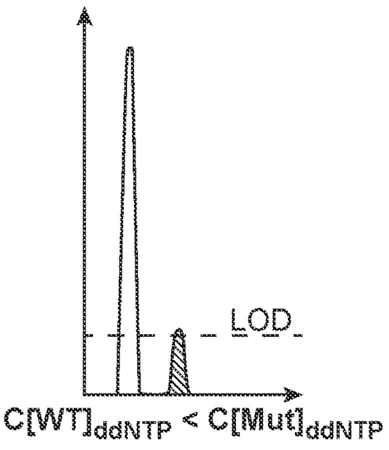
FIG. 1B
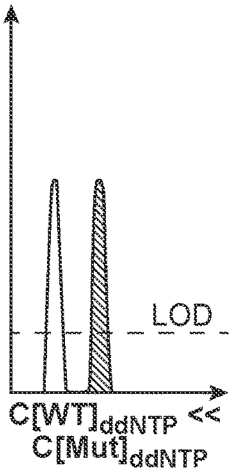
FIG. 1C
FIG. 2A
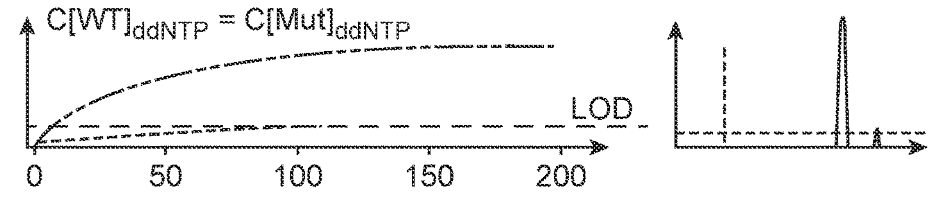
FIG. 2B
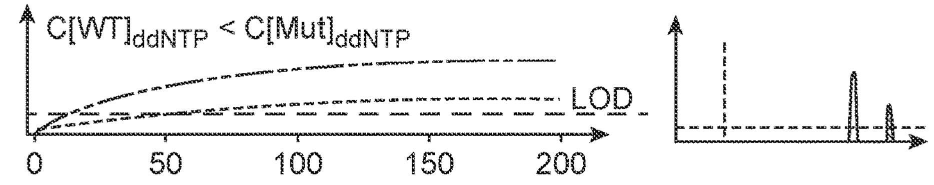
FIG. 2C
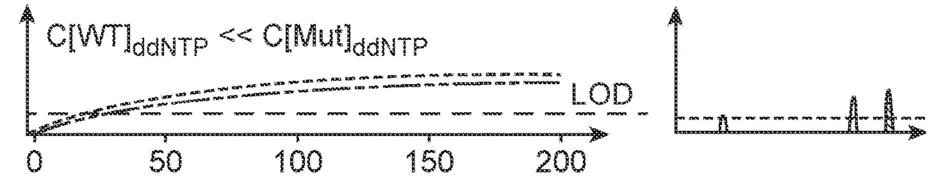
FIG. 2D
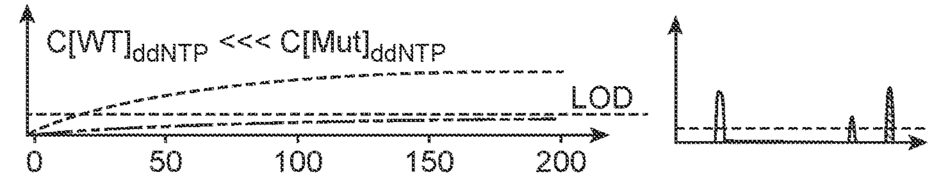

MULTIPLEXED METHOD FOR THE IDENTIFICATION AND QUANTITATION OF MINOR ALLELES AND POLYMORPHISMS

RELATED APPLICATIONS

This patent application is a continuation of U.S. patent application Ser. No. 17/098,993 filed on Nov. 16, 2020, now U.S. Pat. No. 11,680,289, naming Anders Olof Herman Nygren as inventor, entitled MULTIPLEXED METHOD FOR THE IDENTIFICATION AND QUANTITATION OF MINOR ALLELES AND POLYMORPHISMS, and, which is a continuation of U.S. patent application Ser. No. 16/669,311 filed on Oct. 30, 2019, now U.S. Pat. No. 10,865,439, naming Anders Olof Herman Nygren as inventor, entitled MULTIPLEXED METHOD FOR THE IDENTIFICATION AND QUANTITATION OF MINOR ALLELES AND POLYMORPHISMS, and, which is a continuation of U.S. patent application Ser. No. 16/255,718 filed on Jan. 23, 2019, now U.S. Pat. No. 10,513,728, naming Anders Olof Herman Nygren as inventor, entitled MULTIPLEXED METHOD FOR THE IDENTIFICATION AND QUANTITATION OF MINOR ALLELES AND POLYMORPHISMS, and, which is a continuation of U.S. patent application Ser. No. 15/136,024 filed on Apr. 22, 2016, now U.S. Pat. No. 10,233,489, naming Anders Olof Herman Nygren as inventor, entitled MULTIPLEXED METHOD FOR THE IDENTIFICATION AND QUANTITATION OF MINOR ALLELES AND POLYMORPHISMS, and, which claims the benefit of U.S. Provisional Patent Application No. 62/280,951, filed Jan. 20, 2016, entitled MULTIPLEXED METHOD FOR THE IDENTIFICATION AND QUANTITATION OF MINOR ALLELES AND POLYMORPHISMS, naming Anders Olof Herman Nygren as inventor and U.S. patent application Ser. No. 15/136,024 filed on Apr. 22, 2016, naming Anders Olof Herman Nygren as inventor, entitled MULTIPLEXED METHOD FOR THE IDENTIFICATION AND QUANTITATION OF MINOR ALLELES AND POLYMORPHISMS, and also claims the benefit of U.S. Provisional Application No. 62/152,697, filed Apr. 24, 2015, entitled MULTIPLEXED METHOD FOR THE IDENTIFICATION AND QUANTITATION OF MINOR ALLELES AND POLYMORPHISMS, naming Anders Olof Herman Nygren as inventor and U.S. patent application Ser. No. 15/136,024 filed on Apr. 22, 2016, naming Anders Olof Herman Nygren as inventor, entitled MULTIPLEXED METHOD FOR THE IDENTIFICATION AND QUANTITATION OF MINOR ALLELES AND POLYMORPHISMS, and is related to U.S. patent application Ser. No. 13/718,758, filed Dec. 18, 2012, now U.S. Pat. No. 9,068,223, naming Martin Beaulieu and Dirk Johannes van den Boom as inventors, entitled METHODS FOR HIGH LEVEL MULTIPLEXED POLYMERASE CHAIN REACTIONS AND HOMOGENEOUS MASS EXTENSION REACTIONS, which is a continuation of U.S. patent application Ser. No. 13/193,390, filed Jul. 28, 2011, now U.S. Pat. No. 8,349,566, naming Martin Beaulieu and Dirk Johannes van den Boom as inventors, entitled METHODS FOR HIGH LEVEL MULTIPLEXED POLYMERASE CHAIN REACTIONS AND HOMOGENEOUS MASS EXTENSION REACTIONS, which is a continuation of U.S. patent application Ser. No. 10/903,268, filed Jul. 30, 2004, now U.S. Pat. No. 8,003,317, naming Martin Beaulieu and Dirk Johannes van den Boom as inventors, entitled METHODS FOR HIGH LEVEL MULTIPLEXED POLYMERASE CHAIN REACTIONS AND HOMOGENEOUS MASS EXTENSION REACTIONS, of which benefit of priority under 35 U.S.C. § 119 (e) is claimed to U.S. provisional application Ser. No. 60/492,102, filed Jul. 31, 2003, to Martin Beaulieu and Dirk van den Boom, entitled "METHODS FOR HIGH LEVEL MULTIPLEXED POLYMERASE CHAIN REACTIONS AND HOMOGENEOUS MASS EXTENSION REACTIONS," U.S. patent application Ser. No. 15/136,024 filed on Apr. 22, 2016, naming Anders Olof Herman Nygren as inventor, entitled MULTIPLEXED METHOD FOR THE IDENTIFICATION AND QUANTITATION OF MINOR ALLELES AND POLYMORPHISMS, and also is related to International PCT Application No. PCT/US2004/024953, filed Dec. 18, 2012, entitled "METHODS FOR HIGH LEVEL MULTIPLEXED POLYMERASE CHAIN REACTIONS AND HOMOGENEOUS MASS EXTENSION REACTIONS," naming Martin Beaulieu and Dirk van den Boom as inventors. The subject matter of each of these applications is incorporated in its entirety by reference thereto, including texts, tables and drawings.

FIELD

The technology relates in part to identifying and/or quantitating nucleic acid variants, e.g., polymorphisms or mutant variants of a wild type allele.

BACKGROUND

The detection of specific nucleic acids is an important tool for diagnostic medicine and molecular biology research. Nucleic acid assays can, for example, identify infectious organisms such as bacteria and viruses in host subjects, probe the expression of normal genes and identify mutant genes such as oncogenes, type tissue for compatibility prior to tissue transplantation, match tissue or blood samples for forensic medicine, analyze homology among genes from different species and identify polymorphisms and alleles that are variants of a gene. These applications often require the ability to detect and/or quantify relatively small amounts of a minor nucleic acid species of interest (e.g., minor allelic variant of a wild-type allele, or an oncogene) that is present in a nucleic acid sample or mixture that contains relatively large amounts of a non-target (major) nucleic acid species. This ability is further enhanced (in efficiency, for example) if the nucleic acid assays can be performed in a multiplexed manner, i.e., a plurality of nucleic acids are screened.

Previous methods, including multiplexed methods, of detecting low frequency (copy number) variants among alleles, polymorphisms or other mutations, while often reliable and reproducible, have a detection sensitivity or limit that is less than what might be needed to identify the low frequency variants (e.g., a detection limit of about 10%-15% frequency will fail to identify mutation frequencies that are lower than that range). Relatively low detection limits generally are due to the low frequency variant detection signal being overshadowed by the larger detection signal of the predominant wild type species. Other methods overcome this problem by removing the "wild type" signal, thereby improving the detection of low frequency variants. Removing the wild type signal, however, can lead to difficulty in quantitating the relative amount of variant in a nucleic acid sample, or in unequivocally confirming the absence of a low frequency variant. Methods, including multiplexed methods, which combine high detection sensitivity with high accuracy, can provide improved identification and/or quantitation of certain low frequency variants that are undetected or are not optimally detected by the previous methods.

SUMMARY

Provided herein are methods, including multiplexed methods, which combine high detection sensitivity with high accuracy, providing improved identification and/or quantification of certain low frequency variants that would otherwise be undetected or not optimally detected or quantified.

In certain embodiments, provided herein is a multiplexed method for identifying the presence or absence of one or more minor nucleic acid species in a nucleic acid population that includes a mixture of the one or more minor nucleic acid species and one or more major nucleic acid species, where each minor nucleic acid species is a variant of a corresponding major nucleic acid species and is present in a copy number that is less than the copy number of its corresponding major nucleic acid species, where the method includes:

(a) simultaneously amplifying target regions of the mixture with amplification primer pairs under amplification conditions that include dNTPs, whereby an amplified mixture of nucleic acids comprising major and minor nucleic acid species is produced;

(b) contacting the amplified mixture with extension primers under extension conditions that include chain terminating reagents, where:

(i) the one or more major nucleic acid species share a common chain terminating reagent that is specific for the major nucleic acid species and is not specific for the minor nucleic acid species, and (ii) each of the one or more minor nucleic acid species has a chain terminating reagent that is specific for the minor nucleic acid species and is not specific for the major nucleic acid species, where the chain terminating reagent that is specific for the minor nucleic acid species either: (A) is unique for a particular minor nucleic acid species in the amplified mixture and is not shared by the other minor nucleic acid species in the amplified mixture, or (B) at least one of the one or more minor nucleic acid species shares a common chain terminating reagent with at least one other minor nucleic acid species in the amplified mixture, whereby the primers are extended up to, or through, the nucleotide positions that are different in the minor nucleic acid species relative to the major nucleic acid species, thereby generating chain terminated extension products corresponding to the minor nucleic acid species and the major nucleic acid species, respectively, where the concentration of the chain terminating reagent specific for the major nucleic acid species is less than the concentration(s) of each of the chain terminating reagent(s) specific for the one or more minor nucleic acid species; and (c) analyzing the extension products of (b), thereby identifying the presence or absence of the one or more minor nucleic acid species.

In certain embodiments, the nucleic acid population includes a plurality of minor nucleic acid species that are variants of a single major nucleic acid species and the plurality of minor nucleic acid species are identified in a single, multiplexed reaction. In some embodiments, part (b) of the method is performed in a set of at least two reaction vessels or compartments, where:

a first vessel or compartment includes extension conditions containing the chain terminating reagent that is specific for the major nucleic acid species and not containing a chain terminating reagent that is specific for the one or more minor nucleic acid species; and each of the remaining vessels or compartments includes extension conditions containing a single chain terminating reagent specific for and common to one or more minor nucleic acid species and not containing chain terminating reagents specific for the major nucleic acid species or specific for minor nucleic acid species that do not share the common, single chain terminating reagent. In some embodiments, the concentrations of each of the chain terminating reagents are known.

Also provided herein is a method for quantifying one or more minor nucleic acid species in a nucleic acid population that includes a mixture of the one or more minor nucleic acid species and a major nucleic acid species, where the minor nucleic acid species are variants of the same major nucleic acid species and are each present in a copy number that is less than the copy number of the major nucleic acid species, where the method includes:

(a) simultaneously amplifying target regions of the mixture with amplification primer pairs under amplification conditions that include dNTPs, whereby an amplified mixture of nucleic acids containing major and minor nucleic acid species is produced;

(b) contacting the amplified mixture with extension primers under extension conditions that include chain terminating reagents specific for (i) each of the one or more minor nucleic acid species, and (ii) the major nucleic acid species, whereby the primers are extended up to, or through, the nucleotide positions that are different in the minor nucleic acid species relative to the major nucleic acid species, thereby generating chain terminated extension products corresponding to the minor nucleic acid species and the major nucleic acid species, respectively, where: (1) the concentrations of each of the chain terminating reagents are known; and (2) the concentration of the chain terminating reagent specific for the major nucleic acid species is less than the concentration(s) of the chain terminating reagent(s) specific for the one or more minor nucleic acid species;

(c) determining the ratio of the amount(s) of extension products corresponding to each of the one or more minor nucleic acid species relative to the amount of extension product corresponding to the major nucleic acid species; and (d) based on the ratio of (c), and based on the concentration(s) of the chain terminating reagents specific for the one or more minor nucleic acid species relative to the concentration of the chain terminating reagent specific for the major nucleic acid species, quantifying the amount(s) of minor nucleic acid species relative to the amount of the major nucleic acid species.

Also provided is a multiplexed method for quantifying one or more minor nucleic acid species in a nucleic acid population that includes a mixture of the one or more minor nucleic acid species and a major nucleic acid species, where each minor nucleic acid species is a variant of a corresponding major nucleic acid species and is present in a copy number that is less than the copy number of its corresponding major nucleic acid species, where the method includes:

(a) simultaneously amplifying target regions of the mixture with amplification primer pairs under amplification conditions that include dNTPs, whereby an amplified mixture of nucleic acids comprising major and minor nucleic acid species is produced;

(b) contacting the amplified mixture with extension primers under extension conditions comprising chain terminating reagents, where:

(i) the one or more major nucleic acid species share a common chain terminating reagent that is specific for the major nucleic acid species and is not specific for the minor nucleic acid species, and (ii) each of the one or more minor nucleic acid species has a chain terminating reagent that is specific for the minor nucleic acid species and is not specific for the major nucleic acid species, where the chain terminating reagent that is specific for the minor nucleic acid species either: (A) is unique for a particular minor nucleic acid species in the amplified mixture and is not shared by the other minor nucleic acid species in the amplified mixture, or (B) at least one of the one or more minor nucleic acid species shares a common chain terminating reagent with at least one other minor nucleic acid species in the amplified mixture, whereby the primers are extended up to, or through, the nucleotide positions that are different in the minor nucleic acid species relative to the major nucleic acid species, thereby generating chain terminated extension products corresponding to the minor nucleic acid species and the major nucleic acid species, respectively, where: (1) the concentrations of each of the chain terminating reagents are known; and (2) the concentration of the chain terminating reagent specific for the major nucleic acid species is less than the concentration(s) of the chain terminating reagent(s) specific for the one or more minor nucleic acid species;

(c) determining the ratio of the amount(s) of extension products corresponding to each of the one or more minor nucleic acid species relative to the amount of extension product corresponding to the major nucleic acid species; and (d) based on the ratio of (c), and based on the concentration(s) of the chain terminating reagents specific for the one or more minor nucleic acid species relative to the concentration of the chain terminating reagent specific for the major nucleic acid species, quantifying the amount(s) of minor nucleic acid species relative to the amount of the major nucleic acid species.

In embodiments of the method, the nucleic acid population includes a plurality of minor nucleic acid species that are variants of a single major nucleic acid species and the plurality of minor nucleic acid species are identified in a single, multiplexed reaction. In certain embodiments, part (b) of the method is performed in a set of at least two reaction vessels or compartments, where:

a first vessel or compartment that includes extension conditions containing the chain terminating reagent that is specific for the major nucleic acid species and not containing a chain terminating reagent that is specific for the one or more minor nucleic acid species; and each of the remaining vessels or compartments includes extension conditions containing a single chain terminating reagent specific for and common to one or more minor nucleic acid species and not containing chain terminating reagents specific for the major nucleic acid species or specific for minor nucleic acid species that do not share the common, single chain terminating reagent.

In certain embodiments of the methods provided herein, the sequences of the minor and major nucleic acid species differ by a single base and the primers are extended up to, or through, the single base that is different. In some embodiments, the sequence of the minor nucleic acid species includes an insertion or a deletion relative to the sequence of the major nucleic acid species. In some embodiments, the one or more minor nucleic acid species are single nucleotide polymorphism (SNP) variants of the major nucleic acid species. In certain embodiments, the minor and major nucleic acid species are mutant and wild type alleles, respectively, of the same gene.

In some embodiments of the methods provided herein, the major nucleic acid species is from a host subject and the minor nucleic acid species are from a subject other than the host. In certain embodiments, the one or more minor nucleic acid species are each present in a copy number that is less than about 10% of the copy number of the major nucleic acid species. In certain embodiments, the one or more minor nucleic acid species are each present in a copy number that is between about 1% to less than 10% of the copy number of the major nucleic acid species. In some embodiments, the one or more minor nucleic acid species are each present in a copy number that is between about 2% to less than 10% of the copy number of the major nucleic acid species.

In certain embodiments of the methods provided herein, the concentration of the chain terminating reagent specific for the major nucleic acid species is between about 1% to about 20% of the concentration of each of the chain terminating reagent(s) specific for the minor nucleic acid species. In certain embodiments of the methods provided herein, the concentration of the chain terminating reagent specific for the major nucleic acid species is between about 0.1% to about 10% of the concentration of each of the chain terminating reagent(s) specific for the minor nucleic acid species. In certain embodiments of the methods provided herein, the concentration of the chain terminating reagent specific for the major nucleic acid species is between about 0.01% to about 5% of the concentration of each of the chain terminating reagent(s) specific for the minor nucleic acid species. In some embodiments, the chain terminating reagents are chain terminating nucleotides. In embodiments, the chain terminating nucleotides independently are selected from among ddATP, ddGTP, ddCTP, ddTTP and ddUTP.

In some embodiments of the methods provided herein, the chain terminating nucleotides specific for one or more of the minor nucleic acid species consist of one chain terminating nucleotide. In certain embodiments, the chain terminating nucleotides specific for one or more of the minor nucleic acid species consist of two chain terminating nucleotides. In some embodiments, the chain terminating nucleotides specific for one or more of the minor nucleic acid species consist of three chain terminating nucleotides.

In certain embodiments of the methods provided herein, the chain terminating reagents include one or more acyclic terminators. In embodiments of the methods provided herein, the amplification in part (a) includes between about 30 to about 45 PCR amplification cycles using the amplification primers. In some embodiments, the extension conditions in (b) include between about 20 to about 300 cycles of extending the extension primers. In certain embodiments, the extension conditions in (b) include at least 50 cycles of extension.

In embodiments of the methods provided herein, one or more of the chain terminating reagents and/or the extension primers includes a detectable label. In certain embodiments, the label is a fluorescent label or dye. In some embodiments, the label is a mass label. In embodiments, the label can be detected, whereby the one or more minor nucleic acid species are identified or quantified. In certain embodiments, the label is a mass label and detection is by mass spectrometry.

The methods provided herein include, in certain embodiments, amplification of the minor nucleic acid species and/or the major nucleic acid species, which is performed prior to extension (by a single base or a few bases, using chain terminators). In some embodiments, the amplification reaction conditions in (a) comprise water, genomic DNA, a buffer, dNTPs, the primer pairs, $MgCl_2$, and a polymerase, wherein the ratio of the concentration of $MgCl_2$ to the concentration of each one of the dNTPs is selected from 0:1, 9:1, 6:1, or 5:1. In certain embodiments, the polymerase is Taq polymerase at a concentration of at least about 0.03 units/μl. In embodiments of the methods provided herein, the amplification reaction conditions in (a) comprise between about 400-700 μM of each dNTP, about 100 nM primer pairs, and between about 1.6 up to about 4.8 mM $MgCl_2$. In some embodiments, a sequence tag is attached to one or more primers in the amplification primer pair. In some embodiments, the free $Mg^{2+}$ concentration is between 1.0-2.0 mM.

In some embodiments, particular $MgCl_2$ concentrations have been identified for the amplification performed in the methods herein that permit high levels (e.g., 7-plex up to 50-plex or more) of multiplexed PCR and primer extension reactions along with successful analysis of the extended products e.g., by detecting fluorescence signals or by mass spectrometry analysis. A consideration when selecting the concentrations of the dNTPs and $MgCl_2$ to use in the PCR amplification reaction that will be followed by a mass extension reaction and subsequent mass spectrometry analysis, is that the free Mg2+ concentration of the PCR reaction mixture should be kept within a particular range that is high enough to permit robust PCR amplification, while being low enough to not adversely affect the subsequent mass extension reaction and mass spectrometry analysis.

Accordingly, provided herein are multiplex methods of genotyping a plurality of polymorphic loci or other variants of minor nucleic acid species, by simultaneously amplifying a plurality of nucleic acid-target regions of the minority species and the corresponding regions of the majority nucleic acid species under amplification conditions whereby at least 60% of 7 or more nucleic acid target-regions are amplified by 7 or more primer pairs to produce an amplified mixture of nucleic acid-target regions containing polymorphic loci or other variants, contacting the amplified mixture of nucleic acid-target regions with 7 or more genotyping primers (i.e., extension primers or UEPs) in the presence of at least one chain terminating reagent specific for the major nucleic acid species and chain terminating reagents specific for the minor nucleic acid species under primer mass extension conditions whereby the primers are extended up to, or through, the respective polymorphic loci, wherein there is one genotyping primer for each polymorphic locus within a nucleic acid-target molecule, and detecting the extended genotyping primers by mass or other label, such as a fluorescent or electrochemical label, wherein at least 60% of the genotypes for said 7 or more nucleic acid target-regions attempted are determined. In certain embodiments, the quantity of amplification primer pairs can be selected from 8 or more, 9 or more, 10 or more, 11 or more, 12 or more, or 13 or more.

In certain embodiments of each of these methods described above, a sequence tag is attached to the 5' end of either one or both amplification primers of each primer pair. In other embodiments, the methods for performing multiplexed detection of a plurality of sequence variations are conducted using conditions (such as the amplification-reaction conditions and/or primer mass extension reaction conditions provided herein) that permit at least 65%, 70%, 75%, 80%, 85%, 90%, 91%, 92%, 93%, 94%, 95%, 96%, 97%, 98% or 99%, up to 100% of the attempted minor nucleic acid species to be determined (i.e., to be called). The conditions provided herein apply to numerous multiplexed reactions of 7-plex or more amplification reactions using a variety of amplification primer pairs and from a variety of target nucleic acids. In addition, all of the optimized amplification and/or primer mass extension genotyping reactions are applicable to multiplex assays ranging from 2-plex up to 6-plex and beyond, as described herein.

In particular embodiments, a sequence tag is attached to a plurality of primary and secondary amplification primer pairs selected from 13 or more, 14 or more, 15 or more, 16 or more, 17 or more, 18 or more, 19 or more, or 20 or more, 21, 22, 23, 24, 25, 26, 27, 28, 29, 30, 35, 40, 45, or or more primary and secondary primer pairs. The sequence tag can be attached to either one or both of the primary and secondary primers from each pair. Typically, the sequence tag is attached to the primary and secondary primer of each pair. The sequence tags used herein can range from 5 up to 20, from 5 up to 30, from 5 up to 40, or from 5 up to 50 nucleotides in length, with a sequence tag of 10-mer length being particularly useful in the methods provided herein. The sequence tag need not be the same sequence for each primer pair in the multiplexed amplification reaction, nor the same sequence for a primary and secondary primer within a particular amplification pair. In a particular embodiment, the sequence tag is the same for each primer in the multiplexed amplification reaction. For example, in certain embodiments, the sequence tag is a 10-mer and is attached to the 5' end of each primary and secondary primer. In particular embodiments of the methods provided herein, only a single primer pair is used to amplify each particular nucleic acid target (minor nucleic acid species) region.

In embodiments of the methods provided herein, the amplification reaction conditions for the methods described above comprise water, a mixture of minor and major nucleic acid species, a buffer, dNTPs, the primary and secondary primer pairs, $MgCl_2$, and a polymerase, wherein the ratio of the concentration of $MgCl_2$ to the concentration of each one of the dNTPs is selected from 9:1, 6:1, or 5:1. In a particular embodiment, the ratio of the concentration of $MgCl_2$ to the concentration of each one of the dNTPs is 7:1. In other embodiments, the amplification-reaction conditions comprise between about 400-700 μM, between about 500-600 μM, or about 500 μM of each dNTP, along with about 50-250 nM primer pairs. In these embodiments, the total $MgCl_2$ concentration can be between about 2.6 mM up to about 4.8 mM $MgCl_2$, between about 3.0 up to about 4.5 mM $MgCl_2$, and between about 3.5 mM up to about 4.0 mM $MgCl_2$. In embodiments, when selecting the concentrations of the dNTPs and $MgCl_2$, the free Mg2+ concentration is between about 1-2 mM. As used herein, the Free Mg2+ concentration=Total Mg2+ concentration (e.g., total [$MgCl_2$])−Total dNTP concentration for all 4 dNTPs (e.g., 200 μM each dNTP=800 μM total [dNTP]). In certain embodiments, the free Mg2+ is between 1.1-1.9 mM, between 1.2-1.8 mM, between 1.3-1.7 mM, between 1.4-1.6 mM. In a particular embodiment the free Mg2+ concentration is about 1.5 mM. For each of these methods, the multiplicity of amplification thermocycles can be about 30 to about 35, 40 or 45 cycles. In a particular embodiment, the amplification-reaction conditions comprise about 500 μM of each dNTP, about 100 nM primer pairs, and about 3.5 mM $MgCl_2$. For each of these methods, the polymerase can be a Taq polymerase (such as HOTSTARTAQ®, available from QIAGEN®) at a concentration of 0.03 units/μl. In particular embodiments of the methods provided herein, the amplification reaction conditions exclude the addition of one or any combination of the following additives selected from BSA (bovine serum albumin), glycerol, DMSO (dimethyl sulfoxide), urea or Q-SOLUTION®.

The extension primers (UEP) hybridize adjacent to the sequence variation and the mixture further comprises a preselected combination of dNTPs and ddNTPs or other chain terminating reagents such as reagents that include acyclic terminators. In the preselected combination of dNTPs and ddNTPs, when a ddNTP is present in the mixture, the same dNTP is absent. For these methods, the multiplicity of primer mass extension thermocycles is selected from at least about 50, 55, 60, 70, 75, 80, 85, 90, 95, 100, 125, 150, 175, 200 or more cycles. In embodiments of the method, the primer mass extension-reaction conditions comprise about 20 μM to about 300 μM ddNTPs or other chain terminating reagents specific for each minor nucleic acid species (C[Mut]), generally about 20 μM to about 200 μM ddNTPs, about 40 μM to about 200 μM ddNTPs, about 100 μM to about 200 μM ddNTPs, or about 50 μM ddNTPs, a concentration of chain terminating reagent specific for the major nucleic acid species C[WT] that is less than 20% of the concentration of the chain terminating reagents specific for the minority nucleic acid species (C[Mut]), C[WT] generally being between about 0.5% to less than about 20% of C[Mut], about 0.5% to less than about 15% of C[Mut], about 1% to about 15% of C[Mut], about 1% to about 10% of C[Mut], about 2% to about 10% of C[Mut] or about 1% to about 2% of C[Mut], and about 1 μM UEP primers. In certain embodiments, C[WT] is between about 0.1% to about 10% of C[Mut] or between about 0.01% to about 10% of C[Mut]. In certain embodiments for these primer extension reactions, the extension reaction conditions further comprise about 0.05 up to about 0.5 Units DNA polymerase per microliter. In other embodiments, the primer mass extension-reaction conditions further comprise about 0.1 up to about 0.3 Units DNA polymerase per microliter. In other embodiments, the primer mass extension-reaction conditions further comprise about 0.14 up to about 0.2 Units DNA polymerase per microliter. In an embodiment, the primer mass extension-reaction conditions further comprise about 0.14 Units DNA polymerase per microliter.

In certain embodiments, the primer extension reactions have the major species chain terminating regent is present in an amount that is about 0.1% to about 10% of the minor species chain terminating reagent(s). In other embodiments, the major species chain terminating reagent percentage is adjusted individually for each transition (i.e., A to C, A to G, A to T, C to A, C to G, C to T, G to A, G to C, G to T, T to A, T to C and T to G) to account for differences in transition specific incorporation of the chain terminating reagent. For example, the criterion for optimization of the percent of the major species chain terminating agent relative to a minor species chain terminating agent can be the relative peak height of the minor species peak to the major species peak for a specific minor species frequency (e.g., about 10% or less, about 5% or less, about 2.5% or less or about 1% or less). In certain embodiments, the adjusted major species chain terminating reagent percentage, depending on the specific transition, can be from about 0.1% to about 10%, about 0.1% to about 5%, about 1% to about 4% or about 0.1%, 0.2%, 0.3%, 0.4%. 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%. 2.5%, 2.6%, 2.7%, 2.8%, 2.9%, 3.0%, 3.1%, 3.2%, 3.3%, 3.4%. 3.5%, 3.6%, 3.7%, 3.8%, 3.9%, 4.0%, 4.1%, 4.2%, 4.3%, 4.4%. 4.5%, 4.6%, 4.7%, 4.8%, 4.9%, 5.0%, 5.1%, 5.2%, 5.3%, 5.4%. 5.5%, 5.6%, 5.7%, 5.8%, 5.9%, 6.0%, 6.1%, 6.2%, 6.3%, 6.4%. 6.5%, 6.6%, 6.7%, 6.8%, 6.9%, 7.0%, 7.1%, 7.2%, 7.3%, 7.4%. 7.5%, 7.6%, 7.7%, 7.8%, 7.9%, 8.0%, 8.1%, 8.2%, 8.3%, 8.4%. 8.5%, 8.6%, 8.7%, 8.8%, 8.9%, 9.0%, 9.1%, 9.2%, 9.3%, 9.4%. 9.5%, 9.6%, 9.7%, 9.8% or 9.9% relative to a minor species chain terminating reagent concentration, for example.

In certain embodiments, the adjusted major species chain terminating reagent percentage, depending on the specific transition, can be from about 0.01% to about 5%, about 0.01% to about 4% or about 0.01%, 0.02%, 0.03%, 0.04%. 0.05%, 0.06%, 0.07%, 0.08%, 0.09%, 0.1%, 0.2%, 0.3%, 0.4%. 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%. 2.5%, 2.6%, 2.7%, 2.8%, 2.9%, 3.0%, 3.1%, 3.2%, 3.3%, 3.4%. 3.5%, 3.6%, 3.7%, 3.8%, 3.9%, 4.0%, 4.1%, 4.2%, 4.3%, 4.4%. 4.5%, 4.6%, 4.7%, 4.8%, 4.9% or 5.0% relative to a minor species chain terminating reagent concentration, for example.

In some embodiments, for at least one primer pair in the plurality of amplification primer pairs, one primer is in lower concentration than the other primer. Alternatively, for each of the plurality of primer pairs, one primer is in lower concentration than the other primer. In such embodiments, the lower concentration primer for a particular nucleic acid target region (region in a minority nucleic acid species) can be in the same orientation as the extension (UEP) primer for that nucleic acid-target region. Further, the amplified products of the amplifying step can be single-stranded nucleic acid molecules.

Also provided are methods for performing multiplexed amplification of the minor and major nucleic acid species prior to extension, the method comprising: a) designing 7 or more pairs of primary and secondary primers, wherein each primer pair amplifies a particular nucleic acid target-region on a minor nucleic acid species; b) forming a mixture containing the plurality of primer pairs and one or more minor and major nucleic acid species to amplify a plurality of nucleic acid target-regions; and c) subjecting the mixture of step b) to a multiplicity of thermocycles under amplification-reaction conditions that permit amplification of greater than 60% of the 7 or more nucleic acid target-regions, wherein the amplification-reaction conditions comprise dNTPs and $MgCl_2$, and wherein the free Mg2+ concentration is between 1.0-2.0 mM (e.g., 1.1, 1.2, 1.3, 1.4, 1.5, 1.6, 1.7, 1.8, 1.9). In other embodiments, the quantity of primary and secondary primer pairs can be selected from 8 or more, 9 or more, 10 or more, 11 or more, 12 or more, or 13 or more.

In certain embodiments of each of these methods described above, a sequence tag is attached to the 5' end of either one or both primers of each amplification primer pair. In some embodiments, the amplification-reaction conditions provided herein permits amplification of a percentage of the 7 or more nucleic acid target-regions selected from greater than 60%, 65%, 70%, 75%, 80%, 85%, 90%, 91%, 92%, 93%, 94%, 95%, 96%, 97%, 98% or 99%, up to 100% of the 7 or more nucleic acid target-regions. The conditions provided herein apply to numerous multiplexed reactions of 7-plex or more amplification reactions using a variety of amplification primer pairs and from a variety of mixtures of major and minor nucleic acid species.

Certain embodiments are described further in the following description, claims and drawings.

BRIEF DESCRIPTION OF THE DRAWINGS

The drawings illustrate certain non-limiting embodiments of the technology and are not necessarily drawn to scale.

FIGS. 1A-C show the detection of a minor allele, present at 5% frequency relative to the major allele, using the methods provided herein.

FIGS. 2A-D show the incorporation, over time, of ddNTP chain terminating reagents into single base extension products corresponding to either wild type or mutant allele at various ratios of concentration of the wild type specific ddNTP ($C[WT]_{ddNTP}$) to the concentration of the mutant specific ddNTP ($C[Mut])_{ddNTP}$).

DETAILED DESCRIPTION

Figures 3A, 3B, 3C:
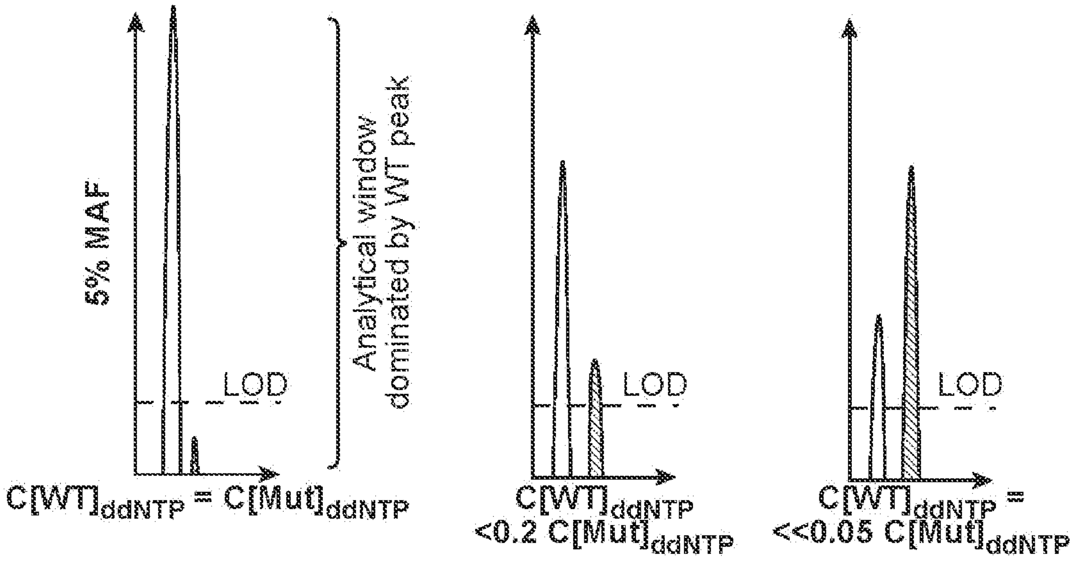
FIGS. 3A-I show the detection of a minor allele present at 5%, 2.5% or 1.25% frequency relative to the major allele, using the methods provided herein.

Provided herein are methods for identifying the presence or absence of one or more among a plurality of minor nucleic acid species present in a sample that contains a mixture of the one or more minor nucleic acid species and the one or more major nucleic acid species. Also provided are methods for quantifying the minor nucleic acid species (e.g., frequency or copy number) relative to the amount of major nucleic acid species in a sample.

The methods provided herein can be used to analyze minor nucleic acid species that are present at a frequency or copy number of about 0.25% up to about 50% relative to the major nucleic acid species, particular ranges including, but not limited to, about or at 0.25% to about or at 45%, 40%, 35%, 30%, 25%, 20%, 15%, 10%, 9.5%, 9%, 8.5%, 8%, 7.5%, 7%, 6.5%, 6%, 5.5%, 5%, 4.5%, 4%, 3.5%, 3%, 2.5%, 2%, 1.5% or 1%. In certain embodiments, the minor nucleic acid species is present at a frequency or copy number of about 1% or about 2% to about 10%, 9.5%, 9%, 8.5%, 8%, 7.5%, 7%, 6.5%, 6%, 5.5%, 5%, 4.5%, 4%, 3.5%, 3% or 2.5%, relative to the frequency or copy number of the major nucleic acid species. In embodiments, the minor nucleic acid species is present at a frequency of about 1% or about 2% to less than about 10%, relative to the frequency or copy number of the major nucleic acid species. In embodiments, the minor nucleic acid species is present at a frequency of about 5%, relative to the frequency or copy number of the major nucleic acid species The methods herein provide for improved detection sensitivity (detection limit) of a minor nucleic acid species relative to a major nucleic acid species, while permitting reliable identification and/or quantification relative to the presence and/or amount of the major nucleic acid species.

For example, in methods such as iPLEX™ or homogeneous MassExtend® (hME) (see, for example, U.S. Published Patent Application No. 2013/0237428 A1, U.S. Pat. Nos. 8,349,566, and 8,003,317, the contents of which are incorporated in their entirety by reference herein), a mixture of minor nucleic acid species (e.g., mutant alleles) and major nucleic acid species (e.g., wild type alleles) are subjected to a polymerase chain reaction (PCR) amplification using a set of amplification primers, a polymerase and deoxynucleotides (dNTPs), thereby generating amplicons of the wild type and mutant species. After treatment with shrimp alkaline phosphatase (SAP) to dephosphorylate unincorporated dNTPs, the amplicon mixture is extended using extension primers (unextended primers or UEPs), a polymerase and a termination mix that includes chain terminating reagents (e.g., dideoxynucleotides or ddNTPs). The UEPs hybridize to the amplicons and are extended either up to the site of variance between the mutant and wild type species (i.e., extension stops at the mutation site where there is a difference in bases between the mutant and wild type species to generate single base extension products or SBEs, as in iPLEX™) or a few bases (e.g., 2-3 bases) past the site of variance (as in, for example, the hME method). The resulting extension products can then be processed (e.g., by desalting prior to mass spectrometry) and analyzed for the presence of the mutant alleles based on a difference in detection signal (e.g., mass) relative to the wild type allele.

The above-described iPLEX™ and homogeneous MassExtend® (hME) methods use an equimolar mixture of ddNTPs in the extension step for generating extension products corresponding to wild type and mutant species. Thus, in the iPLEX™ and homogeneous MassExtend® (hME) methods, all other factors being equal with the exception of the major nucleic acid species being present in a large excess relative to the minor nucleic acid species, the majority of the UEPs hybridize to the major nucleic acid species and are extended using the chain terminating reagent specific for the major nucleic acid species. Relatively few molecules of UEP are available for hybridization and extension of the minor nucleic acid species. This compromises the magnitude of the detection signal corresponding to the minor nucleic acid species, which is overshadowed by the predominant detection signal from the major nucleic acid species and may be subsumed by background noise.

In contrast, the methods provided herein perform the extension step using a limiting concentration of chain terminating reagent specific for the wild type or major nucleic acid species, relative to the chain terminating reagents specific for the mutant or minor nucleic acid species. When the chain terminating reagent specific for the major nucleic acid species is added at a concentration that is lower than the concentration of the chain terminating reagents specific for the one or more minor nucleic acid species, a fewer number of UEPs will be extended using the major nucleic acid species as template, thereby leaving larger numbers of UEPs available for extension using the minor nucleic acid species as a template. Thus, over a series of extension cycles, more extension products corresponding to the minor nucleic acid species accumulate, thereby increasing the detection signal corresponding to the minor nucleic acid species and improving the sensitivity (limits) of detection. The methods provided herein, where the concentrations of the chain terminating reagents are skewed in favor of extending the amplicons generated from the minor nucleic acid species, can be used to analyze any minor nucleic acid species that is present at a frequency less than that of a major nucleic acid species in a sample of interest. In embodiments, the methods are advantageous for the detection of minor nucleic acid species that are present at a copy number or frequency that is less than 10% of the copy number or frequency of the major nucleic acid species, e.g., at a frequency of about 0.25% to less than 10%, about 0.5% to less than 10%, about 1% to less than 10% or about 2% to less than 10% of the copy number or frequency of a major nucleic acid species.

FIGS. 1A-C demonstrate an embodiment of the methods provided herein. A sample containing a mixture of a minor nucleic acid species (minority allele) and a major nucleic acid species (majority allele), where the minority allele is present at 5% frequency relative to the majority allele, is subjected to amplification and extension reactions according to the iPLEX™ method or according to the methods provided herein, thereby providing extension products for detection and analysis. The extreme left panel (FIG. 1A) shows the results of analysis using the iPLEX™ method, in which equimolar concentrations of the chain terminating reagents are used. As the panel shows, the signal peak on the left, which corresponds to the extension product from the majority allele, is so predominant that the minority peak on the right is reduced to the level of background noise and is undetectable. The middle panel (FIG. 1B) shows the results obtained when the concentration of the chain terminating reagent specific for the majority allele is 20% (one fifth) that of the concentration of the chain terminating reagent specific for the minority allele. As seen in the middle panel, the intensity of the detection signal from the minority allele extension product (right peak) is now higher and more visible relative to the signal from the majority allele extension product (left peak). The minority allele signal, however, is still small and close to the level of background noise. The extreme right panel (FIG. 10) shows the results obtained when the concentration of the of the chain terminating reagent specific for the majority allele is about 6-7% (one fifteenth) that of the concentration of the chain terminating reagent specific for the minority allele. As seen in the right panel, the signal from the minority allele extended product (right peak) is now comparable to the signal from the majority allele (left peak). Thus, FIGS. 1A-C demonstrates that by skewing the concentration of the chain terminating reagents in favor of the minor nucleic acid species, minor nucleic acid species at frequencies of less than 10%, which could not effectively be detected by methods such as iPLEX™, can be detected by the methods provided herein.

The concentration of the chain terminating reagents specific for the majority nucleic acid species (C[WT]) relative to the concentration of the chain terminating reagents specific for the minority nucleic acid species (C[Mut])) is adjusted such that the ratio of the two concentrations, C[WT]:C[Mut], is not so high as to render the minority nucleic acid species undetectable. In some embodiments, the ratio can be adjusted for each minority species, depending on the copy number or frequency of each minority nucleic acid species relative to a corresponding majority nucleic acid species. In general, for minority nucleic acid species present at frequencies of 10% or less relative to the majority nucleic acid species, the concentration of the chain terminating reagent specific for the majority nucleic acid species C[WT] is less than 20% of the concentration of the chain terminating reagents specific for the minority nucleic acid species (C[Mut]), C[WT] generally being between about 0.5% to less than about 20% of C[Mut], about 0.5% to less than about 15% of C[Mut], about 1% to about 15% of C[Mut], about 1% to about 10% of C[Mut], about 2% to about 10% of C[Mut] or about 1%, 1.5%, 2%, 2.5%, 3%, 3.5%, 4%, 4.5%, 5%, 5.5%, 6%, 6.5%, 7%, 7.5%, 8%, 8.5%, 9%, 9.5% or 10% of C[Mut]. In certain embodiments, C[WT] is between about 0.1% to about 10% of C[Mut], between about 0.01% to about 10% of C[Mut] or about 0.01%, 0.05%, 0.1%, 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5% or 10% of C[Mut]. The ratio of the two concentrations cannot be too low, i.e., C[WT] cannot be much less than C[Mut]. When C[WT] is much lower than C[Mut], the amount of extended product obtained for the majority nucleic acid species will be low, resulting in a low detection signal for the majority nucleic acid species. In addition, however, because the minority nucleic acid species generally is present in a 10% or less amount relative to the majority nucleic acid species in the sample and, therefore, there is a limit to how much minority extension product can be generated, the signal from the minority species extension products is unlikely to be much higher than the signal from the majority species extension product, even if C[Mut] is much higher than C[WT]. Thus, when C[WT] is much lower than C[Mut], signals from the both major and the minor nucleic acid species, while comparable to one another, could be too low and too close to background noise to be detectable.

FIG. 2A-D depicts the analysis of detection signal from a minority nucleic acid species relative to the detection signal from a majority nucleic acid species, at various relative concentrations of ddNTP chain terminators specific for the majority species ($C[WT]_{ddNTP}$) and ddNTP chain terminators specific for the minority species ($(C[Mut])_{ddNTP}$). After PCR amplification and SAP treatment, amplicons of the minor and major nucleic acid species in the sample are a sufficient amount of available as templates for extension, e.g., by a single base extension reaction using ddNTP chain terminator nucleotides and extension primers (UEPs). The molarity of the UEP primers is higher than the molarity of the PCR amplification primers, allowing for a signal amplification through repeated cycling during extension. Because of the vast excess of amplicons corresponding to the major nucleic acid species compared to the minor nucleic acid species, most of the UEPs are elongated with the chain terminator nucleotide specific for the major nucleic acid species ($[WT]_{ddNTP}$) and hence only a fraction of the UEPs will be elongated with the chain terminator nucleotide specific for the minor nucleic acid species ($([Mut])_{ddNTP}$). After the first cycle of extension, a large portion of the UEP primers are elongated using the major nucleic acid species as template, reducing the number of available UEP primers for the next cycle of extension. These extended UEP primers, i.e., single base extension products of the major nucleic acid species (SBE-WT) will also serve as competitors to the unextended primers (UEP) as they will bind to the template major nucleic acid species and minor nucleic acid species amplicons (SBE-WT will compete with UEP for both the major and minor nucleic acid species amplicons, thereby reducing the amount of extension product generated using the UEP). If the concentration of the chain terminator ddNTP specific for the major nucleic acid species ($C[WT]_{ddNTP}$) is equal to the concentration of the chain terminator ddNTP specific for the minor nucleic acid species ($(C[Mut])_{ddNTP}$), and if the minor nucleic acid species is present at a frequency or copy number below 10% that of the major nucleic acid species in the sample, the signal corresponding to the minor nucleic acid species could be so low relative to the signal corresponding to the minor nucleic acid species as to render it undetectable over the background noise. This is illustrated in the top panel FIG. 2A (from left to right: signal from unextended primer, signal from major nucleic acid species extension product, signal from minor nucleic acid species extension product; horizontal dotted line represents background, i.e., detection limit indistinguishable from noise).

If, on the other hand, $C[WT]_{ddNTP}$ is less than $C[Mut])_{ddNTP}$, then the consumption of UEP primers by the relatively large amount of major nucleic acid species in the sample is lower, allowing more UEP primers to be available for extension from the amplicons corresponding to the minor nucleic acid species in the following cycles. Because $C[Mut])_{ddNTP}$ is significantly higher than $C[WT]_{ddNTP}$, the reaction goes to completion during every cycle and hence over the total number of cycles of the single base extension reaction, a much higher number of UEPs will be extended with the ddNTP specific for the minor nucleic acid species, thereby generating a higher signal relative to the signal corresponding to the major nucleic acid species and distinct from the background noise. This is illustrated in the second and third panels from the top, in FIGS. 2B and 2C (from left to right: signal from unextended primer, signal from major nucleic acid species extension product, signal from minor nucleic acid species extension product; horizontal dotted line represents background, i.e., detection limit indistinguishable from noise). Thus, the methods provided herein permit the detection of minor nucleic acid species that are present at frequencies of less than 10% relative to that of the major nucleic acid species, by using a lower concentration of $[WT]_{ddNTP}$ relative to $[Mut])_{ddNTP}$. However, if too few $[WT]_{ddNTP}$ molecules are added to the extension reaction, then extension of the major nucleic acid species amplicons will essentially be inhibited which, when combined with a low frequency of the minor nucleic acid species, could generate low peak signals for both the major and minor nucleic acid species. In embodiments of the method, the signal from the major nucleic acid species can be used as a positive control, to ensure the integrity of the method. Thus if the signal from the major nucleic acid species is too low, then it no longer can be detected as a positive control and, in addition, the signal from the minor nucleic acid species also could be too low for accurate identification. This is illustrated in the bottom panel of FIG. 2D (from left to right: signal from unextended primer, signal from major nucleic acid species extension product, signal from minor nucleic acid species extension product; horizontal dotted line represents background, i.e., detection limit indistinguishable from noise).

Figure 3D:
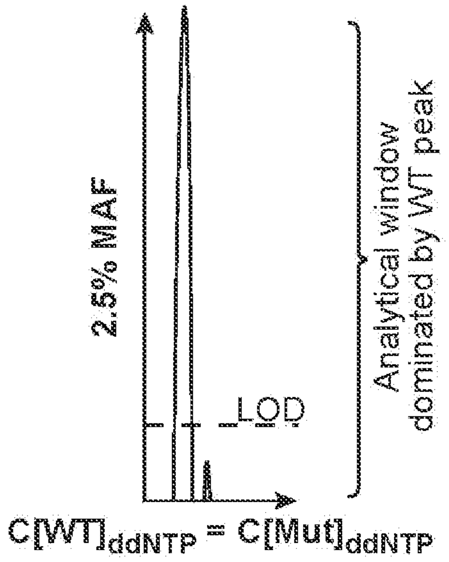
Figure 3E:
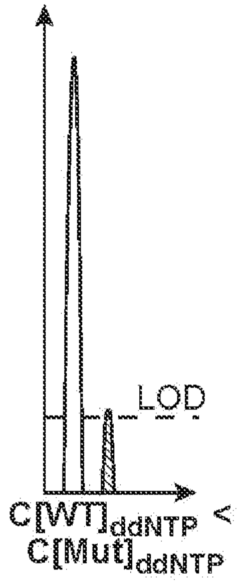
Figure 3F:
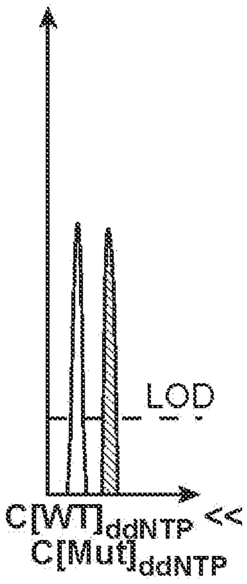
Figures 3G, 3H, 3I:
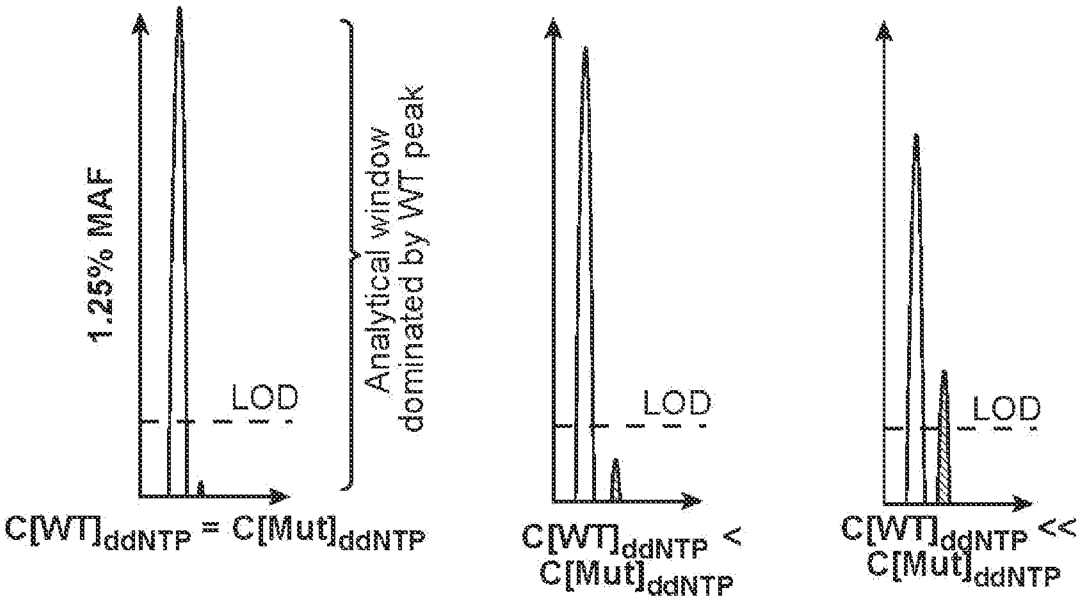

As shown in FIGS. 3A-I, the methods provided herein can be useful for the detection of minor nucleic acid species that are present at a frequency of less than 2%, as low as 1.25%, relative to the major nucleic acid species in a sample. FIGS. 3A-I show a comparison of the results obtained when the sample is subjected to amplification, followed by extension under three conditions: (A) concentration of chain terminator ddNTP specific for the major nucleic acid species (wild type allele; $C[WT]_{ddNTP}$) is equal to the concentration of chain terminator ddNTP specific for the minor nucleic acid species (mutant allele; $C[Mut])_{ddNTP}$); (B) $C[WT]_{ddNTP}$) is less than about 20% of the concentration of $C[Mut])_{ddNTP}$ (i.e., ratio of $C[WT]_{ddNTP}$:$C[Mut])_{ddNTP}$ is 0.2); and (C) $C[WT]_{ddNTP}$) is less than about 5% of the concentration of $C[Mut])_{ddNTP}$ (i.e., ratio of $C[WT]_{ddNTP}$:$C[Mut])_{ddNTP}$ is 0.05). As seen in FIGS. 3A, 3D and 3G, when the ratio of $C[WT]_{ddNTP}$:$C[MUt])_{ddNTP}$ is 1, i.e., the two chain terminator concentrations are equal (as used, e.g., in the iPLEX™ method) mutant allele frequencies of 5%, 2.5% and 1.25% were all below the limit of detection (LOD). When the ratio of $C[WT]_{ddNTP}$:$C[Mut])_{ddNTP}$ was decreased to 0.2, mutant allele frequencies of 5% could be detected, while the 2.5% and 1.25% mutant allele frequencies were still below the limit of detection (see FIGS. 3B, 3E and 3H). When the ratio of $C[WT]_{ddNTP}$:$C[MUt])_{ddNTP}$ was further decreased to 0.05, all three mutant allele frequencies (5%, 2.5% and 1.25%) could be detected (see FIGS. 3C, 3F and 3I).

The methods provided herein can also be used for the quantification of one or more minor nucleic acid species (frequency or copy number, e.g.) relative to the amount of major nucleic acid species in a sample. For example, if the relative concentrations of the chain terminator reagents specific for the major nucleic acid species and the minor nucleic acid species are known (i.e., C[WT] and C[Mut] are known), then the relative amounts of minor and major nucleic acid species can be derived from the ratio of C[WT]:C[Mut], using a normalization coefficient. In embodiments of the method, the extension reactions are linearly amplified in each extension cycle, and the relative amounts of minor and major nucleic acid species are inversely proportional to the ratio of C[WT]:C[Mut]. Thus, the presence of a detectable amount of signal corresponding to the major nucleic acid species provides a positive control for integrity of the method and also can be used to quantify the amounts of one or more minor nucleic acid species (frequency or copy number, e.g.) relative to the amount of major nucleic acid species in the sample.

The methods provided herein can be adapted to a multiplexed format. For example, when analyzing a plurality of minor nucleic acid species that are variants (e.g., mutants, alleles, polymorphisms, deletion variants, insertion variants, etc.) of a plurality of major nucleic acid species, multiplexing can be performed in a series of reaction vessels, compartments or containers where each container has an extension reaction mix that contains only one chain terminating reagent (e.g., either ddATP, ddCTP, ddUTP, ddGTP or ddTTP). All major nucleic acid species having the same specific chain terminating reagent (e.g., all single base extension products of these major nucleic acid species terminate in a ddATP) can be extended in one container. Similarly, all minor nucleic acid species having the same specific chain terminating reagent can be extended in another container. Using a series of containers, one can analyze signals from a plurality of target minor nucleic acid species, the containers each having a relatively high concentration of chain terminating reagent for each group of minor nucleic acid species that shares a common specific chain terminating reagent, relative to the signals generated using lower concentrations of major nucleic acid species-specific chain terminating reagents in the containers where amplicons of the major nucleic acid species are extended. In an embodiment of the multiplexed method, a plurality of minor nucleic acid species that are all variants of the same major nucleic acid species are analyzed.

The extension products corresponding to major and minor nucleic acid species that are obtained by the methods provided herein can be detected by a variety of methods. For example, the extension primers (UEPs) and/or the chain terminating reagents may be labeled with any type of chemical group or moiety that allows for detection of a signal and/or quantification of the signal including, but not limited to, mass labels, radioactive molecules, fluorescent molecules, antibodies, antibody fragments, haptens, carbohydrates, biotin, derivatives of biotin, phosphorescent moieties, luminescent moieties, electrochemiluminescent moieties, moieties that generate an electrochemical signal upon oxidation or reduction, e.g., complexes of iron, ruthenium or osmium (see, for example, eSensor technology used by Genmark Diagnostics, Inc. e.g., as described in Pierce et al., J. Clin. Micribiol., 50(11):3458-3465 (2012)), chromatic moieties, and moieties having a detectable electron spin resonance, electrical capacitance, dielectric constant or electrical conductivity, or any combination of labels thereof.

The labeled extension products corresponding to the minor and major nucleic acid species can be analyzed by a variety of methods including, but not limited to, mass spectrometry, MALDI-TOF mass spectrometry, fluorescence detection, DNA sequencing gel, capillary electrophoresis on an automated DNA sequencing machine, microchannel electrophoresis, and other methods of sequencing, mass spectrometry, time of flight mass spectrometry, quadrupole mass spectrometry, magnetic sector mass spectrometry, electric sector mass spectrometry infrared spectrometry, ultraviolet spectrometry, palentiostatic amperometry, measurement of current/electrochemical signal or by DNA hybridization techniques including Southern Blots, Slot Blots, Dot Blots, and DNA microarrays, wherein DNA fragments would be useful as both "probes" and "targets," ELISA, fluorimetry, Fluorescence Resonance Energy Transfer (FRET), SNP-IT, GeneChips, HuSNP, BeadArray, TaqMan assay, Invader assay, MassExtend®, or MassCleave® method.

The methods provided herein can be utilized, for example, to: (a) rapidly determine whether a particular target sequence (e.g. a target sequence comprising a genetic variation) is present in a sample; (b) perform mixture analysis, e.g., identify a mixture and/or its composition or determine the frequency of a target sequence in a mixture (e.g., mixed communities, quasispecies); (c) detect sequence variations (e.g., mutations, single nucleotide polymorphisms) in a sample; (d) perform haplotyping determinations; (e) perform microorganism (e.g., pathogen) typing; (f) detect the presence or absence of a microorganism target sequence in a sample; (g) identify disease markers; (h) detect microsatellites; (i) identify short tandem repeats; (j) identify an organism or organisms; (k) detect allelic variations; (l) determine allelic frequency; (m) determine methylation patterns; (n) perform epigenetic determinations; (o) re-sequence a region of a biomolecule; (p) perform analyses in human clinical research and medicine (e.g. cancer marker detection, sequence variation detection; detection of sequence signatures favorable or unfavorable for a particular drug administration), (q) perform HLA typing; (r) perform forensics analyses; (s) perform vaccine quality control analyses; (t) monitor treatments; (u) perform vector identity analyses; (v) perform vaccine or production strain quality control and (w) test strain identity (x) plants. Such methods also can be utilized, for example, in a variety of fields, including, without limitation, in commercial, education, medical, agriculture, environmental, disease monitoring, military defense, and forensics fields.

Nucleic Acids

As used herein, the term "nucleic acid" refers to an oligonucleotide or polynucleotide, including, without limitation, natural nucleic acids (e.g., deoxyribonucleic acid (DNA), ribonucleic acid (RNA)), synthetic nucleic acids, non-natural nucleic acids (e.g., peptide nucleic acid (PNA)), unmodified nucleic acids, modified nucleic acids (e.g., methylated DNA or RNA, labeled DNA or RNA, DNA or RNA having one or more modified nucleotides). Reference to a nucleic acid as a "polynucleotide" refers to two or more nucleotides or nucleotide analogs linked by a covalent bond. Nucleic acids may be any type of nucleic acid suitable for use with processes described herein. A nucleic acid in certain embodiments can be DNA (e.g., complementary DNA (cDNA), genomic DNA (gDNA), plasmids and vector DNA and the like), RNA (e.g., viral RNA, message RNA (mRNA), short inhibitory RNA (siRNA), ribosomal RNA (rRNA), tRNA and the like), and/or DNA or RNA analogs (e.g., containing base analogs, sugar analogs and/or a non-native backbone and the like). A nucleic acid can be in any form useful for conducting processes herein (e.g., linear, circular, supercoiled, single-stranded, double-stranded and the like). A nucleic acid may be, or may be from, a plasmid, phage, autonomously replicating sequence (ARS), centromere, artificial chromosome, chromosome, a cell, a cell nucleus or cytoplasm of a cell in certain embodiments. A nucleic acid in some embodiments is from a single chromosome (e.g., a nucleic acid sample may be from one chromosome of a sample obtained from a diploid organism). In the case of fetal nucleic acid, the nucleic acid may be from the paternal allele, the maternal allele or the maternal and paternal allele.

The term "minor nucleic acid species," as used herein with reference to a target nucleic acid, amplicon, primer, sequence tag, polynucleotide, or oligonucleotide, refers to one nucleic acid having a nucleotide sequence that differs by one or more nucleotides from the nucleotide sequence of another nucleic acid, the "major nucleic acid species," when the nucleotide sequences are aligned. Thus, a first nucleic acid species differs from a second nucleic acid species when the sequences of the two species, when aligned, differ by one or more nucleotides (e.g., about 1, 2, 3, 4, 5, 10, 15, 20, 25, 30, 35, 40, 45, 50, 55, 60, 65, 70, 75, 80, 85, 90, 95, 100 or more than 100 nucleotide differences). In certain embodiments, the number of nucleic acid species, such as minor or major nucleic acid species, amplicon species obtained by PCR amplification of the minor or major nucleic acid species or extended oligonucleotide species, includes, but is not limited to about 2 to about 10000 nucleic acid species, about 2 to about 1000 nucleic acid species, about 2 to about 500 nucleic acid species, or sometimes about 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 80, 85, 90, 95, 100, 125, 150, 175, 200, 225, 250, 275, 300, 325, 350, 375, 400, 425, 450, 475, 500, 600, 700, 800, 900, 1000, 2000, 3000, 4000, 5000, 6000, 7000, 8000, 9000 or 10000 nucleic acid species.

As used herein, the term "minor nucleic acid species" or "target nucleic acid species" can refer to any nucleic acid species of interest in a sample. A minor nucleic acid species can include, without limitation, (i) a particular minority allele amongst two or more possible alleles, and (ii) a nucleic acid having, or not having, a particular mutation, nucleotide substitution, sequence variation, repeat sequence, marker or distinguishing sequence. As used herein, the term "major nucleic acid species" refers to nucleic acid species that differs from the minor nucleic acid species by one or more features and is present in the sample at a frequency or copy number that is higher than that of the minor nucleic acid species. As used herein, the term "genetic variation" refers to nucleic acid species that differ by one or more features. As used herein, the term "variant" refers to nucleic acid species that differ by one or more features. Features include, without limitation, one or more methyl groups or a methylation state, one or more phosphates, one or more acetyl groups, and one or more deletions, additions or substitutions of one or more nucleotides. Examples of one or more deletions, additions or substitutions of one or more nucleotides include, without limitation, the presence or absence of a particular mutation, presence or absence of a nucleotide substitution (e.g., single nucleotide polymorphism (SNP)), presence or absence of a repeat sequence (e.g., di-, tri-, tetra-, penta-nucleotide repeat), presence or absence of a marker (e.g., microsatellite) and presence of absence of a distinguishing sequence (e.g., a sequence that distinguishes one organism from another (e.g., a sequence that distinguishes one viral strain from another viral strain)). Different target nucleic acids may be distinguished by any known method, for example, by mass, binding, distinguishable tags and the like, as described herein.

In the methods provided herein, the sample can contain a mixture of one or more "minor nucleic acid" species and one or more "major nucleic acid" species, or a mixture can be generated by combining more than one sample containing minor nucleic acid species and major nucleic acid species. The minor nucleic acid species includes a variant of a major nucleic acid species and can include, but is not limited to, a mutant (minor nucleic acid) of a wild type (major nucleic acid) allele, a variant of a gene that is found in more than one host (e.g., a viral oncogene (minor nucleic acid) that is a variant of a normal, healthy gene (major nucleic acid)), a polymorphism, including a single nucleotide polymorphism (SNP), an insertion, deletion or other mutated form of the major nucleic acid species. The minor nucleic acid species is present in the sample (or combination of samples) at a frequency or copy number that is between about 0.25% up to about 50% relative to the major nucleic acid species, particular ranges including, but not limited to, about or at 0.25% to about or at 45%, 40%, 35%, 30%, 25%, 20%, 15%, 10%, 9.5%, 9%, 8.5%, 8%, 7.5%, 7%, 6.5%, 6%, 5.5%, 5%, 4.5%, 4%, 3.5%, 3%, 2.5%, 2%, 1.5% or 1%. In certain embodiments, the minor nucleic acid species is present at a frequency or copy number of about 1% or about 2% to about 10%, 9.5%, 9%, 8.5%, 8%, 7.5%, 7%, 6.5%, 6%, 5.5%, 5%, 4.5%, 4%, 3.5%, 3% or 2.5%, relative to the frequency or copy number of the major nucleic acid species. In embodiments, the minor nucleic acid species is present at a frequency of about 1% or about 2% to less than about 10%, relative to the frequency or copy number of the major nucleic acid species.

As used herein, the term "plurality" of target nucleic acids, minor nucleic acid species and/or major nucleic acid species refers to more than one target nucleic acid species, minor nucleic acid species and/or major nucleic acid species. A plurality can be about 2 to about 10000 nucleic acid species, about 2 to about 1000 nucleic acid species, about 2 to about 500 nucleic acid species, or sometimes about 2, 3, 4, 5, 6, 7, 8, 9, 10, 11, 12, 13, 14, 15, 16, 17, 18, 19, 20, 25, 30, 35, 40, 45, 55, 60, 65, 70, 75, 80, 80, 85, 90, 95, 100, 125, 150, 175, 200, 225, 250, 275, 300, 325, 350, 375, 400, 425, 450, 475, 500, 600, 700, 800, 900, 1000, 2000, 3000, 4000, 5000, 6000, 7000, 8000, 9000 or 10000 nucleic acid species, in certain embodiments. Detection or identification of nucleic acids results in detection of the minor nucleic acid species and can indicate the presence or absence of a particular mutation, sequence variation (mutation or polymorphism) or genetic variation (e.g. sequence variation, sequence difference or polymorphism). Detection or identification of nucleic acids also generally results in detection or identification of the major nucleic acid species, which can serve as a positive control and/or as a basis for quantifying the minor nucleic acid species. Within the plurality of minor nucleic acid and major nucleic acid species, there can be detection and/or quantification of the same or different species; detection and/or quantification of minor nucleic acid species that are all variants of the same major nucleic acid species or a plurality of minor nucleic acid species that are variants of a plurality of major nucleic acid species.

In some embodiments an oligonucleotide species is hybridized to a nucleic acid template (e.g. an amplicon) thereby forming a double stranded nucleic acid and the oligonucleotide species that is hybridized to the template is referred to herein as a hybridized oligonucleotide species. In some embodiments a hybridized oligonucleotide species can comprise one or more nucleotides that are not hybridized to the template. For example, a hybridized oligonucleotide species can comprise one or more mismatched nucleotides (e.g. non-complementary nucleotides) and sometimes a 5' and/or 3' region of nucleotides that do not hybridize. In some embodiments a hybridized oligonucleotide species comprises a tag (e.g. a mass distinguishable tag, a sequence tag, a light emitting tag or a radioactive tag). In some embodiments a hybridized oligonucleotide species comprises a capture agent (e.g. biotin, or any member of binding pair). In some embodiments a hybridized oligonucleotide species comprises a terminating nucleotide.

The term "chain terminating reagent," used interchangeably with "chain terminator reagent" or "chain terminator" herein refers to a molecule which, when added to an extension primer, stops the extension reaction. Chain terminators can include nucleotide analogs which, when present in a polynucleotide chain, prevent further extension of the chain. Exemplary chain terminating reagents that are chain terminating nucleotides include dideoxynucleotides e.g., ddA (dideoxyadenine), ddT (dideoxythymine), ddC (dideoxycytosine), ddG (dideoxyguanine) and ddU (dideoxyuracil).

As used herein, the term "nucleotides" refers to natural and non-natural nucleotides. Nucleotides include, but are not limited to, naturally occurring nucleoside mono-, di-, and triphosphates: deoxyadenosine mono-, di- and triphosphate; deoxyguanosine mono-, di- and triphosphate; deoxythymidine mono-, di- and triphosphate; deoxycytidine mono-, di- and triphosphate; deoxyuridine mono-, di- and triphosphate; and deoxyinosine mono-, di- and triphosphate (referred to herein as dA, dG, dT, dC, dU and dl, or A, G, T, C, U and I respectively). Nucleotides also include, but are not limited to, modified nucleotides and nucleotide analogs. Modified nucleotides and nucleotide analogs include, without limitation, deazapurine nucleotides, e.g., 7-deaza-deoxyguanosine (7-deaza-dG) and 7-deaza-deoxyadenosine (7-deaza-dA) mono-, di- and triphosphates, deutero-deoxythymidine (deutero-dT) mon-, di- and triphosphates, methylated nucleotides e.g., 5-methyldeoxycytidine triphosphate, $^{13}C/^{15}N$ labeled nucleotides and deoxyinosine mono-, di- and triphosphate. Modified nucleotides, isotopically enriched nucleotides, depleted nucleotides, tagged and labeled nucleotides and nucleotide analogs can be obtained using a variety of combinations of functionality and attachment positions.

The term "composition" as used herein with reference to nucleic acids refers to a tangible item that includes one or more nucleic acids. A composition sometimes is a sample extracted from a source, but also a composition of all samples at the source, and at times is the source of one or more nucleic acids. A composition can comprise nucleic acids. In some embodiments, a composition can comprise genomic DNA. In some embodiments, a composition can comprise maternal DNA, fetal DNA or a mixture of maternal and fetal DNA. In some embodiments, a composition can comprise fragments of genomic DNA. In some embodiments a composition can comprise nucleic acids derived from a virus, bacteria, yeast, fungus, mammal or mixture thereof.

A nucleic acid sample can be derived from one or more sources and can contain a mixture of minor nucleic acid species and major nucleic acid species. Samples also can be combined to generate a mixture that includes minor nucleic acid species and major nucleic acid species. A sample may be collected from an organism, mineral or geological site (e.g., soil, rock, mineral deposit, fossil), or forensic site (e.g., crime scene, contraband or suspected contraband), for example. Thus, a source may be environmental, such as geological, agricultural, combat theater or soil sources, for example. A source also may be from any type of organism such as any plant, fungus, protistan, moneran, virus or animal, including but not limited, human, non-human, mammal, reptile, cattle, cat, dog, goat, swine, pig, monkey, ape, gorilla, bull, cow, bear, horse, sheep, poultry, mouse, rat, fish, dolphin, whale, and shark, or any animal or organism that may have a detectable nucleic acids. Sources also can refer to different parts of an organism such as internal parts, external parts, living or non-living cells, tissue, fluid and the like. A sample therefore may be a "biological sample," which refers to any material obtained from a living source or formerly-living source, for example, an animal such as a human or other mammal, a plant, a bacterium, a fungus, a protist or a virus. A source can be in any form, including, without limitation, a solid material such as a tissue, cells, a cell pellet, a cell extract, or a biopsy, or a biological fluid such as urine, blood, saliva, amniotic fluid, exudate from a region of infection or inflammation, or a mouth wash containing buccal cells, hair, cerebral spinal fluid and synovial fluid and organs. A sample also may be isolated at a different time point as compared to another sample, where each of the samples are from the same or a different source. A nucleic acid may be from a nucleic acid library, such as a cDNA or RNA library, for example. A nucleic acid may be a result of nucleic acid purification or isolation and/or amplification of nucleic acid molecules from the sample. Nucleic acids provided for sequence analysis processes described herein may contain nucleic acid from one sample or from two or more samples (e.g., from 1, 2, 3, 4, 5, 6, 7, 8, 9, 10, 11, 12, 13, 14, 15, 16, 17, 18, 19, 20, 25, 50, 75, 100, 200, 300, 400, 500, 600, 700, 800, 900 or 1000 or more samples).

Nucleic acids may be treated in a variety of manners during, prior to or subsequent to the methods provided herein. For example, a nucleic acid may be reduced in size (e.g., sheared, digested by nuclease or restriction enzyme, de-phosphorylated, de-methylated), increased in size (e.g., phosphorylated, reacted with a methylation-specific reagent, attached to a detectable label), treated with inhibitors of nucleic acid cleavage and the like.

Nucleic acids may be provided for analysis according to the methods provided herein without processing, in certain embodiments. In some embodiments, nucleic acid is provided for conducting methods described herein after processing. For example, a nucleic acid may be extracted, isolated, purified or amplified from a sample. The term "isolated" as used herein refers to nucleic acid removed from its original environment (e.g., the natural environment if it is naturally occurring, or a host cell if expressed exogenously), and thus is altered "by the hand of man" from its original environment. An isolated nucleic acid generally is provided with fewer non-nucleic acid components (e.g., protein, lipid) than the amount of components present in a source sample. A composition comprising isolated nucleic acid can be substantially isolated (e.g., about 90%, 91%, 92%, 93%, 94%, 95%, 96%, 97%, 98%, 99% or greater than 99% free of non-nucleic acid components). The term "purified" as used herein refers to nucleic acid provided that contains fewer nucleic acid species than in the sample source from which the nucleic acid is derived. A composition comprising nucleic acid may be substantially purified (e.g., about 90%, 91%, 92%, 93%, 94%, 95%, 96%, 97%, 98%, 99% or greater than 99% free of other nucleic acid species).

Nucleic acids may be processed by a method that generates nucleic acid fragments, in certain embodiments, before providing nucleic acid for a process described herein. In some embodiments, nucleic acid subjected to fragmentation or cleavage may have a nominal, average or mean length of about 5 to about 10,000 base pairs, about 100 to about 1,00 base pairs, about 100 to about 500 base pairs, or about 10, 15, 20, 25, 30, 35, 40, 45, 50, 55, 60, 65, 70, 75, 80, 85, 95, 100, 200, 300, 400, 500, 600, 700, 800, 900, 1000, 2000, 3000, 4000, 5000, 6000, 7000, 8000, 9000 or 10000 base pairs. Fragments can be generated by any suitable method known in the art, and the average, mean or nominal length of nucleic acid fragments can be controlled by selecting an appropriate fragment-generating procedure. In certain embodiments, nucleic acid of a relatively shorter length can be utilized to analyze sequences that contain little sequence variation and/or contain relatively large amounts of known nucleotide sequence information. In some embodiments, nucleic acid of a relatively longer length can be utilized to analyze sequences that contain greater sequence variation and/or contain relatively small amounts of unknown nucleotide sequence information.

Amplification and Extension

In embodiments of the methods provided herein, nucleic acid species (e.g., minor and/or major nucleic acid species) can be amplified in certain embodiments. As used herein, the term "amplifying," and grammatical variants thereof, refers to a process of generating copies of a template nucleic acid. For example, nucleic acid template may be subjected to a process that linearly or exponentially generates two or more nucleic acid amplicons (copies) having the same or substantially the same nucleotide sequence as the nucleotide sequence of the template, or a portion of the template. Nucleic acid amplification often is specific (e.g., amplicons have the same or substantially the same sequence), and sometimes can be non-specific (e.g., amplicons have different sequences) in certain embodiments. Nucleic acid amplification sometimes is beneficial when the amount of target sequence present in a sample is low. By amplifying the target sequences and detecting the amplicon synthesized, sensitivity of an assay can be improved, since fewer target sequences are needed at the beginning of the assay for detection of a target nucleic acid. A nucleic acid species (minor or major nucleic acid species) sometimes is not amplified prior to hybridizing an extension oligonucleotide (primer, i.e., UEP), in certain embodiments.

Amplification conditions are known and can be selected for a particular nucleic acid that will be amplified. Amplification conditions include certain reagents some of which can include, without limitation, nucleotides (e.g., nucleotide triphosphates), modified nucleotides, oligonucleotides (e.g., primer oligonucleotides for polymerase-based amplification and oligonucleotide building blocks for ligase-based amplification), one or more salts (e.g., magnesium-containing salt), one or more buffers, one or more polymerizing agents (e.g., ligase enzyme, polymerase enzyme), one or more nicking enzymes (e.g., an enzyme that cleaves one strand of a double-stranded nucleic acid) and one or more nucleases (e.g., exonuclease, endonuclease, RNase). Any polymerase suitable for amplification may be utilized, such as a polymerase with or without exonuclease activity, DNA polymerase and RNA polymerase, mutant forms of these enzymes, for example. Any ligase suitable for joining the 5' of one oligonucleotide to the 3' end of another oligonucleotide can be utilized. Amplification conditions also can include certain reaction conditions, such as isothermal or temperature cycle conditions. Methods for cycling temperature in an amplification process are known, such as by using a thermocycle device. The term "cycling" refers to amplification (e.g. an amplification reaction or extension reaction) utilizing a single primer or multiple primers where temperature cycling is used. Amplification conditions also can, in some embodiments, include an emulsion agent (e.g., oil) that can be utilized to form multiple reaction compartments within which single nucleic acid molecule species can be amplified. Amplification is sometimes an exponential product generating process and sometimes is a linear product generating process.

A strand of a single-stranded nucleic acid target can be amplified and one or two strands of a double-stranded nucleic acid target can be amplified. An amplification product (amplicon), in some embodiments, is about 10 nucleotides to about 10,000 nucleotides in length, about 10 to about 1000 nucleotides in length, about 10 to about 500 nucleotides in length, 10 to about 100 nucleotides in length, and sometimes about 10, 11, 12, 13, 14, 15, 16, 17, 18, 19, 20, 25, 30, 35, 40, 45, 50, 55, 60, 65, 70, 75, 80, 80, 85, 90, 95, 100, 125, 150, 175, 200, 225, 250, 275, 300, 325, 350, 375, 400, 425, 450, 475, 500, 600, 700, 800, 900 or 1000 nucleotides in length.

Any suitable amplification technique and amplification conditions can be selected for a particular nucleic acid for amplification. Known amplification processes include, without limitation, polymerase chain reaction (PCR), extension and ligation, ligation amplification (or ligase chain reaction (LCR)) and amplification methods based on the use of Q-beta replicase or template-dependent polymerase (see US Patent Publication Number US20050287592). Also useful are strand displacement amplification (SDA), thermophilic SDA, nucleic acid sequence based amplification (3SR or NASBA) and transcription-associated amplification (TAA). Reagents, apparatus and hardware for conducting amplification processes are commercially available, and amplification conditions are known and can be selected for the target nucleic acid at hand.

Polymerase-based amplification can be effected, in certain embodiments, by employing universal primers. In such processes, hybridization regions that hybridize to one or more universal primers are incorporated into a template nucleic acid. Such hybridization regions can be incorporated into (i) a primer that hybridizes to a target nucleic acid and is extended, and/or (ii) an oligonucleotide that is joined (e.g., ligated using a ligase enzyme) to a target nucleic acid or a product of (i), for example. Amplification processes that involve universal primers can provide an advantage of amplifying a plurality of target nucleic acids using only one or two amplification primers, for example.

Certain minor nucleic acid species and major nucleic acid species, either before or after amplification, can be extended in certain embodiments. The term "extension," and grammatical variants thereof, as used herein refers to elongating one strand of a nucleic acid. For example, an oligonucleotide that hybridizes to a minor or major nucleic acid species or an amplicon generated from a minor or major nucleic acid species can be extended in certain embodiments. An extension reaction is conducted under extension conditions, and a variety of such conditions are known and selected for a particular application. Extension conditions can include certain reagents, including without limitation, one or more oligonucleotides, extension nucleotides (e.g., nucleotide triphosphates (dNTPs)), chain terminating reagents or nucleotides (e.g., one or more dideoxynucleotide triphosphates (ddNTPs) or acyclic terminators), one or more salts (e.g., magnesium-containing salt), one or more buffers (e.g., with beta-NAD, Triton X-100), and one or more polymerizing agents (e.g., DNA polymerase, RNA polymerase). The concentration of the chain terminating reagent specific for the major nucleic acid species C[WT] generally is less than about 20% of the concentration of the chain terminating reagents specific for the minor nucleic acid species (C[Mut]), C[WT] generally being between about 0.5% to less than about 20% of C[Mut], about 0.5% to less than about 15% of C[Mut], about 1% to about 15% of C[Mut], about 1% to about 10% of C[Mut], about 2% to about 10% of C[Mut] or about 1%, 1.5%, 2%, 2.5%, 3%, 3.5%, 4%, 4.5%, 5%, 5.5%, 6%, 6.5%, 7%, 7.5%, 8%, 8.5%, 9%, 9.5% or 10% of C[Mut]. In certain embodiments, C[WT] is between about 0.1% to about 10% of C[Mut], between about 0.01% to about 10% of C[Mut] or about 0.01%, 0.05%, 0.1%, 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5% or 10% of C[Mut].

Extension can be conducted under isothermal conditions or under non-isothermal conditions (e.g., thermocycled conditions), in certain embodiments. One or more nucleic acid species can be extended in an extension reaction, and one or more molecules of each nucleic acid species can be extended. A nucleic acid can be extended by one or more nucleotides, and in some embodiments, the extension product is about 10 nucleotides to about 10,000 nucleotides in length, about 10 to about 1000 nucleotides in length, about 10 to about 500 nucleotides in length, 10 to about 100 nucleotides in length, and sometimes about 10, 11, 12, 13, 14, 15, 16, 17, 18, 19, 20, 25, 30, 35, 45, 50, 55, 60, 65, 70, 75, 80, 80, 85, 90, 95, 100, 125, 150, 175, 200, 225, 250, 275, 300, 325, 350, 375, 400, 425, 450, 475, 500, 600, 700, 800, 900 or 1000 nucleotides in length. Incorporation of a terminating nucleotide (e.g., ddNTP), the hybridization location, or other factors, can determine the length to which the oligonucleotide is extended. In certain embodiments, amplification and extension processes are carried out in the same detection procedure.

In some embodiments an extension reaction includes multiple temperature cycles repeated to amplify the amount of extension product in the reaction. In some embodiments the extension reaction is cycled 2 or more times. In some embodiments the extension reaction is cycled 10 or more times. In some embodiments the extension reaction is cycled about 10, 15, 20, 50, 55, 60, 70, 75, 80, 85, 90, 95, 100, 200, 300, 400, 500 or 600 or more times. In some embodiments the extension reaction is cycled 20 to 50 times. In some embodiments the extension reaction is cycled to 100 times. In some embodiments the extension reaction is cycled 20 to 300 times. In some embodiments the extension reaction is cycled 200 to 300 times. In certain embodiments, the extension reaction is cycled at least 50, 55, 60, 65, 70, 75, 80, 85, 90, 95 or 100 times.

In some embodiments a minor or major nucleic acid species is extended in the presence of an extension composition, where the nucleic acid species is extended by one nucleotide. An extension composition can comprise one or more buffers, salts, enzymes (e.g. polymerases, Klenow, etc.), water, templates (e.g. DNA, RNA, amplicons, etc.), primers (e.g. oligonucleotides), nucleotide triphosphates, glycerol, macromolecular exclusion molecules and any other additives used in the art. An extension composition can include terminating nucleotides (e.g. dideoxynucleotides (e.g. ddNTPs)) or other chain terminating reagents, non-terminating or extension nucleotides (e.g. dNTPs) or a mixture of terminating nucleotides and non-terminating nucleotides. An extension composition consisting essentially of a particular terminating nucleotide or terminating nucleotides, can contain any other component of an extension composition (e.g. buffers, salts, templates, primers, etc.), but does not contain any other terminating nucleotide or nucleotide triphosphate (e.g. dNTP) except those specified. For example an extension composition consisting essentially of ddTTP and ddCTP does not contain ddATP, ddGTP or any other dNTP. In some embodiments the nucleotides in an extension composition are only terminating nucleotides and the target nucleic acid is extended by one nucleotide (i.e. sometimes there are no extension nucleotides in the extension composition). In some embodiments an extension composition consists essentially of terminating nucleotides (e.g. ddNTPs). In embodiments of the methods provided herein, the concentration of the chain terminating reagent specific for the majority nucleic acid species C[WT] is less than 20% of the concentration of the chain terminating reagents specific for the minority nucleic acid species (C[Mut]), C[WT] generally being between about 0.5% to less than about 20% of C[Mut], about 0.5% to less than about 15% of C[Mut], about 1% to about 15% of C[Mut], about 1% to about 10% of C[Mut], about 2% to about 10% of C[Mut] or about 1%, 1.5%, 2%, 2.5%, 3%, 3.5%, 4%, 4.5%, 5%, 5.5%, 6%, 6.5%, 7%, 7.5%, 8%, 8.5%, 9%, 9.5% or 10% of C[Mut]. In certain embodiments, C[WT] is between about 0.1% to about 10% of C[Mut], between about 0.01% to about 10% of C[Mut] or about 0.01%, 0.05%, 0.1%, 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5% or 10% of C[Mut].

In some embodiments, a chain terminating reagent or chain terminating nucleotide comprises one or more detectable labels. The detectable label can include, but is not limited to, including, but not limited to, mass labels, radioactive molecules, fluorescent molecules, antibodies, antibody fragments, haptens, carbohydrates, biotin, derivatives of biotin, phosphorescent moieties, luminescent moieties, electrochemiluminescent moieties, moieties that generate an electrochemical signal upon oxidation or reduction, e.g., complexes of iron, ruthenium or osmium (see, for example, eSensor technology used by Genmark Diagnostics, Inc. e.g., as described in Pierce et al., J. Clin. Micribiol., 50(11):3458-3465 (2012)), chromatic moieties, and moieties having a detectable electron spin resonance, electrical capacitance, dielectric constant or electrical conductivity, or any combination of labels thereof. In some embodiments, a chain terminating reagent or chain terminating nucleotide includes one detectable label. In some embodiments, a first chain terminating reagent or chain terminating nucleotide includes a detectable label that is different from the detectable label of a second chain terminating reagent or chain terminating nucleotide. In some embodiments, an extension composition includes one or more chain terminating reagents or chain terminating nucleotides where each chain terminating reagent or chain terminating nucleotide includes a different detectable label. In some embodiments, an extension composition includes one or more chain terminating reagents or chain terminating nucleotides where each contains the same detection label. In some embodiments, an extension composition includes a chain terminating reagent or chain terminating nucleotide and an extension nucleotide (e.g., dNTP) and one or more of the nucleotides (e.g. terminating nucleotides and/or extension nucleotides) includes a detection label.

Any suitable extension reaction can be selected and utilized. An extension reaction can be utilized, for example, to discriminate SNP alleles by the incorporation of deoxynucleotides and/or dideoxynucleotides to an extension oligonucleotide that hybridizes to a region adjacent to the SNP site in a target nucleic acid. The primer often is extended with a polymerase. In some embodiments, the oligonucleotide is extended by only one deoxynucleotide or dideoxynucleotide complementary to the SNP site. In some embodiments, an oligonucleotide may be extended by dNTP incorporation and terminated by a ddNTP, or terminated by ddNTP incorporation without dNTP extension in certain embodiments. Extension may be carried out using unmodified extension oligonucleotides and unmodified dideoxynucleotides, unmodified extension oligonucleotides and biotinylated dideoxynucleotides, extension oligonucleotides containing a deoxyinosine and unmodified dideoxynucleotides, extension oligonucleotides containing a deoxyinosine and biotinylated dideoxynucleotides, extension by biotinylated dideoxynucleotides, or extension by biotinylated deoxynucleotide and/or unmodified dideoxynucleotides, in some embodiments.

In some embodiments an oligonucleotide species can hybridize, under hybridization conditions, to a template (e.g. a minor or major nucleic acid species) adjacent to a genetic variation or variant (e.g. the 3' end of the oligonucleotide species may be located 5' of the genetic variation site and may be 0 to 10 nucleotides away from the 5' end of the genetic variation site). Several variants may exist at a site of genetic variation in a target nucleic acid. A genetic variant sometimes is a single nucleotide polymorphism (SNP) or single nucleotide variant. Several single nucleotide variants may exist at a single base position on a template target located 3' of a hybridized oligonucleotide. Several single nucleotide variants may differ by a single base located at a position on a template target that is 3' of a hybridized oligonucleotide species. In some embodiments an oligonucleotide species is extended by one nucleotide at the variant position. The oligonucleotide can be extended by any one of five terminating nucleotides (e.g. ddATP, ddUTP, ddTTP, ddGTP, ddCTP), depending on the number of variants present, in some embodiments. A major nucleic acid species and its minor nucleic acid species variants, or a corresponding amplicon, can act as the template and can, in part, determine which terminating nucleotide is added to the oligonucleotide in the extension reaction. A major nucleic acid species may have two or more minor nucleic acid species variants. In some embodiments, a major nucleic acid species has two, three or four minor nucleic acid species variants.

In multiplexed forms of the methods provided herein, a major nucleic acid species and one or more of its minor nucleic acid species variants can be analyzed in a single reaction container and the chain terminating reagent specific for the major nucleic acid species is different from the chain terminating reagent(s) specific for the one or more minor nucleic acid species. In certain embodiments, the minor nucleic acid species are all terminated by the same chain terminating reagent, which is different from the chain terminating reagent specific for the major nucleic acid species.

In some embodiments, at least one minor nucleic acid species has a chain terminating reagent that is different from the chain terminating reagents of the other minor nucleic acid species. In certain embodiments, the chain terminating reagents of each of the minor nucleic acid species in the reaction are different from one another and also different from the chain terminating reagent specific for the major nucleic acid species.

In some multiplexed forms of the methods provided herein, a mixture of more than one major nucleic acid species and more than one minor nucleic acid species can be analyzed in a series of reaction containers. All major nucleic acid species having the same specific chain terminating reagent are subjected to extension (to generate, e.g., single base extension products using the chain terminating reagent) in the same reaction container and, in embodiments, the only chain terminating reagent in the container is the chain terminating reagent that is specific (and common to) the major nucleic acid species in the container. Similarly, all minor nucleic acid species having the same specific chain terminating reagent are subjected to extension in the same reaction container and, in embodiments, the only chain terminating reagent in the container is the chain terminating reagent that is specific (and common to) the minor nucleic acid species in the container.

In embodiments of the methods provided herein, including multiplexed forms of the method, the concentrations of the chain terminating reagents specific for the major nucleic acid species (C[WT]) can be less than 20% of the concentration of the chain terminating reagents specific for the minor nucleic acid species (C[Mut]), C[WT] generally being between about 0.5% to less than about 20% of C[Mut], about 0.5% to less than about 15% of C[Mut], about 1% to about 15% of C[Mut], about 1% to about 10% of C[Mut], about 2% to about 10% of C[Mut] or about 1%, 1.5%, 2%, 2.5%, 3%, 3.5%, 4%, 4.5%, 5%, 5.5%, 6%, 6.5%, 7%, 7.5%, 8%, 8.5%, 9%, 9.5% or 10% of C[Mut]. In certain embodiments, C[WT] is between about 0.1% to about 10% of C[Mut], between about to about 10% of C[Mut] or about 0.01%, 0.05%, 0.1%, 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5% or 10% of C[Mut].

The resulting extension products can be identified by detection labels that can be present on one or more of the extension primer (UEP), the chain terminating reagent, and one or more nucleotides if present in the extension reactions. The labels can be any type of chemical group or moiety that allows for detection of a signal and/or quantification of the signal including, but not limited to, mass labels, radioactive molecules, fluorescent molecules, antibodies, antibody fragments, haptens, carbohydrates, biotin, derivatives of biotin, phosphorescent moieties, luminescent moieties, electrochemiluminescent moieties, moieties that generate an electrochemical signal upon oxidation or reduction, e.g., complexes of iron, ruthenium or osmium (see, for example, eSensor technology used by Genmark Diagnostics, Inc. e.g., as described in Pierce et al., J. Clin. Micribiol., (2012)), chromatic moieties, and moieties having a detectable electron spin resonance, electrical capacitance, dielectric constant or electrical conductivity, or any combination of labels thereof.

The labeled extension products corresponding to the minor and major nucleic acid species can be analyzed by a variety of methods including, but not limited to, mass spectrometry, MALDI-TOF mass spectrometry, fluorescence detection, DNA sequencing gel, capillary electrophoresis on an automated DNA sequencing machine, microchannel electrophoresis, and other methods of sequencing, mass spectrometry, time of flight mass spectrometry, quadrupole mass spectrometry, magnetic sector mass spectrometry, electric sector mass spectrometry infrared spectrometry, ultraviolet spectrometry, palentiostatic amperometry, measurement of current/electrochemical signal or by DNA hybridization techniques including Southern Blots, Slot Blots, Dot Blots, and DNA microarrays, wherein DNA fragments would be useful as both “probes” and “targets,” ELISA, fluorimetry, Fluorescence Resonance Energy Transfer (FRET), SNP-IT, GeneChips, HuSNP, BeadArray, TaqMan assay, Invader assay, MassExtend®, or MassCleave® method.

In some embodiments, the relative amounts (frequency or copy number, e.g.) of the minor nucleic acid species relative to that of the major nucleic acid species can be determined by the proportions of their detection signals relative to the ratio of the concentrations of the chain terminating reagents specific for the major nucleic acid species to the concentrations of the chain terminating reagents specific for the minor nucleic acid species, using a normalization coefficient. In embodiments of the method, amplification of the major and minor nucleic acid species during extension is linear and proportional to the relative amounts of molecules of a minor nucleic acid species, a major nucleic acid species and the relative concentrations (ratios) of their chain terminating reagents in the assay. In some embodiments the amount (e.g. copy number, concentration, percentage) of minor nucleic acid species s quantified by normalizing the ratio of the signal for the minor nucleic acid species to the signal for the major nucleic acid species, using a coefficient. This coefficient is inversely proportional to the fraction of concentration of the chain terminating reagent or nucleotide specific for the major nucleic acid species compared to the concentration of the chain terminating reagent or nucleotide specific for the minor nucleic acid species (i.e., the lower the fraction of major nucleic acid species-specific chain terminating reagent relative to the chain terminating reagent specific for the minor nucleic acid species, the larger the coefficient). In embodiments of the methods provided herein, the chain terminating reagent specific for the major nucleic acid species is added in an amount sufficient to generate a detectable signal, which can serve as a positive control for identifying the presence or absence of a minor nucleic acid species and also can serve as a basis for quantifying the relative amounts (frequency or copy number, e.g.) of minor nucleic acid species in a sample.

In some embodiments, one minor nucleic acid species can be in greater abundance than other minor nucleic acid species. In some embodiments, the relative concentrations of the chain terminating reagents specific for each of the various minor nucleic acid species can be adjusted to optimize the magnitude of the detection signals corresponding to each of the minor nucleic acid species. In some embodiments a major nucleic acid species includes a first, second and third variant minor nucleic acid species where the second variant is represented in greater abundance over the first and third variant. In some embodiments a major nucleic acid species includes a first, second, third and fourth variant minor nucleic acid species, where the second variant is represented in greater abundance over the first, third and fourth variant. A variant that is represented in a greater abundance generally is present at a higher concentration or is represented by a greater number of molecules (e.g. copies) when compared to another variant. A higher concentration can be 2-fold or more. In some embodiments, a higher concentration is 10-fold or more. In some embodiments, a higher concentration is a 100-fold, a 1000-fold or 10000-fold or more. In some embodiments, a major nucleic acid species is present at a 100-fold or higher concentration than a minor nucleic acid species. In some embodiments, a minor nucleic acid species represents less than 30%, 20%, 15%, 10%, 8%, 5%, 4%, 3%, 2%, 1%, 0.8%, 0.75%, 0.1%, 0.05%, 0.01% or less of the major nucleic acid species. In some embodiments a minor nucleic acid species represents between about 5% to about 0.75% of the major nucleic acid species. In some embodiments, a minor nucleic acid species represents less than 30%, 20%, 15%, 10%, 8%, 5%, 4%, 3%, 2%, 1%, 0.8%, 0.75%, 0.5%, 0.1%, 0.05%, 0.01% or less of the total nucleic acid in a composition.

In some embodiments, a terminating nucleotide that is present (or, in some embodiments absent) in an extension composition determines which terminating nucleotide is added to an oligonucleotide. In some embodiments, an extension composition includes one or more terminating nucleotides (e.g. ddNTPs). In some embodiments, an extension composition includes one or more terminating nucleotides and one or more non-terminating nucleotides (e.g. dNTPs). In some embodiments, an extension composition comprises only terminating nucleotides that correspond to a specific minor nucleic acid species or a major nucleic acid species and, therefore only allow extension of that species. In some embodiments, in samples containing a plurality of minor nucleic acid species, an extension composition includes only those terminating nucleotides that correspond to the minor nucleic acid species (variants) that are desired to be detected.

The term "signal to noise ratio" as used herein refers to the quantitative measurement of the quality of a signal by quantifying the ratio of intensity of a signal relative to noise when using a detection process (e.g., mass spectrometry). In some embodiments, an intensive peak on one spectrum has a greater signal to noise ratio than a low intensity peak generated by the same analyte (e.g., an extended oligonucleotide species) on another spectrum. In some embodiments, noise is generated by extended oligonucleotide species derived from major nucleic acid species (e.g. wild type alleles, second variants, wild type variants). In some embodiments, the signal generated from an extended oligonucleotide species derived from a minor nucleic acid species (e.g., mutant variant, mutant allele, SNP) is obscured by the noise generated by a more abundant minor or major extended oligonucleotide species. The term "signal" as used in the phrase "signal to noise ratio" herein refers to the intensity of a signal peak of an extended oligonucleotide species. In some embodiments, the term "signal" as used in the phrase "signal to noise ratio" herein generally refers to the intensity of a signal peak of an extended oligonucleotide species derived from a minor nucleic acid species (e.g., mutant variant, mutant allele, SNP). In some embodiments, a terminating nucleotide that would allow extension of a major nucleic acid species (e.g. a wild type allele) is added at a concentration that permits enhancement of the signal generated by extension of the minor nucleic acid species, while still providing a major nucleic acid species signal for serving as a control and as a basis for quantifying the minor nucleic acid species.

The term "sensitivity" as used herein refers to an amount of analyte that can be detected at a given signal-to-noise ratio when using a detection process (e.g., mass spectrometry). In some embodiments, sensitivity can be improved by decreasing the background or noise level. In some embodiments, noise is generated by extended oligonucleotide species derived from major nucleic acid species (e.g. wild type alleles, wild type variants). In some embodiments, sensitivity is increased when the signal generated from an extended oligonucleotide species derived from a major nucleic acid species is reduced.

Any suitable type of nucleotides can be incorporated into an amplification product or an extension product. Nucleotides may be naturally occurring nucleotides, terminating nucleotides, or non-naturally occurring nucleotides (e.g., nucleotide analog or derivative), in some embodiments. Certain nucleotides can comprise a detectable label and/or a member of a binding pair or a fluorescent label pair for detection by FRET (e.g., one member of the pair can be on the terminating nucleotide that is incorporated into the UEP by extension and the other member of the pair can be elsewhere on the extension product oligonucleotide), in some embodiments.

A solution containing amplicons produced by an amplification process, or a solution containing extension products produced by an extension process, can be subjected to further processing. For example, a solution can be contacted with an agent that removes phosphate moieties from free nucleotides that have not been incorporated into an amplicon or extension product. An example of such an agent is a phosphatase (e.g., an alkaline phosphatase, such as shrimp alkaline phosphatase). Amplicons and extension products also may be associated with a solid phase, may be washed, may be contacted with an agent that removes a terminal phosphate (e.g., exposure to a phosphatase), may be contacted with an agent that removes a terminal nucleotide (e.g., exonuclease), may be contacted with an agent that cleaves (e.g., endonuclease, ribonuclease), and the like.

The term "oligonucleotide" as used herein refers to two or more nucleotides or nucleotide analogs linked by a covalent bond. An oligonucleotide is of any convenient length, and in some embodiments is about 5 to about 200 nucleotides in length, about 5 to about 150 nucleotides in length, about 5 to about 100 nucleotides in length, about 5 to about 75 nucleotides in length or about 5 to about 50 nucleotides in length, and sometimes is about 5, 6, 7, 8, 9, 10, 11, 12, 13, 14, 16, 17, 18, 19, 20, 25, 30, 35, 40, 45, 50, 55, 60, 65, 70, 75, 80, 80, 85, 90, 95, 100, 125, 150, 175, or 200 nucleotides in length. Oligonucleotides may include deoxyribonucleic acid (DNA), ribonucleic acid (RNA), naturally occurring and/or non-naturally occurring nucleotides or combinations thereof and any chemical or enzymatic modification thereof (e.g. methylated DNA, DNA of modified nucleotides). The length of an oligonucleotide sometimes is shorter than the length of an amplicon or target nucleic acid, but not necessarily shorter than a primer or polynucleotide used for amplification. An oligonucleotide often comprises a nucleotide subsequence or a hybridization sequence that is complementary, or substantially complementary, to an amplicon, target nucleic acid or complement thereof (e.g., about 95%, 96%, 97%, 98%, 99% or greater than 99% identical to the amplicon or target nucleic acid complement when aligned). An oligonucleotide may contain a nucleotide subsequence not complementary to, or not substantially complementary to, an amplicon, target nucleic acid or complement thereof (e.g., at the 3' or 5' end of the nucleotide subsequence in the primer complementary to or substantially complementary to the amplicon). An oligonucleotide in certain embodiments, may contain a detectable molecule (e.g., a tag, fluorophore, radioisotope, colormetric agent, particle, enzyme and the like) and/or a member of a binding pair, in certain embodiments (e.g., biotin/avidin, biotin/streptavidin).

The term "in solution" as used herein refers to a liquid, such as a liquid containing one or more nucleic acids, for example. Nucleic acids and other components in solution may be dispersed throughout, and a solution often comprises water (e.g., aqueous solution). A solution may contain any convenient number of oligonucleotide species, and there often are at least the same number of oligonucleotide species as there are amplicon species or target nucleic acid species to be detected.

The term "hybridization sequence" as used herein refers to a nucleotide sequence in an oligonucleotide capable of specifically hybridizing to an amplicon, target nucleic acid or complement thereof. The hybridization sequence is readily designed and selected and can be of a length suitable for hybridizing to an amplicon, target sequence or complement thereof in solution as described herein. In some embodiments, the hybridization sequence in each oligonucleotide is about 5 to about 200 nucleotides in length (e.g., about 5 to 10, about 10 to 15, about 15 to 20, about 20 to 25, about 25 to 30, about 30 to 35, about 35 to 40, about 40 to 45, or about 45 to 50, about 50 to 70, about 80 to 90, about 90 to 110, about 100 to 120, about 110 to 130, about 120 to 140, about 130 to 150, about 140 to 160, about 150 to 170, about 160 to 180, about 170 to 190, about 180 to 200 nucleotides in length).

The term "hybridization conditions" as used herein refers to conditions under which two nucleic acids having complementary nucleotide sequences can interact with one another. Hybridization conditions can be high stringency, medium stringency or low stringency, and conditions for these varying degrees of stringency are known. Hybridization conditions often are selected that allow for amplification and/or extension depending on the application of interest.

The term "specifically hybridizing to one amplicon or target nucleic acid" as used herein refers to hybridizing substantially to one amplicon species or target nucleic acid species and not substantially hybridizing to other amplicon species or target nucleic acid species in the solution. Specific hybridization rules out mismatches so that, for example, an oligonucleotide may be designed to hybridize specifically to a certain allele and only to that allele. An oligonucleotide that is homogenously matched or complementary to an allele will specifically hybridize to that allele, whereas if there are one or more base mismatches then no hybridization may occur.

The term "hybridization location" as used herein refers to a specific location on an amplicon or target nucleic acid to which another nucleic acid hybridizes. In certain embodiments, the terminus of an oligonucleotide is adjacent to or substantially adjacent to a site on an amplicon species or target nucleic acid species that has a different sequence than another amplicon species or target nucleic acid species. The terminus of an oligonucleotide is "adjacent" to a site when there are no nucleotides between the site and the oligonucleotide terminus. The terminus of an oligonucleotide is "substantially adjacent" to a site when there are 1, 2, 3, 4, 5, 6, 7, 8, 9 or 10 nucleotides between the site and the oligonucleotide terminus, in certain embodiments.

Distinguishable Labels and Release

As used herein, the terms "distinguishable labels" and "distinguishable tags" refer to types of labels or tags that can be distinguished from one another and used to identify the nucleic acid to which the tag is attached. A variety of types of labels and tags may be selected and used for multiplex methods provided herein. For example, oligonucleotides, amino acids, small organic molecules, light-emitting molecules, light-absorbing molecules, light-scattering molecules, luminescent molecules, isotopes, enzymes and the like may be used as distinguishable labels or tags. In certain embodiments, oligonucleotides, amino acids, and/or small molecule organic molecules of varying lengths, varying mass-to-charge ratios, varying electrophoretic mobility (e.g., capillary electrophoresis mobility) and/or varying mass also can be used as distinguishable labels or tags. Accordingly, a fluorophore, radioisotope, colormetric agent, light emitting agent, chemiluminescent agent, light scattering agent, and the like, may be used as a label. The choice of label may depend on the sensitivity required, ease of conjugation with a nucleic acid, stability requirements, and available instrumentation. The term "distinguishable feature," as used herein with respect to distinguishable labels and tags, refers to any feature of one label or tag that can be distinguished from another label or tag (e.g., mass and others described herein). In some embodiments, label composition of the distinguishable labels and tags can be selected and/or designed to result in optimal flight behavior in a mass spectrometer and to allow labels and tags to be distinguished at high multiplexing levels.

For methods used herein, a particular target (major or minor) nucleic acid species, amplicon species and/or extended oligonucleotide species often is paired with a distinguishable detectable label species, such that the detection of a particular label or tag species directly identifies the presence of and/or quantifies a particular target minor or nucleic acid species, amplicon species and/or extended oligonucleotide species in a particular composition. Accordingly, one distinguishable feature of a label species can be used, for example, to identify one target nucleic acid species in a composition, as that particular distinguishable feature corresponds to the particular target nucleic acid. Labels and tags may be attached to a nucleic acid (e.g., oligonucleotide) by any known methods and in any location (e.g., at the 5' of an oligonucleotide). Thus, reference to each particular label species as "specifically corresponding" to each particular target nucleic acid species, as used herein, refers to one label species being paired with one target species. When the presence of a label species is detected, then the presence of the target nucleic acid species associated with that label species thereby is detected and/or quantified, in certain embodiments.

The term "species," as used herein with reference to a distinguishable tag or label (collectively, "label"), refers to one label that is detectably distinguishable from another label. In certain embodiments, the number of label species, includes, but is not limited to, about 2 to about 10000 label species, about 2 to about 500,000 label species, about 2 to about 100,000, about 2 to about 50000, about 2 to about 10000, and about 2 to about 500 label species, or sometimes about 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000 or 500000 label species.

The term "mass distinguishable label" as used herein refers to a label that is distinguished by mass as a feature. A variety of mass distinguishable labels can be selected and used, such as for example a compomer, amino acid and/or a concatemer. Different lengths and/or compositions of nucleotide strings (e.g., nucleic acids, compomers), amino acid strings (e.g., peptides, polypeptides, compomers) and/or concatemers can be distinguished by mass and be used as labels. Any number of units can be utilized in a mass distinguishable label, and upper and lower limits of such units depends in part on the mass window and resolution of the system used to detect and distinguish such labels. Thus, the length and composition of mass distinguishable labels can be selected based in part on the mass window and resolution of the detector used to detect and distinguish the labels.

The term "compomer" as used herein refers to the composition of a set of monomeric units and not the particular sequence of the monomeric units. For a nucleic acid, the term "compomer" refers to the base composition of the nucleic acid with the monomeric units being bases. The number of each type of base can be denoted by $B_n$ (i.e., $A_aC_cG_gT_t$, with $A_0C_0G_0T_0$ representing an "empty" compomer or a compomer containing no bases). A natural compomer is a compomer for which all component monomeric units (e.g., bases for nucleic acids and amino acids for polypeptides) are greater than or equal to zero. In certain embodiments, at least one of A, C, G or T equals 1 or more (e.g., $A_0C_0G_1T_0$. $A_1C_0G_1T_0$, $A_2C_1G_1T_2$, $A_3C_2G_1T_5$). For purposes of comparing sequences to determine sequence variations, in the methods provided herein, "unnatural" compomers containing negative numbers of monomeric units can be generated by an algorithm utilized to process data. For polypeptides, a compomer refers to the amino acid composition of a polypeptide fragment, with the number of each type of amino acid similarly denoted. A compomer species can correspond to multiple sequences. For example, the compomer $A_2G_3$ corresponds to the sequences AGGAG, GGGAA, AAGGG, GGAGA and others. In general, there is a unique compomer corresponding to a sequence, but more than one sequence can correspond to the same compomer. In certain embodiments, one compomer species is paired with (e.g., corresponds to) one target nucleic acid species, amplicon species and/or oligonucleotide species. Different compomer species have different base compositions, and distinguishable masses, in embodiments herein (e.g., $A_0C_0G_5T_0$ and $A_0C_5G_0T_0$ are different and mass-distinguishable compomer species). In some embodiments, a set of compomer species differ by base composition and have the same length. In certain embodiments, a set of compomer species differ by base compositions and length.

A nucleotide compomer used as a mass distinguishable label can be of any length for which all compomer species can be detectably distinguished, for example about 1 to 15, 5 to 20, 1 to 30, 5 to 35, 10 to 30, 15 to 30, 20 to 35, 25 to 35, 30 to 40, 35 to 45, 40 to 50, or 25 to 50, or sometimes about 55, 60, 65, 70, 75, 80, 85, 90, 85 or 100, nucleotides in length. A peptide or polypeptide compomer used as a mass distinguishable label can be of any length for which all compomer species can be detectably distinguished, for example about 1 to 20, 10 to 30, 20 to 40, 30 to 50, 40 to 60, 50 to 70, 60 to 80, 70 to 90, or 80 to 100 amino acids in length. As noted above, the limit to the number of units in a compomer often is limited by the mass window and resolution of the detection method used to distinguish the compomer species.

The terms "concatamer" and "concatemer" are used herein synonymously (collectively "concatemer"), and refer to a molecule that contains two or more units linked to one another (e.g., often linked in series; sometimes branched in certain embodiments). A concatemer sometimes is a nucleic acid and/or an artificial polymer in some embodiments. A concatemer can include the same type of units (e.g., a homoconcatemer) in some embodiments, and sometimes a concatemer can contain different types of units (e.g., a heteroconcatemer). A concatemer can contain any type of unit(s), including nucleotide units, amino acid units, small organic molecule units (e.g., trityl), particular nucleotide sequence units, particular amino acid sequence units, and the like. A homoconcatemer of three particular sequence units ABC is ABCABCABC, in an embodiment. A concatemer can contain any number of units so long as each concatemer species can be detectably distinguished from other species. For example, a trityl concatemer species can contain about 1, 2, 3, 4, 5, 6, 7, 8, 9, 10, 11, 12, 13, 14, 15, 16, 17, 18, 19, 20, 25, 30, 35, 40, 45, 50, 55, 65, 70, 75, 80, 80, 85, 90, 95, 100, 125, 150, 175, 200, 225, 250, 275, 300, 325, 350, 375, 400, 425, 450, 475, 500, 600, 700, 800, 900 or 1000 trityl units, in some embodiments.

A distinguishable label can be released from a nucleic acid product (e.g., an extended oligonucleotide) in certain embodiments. The linkage between the distinguishable label and a nucleic acid can be of any type that can be transcribed and cleaved, cleaved and allow for detection of the released label or labels, thereby identifying and/or quantifying the nucleic acid product (e.g., U.S. patent application publication no. US20050287533A1, entitled "Target-Specific Compomers and Methods of Use," naming Ehrich et al.). Such linkages and methods for cleaving the linkages ("cleaving conditions") are known. In certain embodiments, a label can be separated from other portions of a molecule to which it is attached. In some embodiments, a label (e.g., a compomer) is cleaved from a larger string of nucleotides (e.g., extended oligonucleotides). Non-limiting examples of linkages include linkages that can be cleaved by a nuclease (e.g., ribonuclease, endonuclease); linkages that can be cleaved by a chemical; linkages that can be cleaved by physical treatment; and photocleavable linkers that can be cleaved by light (e.g., o-nitrobenzyl, 6-n itroveratryloxycarbonyl, 2-nitrobenzyl group). Photocleavable linkers provide an advantage when using a detection system that emits light (e.g., matrix-assisted laser desorption ionization (MALDI) mass spectrometry involves the laser emission of light), as cleavage and detection are combined and occur in a single step.

In certain embodiments, a label can be part of a larger unit, and can be separated from that unit prior to detection. For example, in certain embodiments, a label is a set of contiguous nucleotides in a larger nucleotide sequence, and the label is cleaved from the larger nucleotide sequence. In such embodiments, the label often is located at one terminus of the nucleotide sequence or the nucleic acid in which it resides. In some embodiments, the label, or a precursor thereof, resides in a transcription cassette that includes a promoter sequence operatively linked with the precursor sequence that encodes the label. In the latter embodiments, the promoter sometimes is a RNA polymerase-recruiting promoter that generates an RNA that includes or consists of the label. An RNA that includes a label can be cleaved to release the label prior to detection (e.g., with an RNase).

In certain embodiments, a distinguishable label or tag is not cleaved from an extended oligonucleotide, and in some embodiments, the distinguishable label or tag comprises a capture agent. In certain embodiments, detecting a distinguishable feature includes detecting the presence or absence of an extended oligonucleotide, and in some embodiments an extended oligonucleotide includes a capture agent.

Detection and Degree of Multiplexing

The term "detection" of a label as used herein refers to identification of a label species. Any suitable detection device can be used to distinguish label species in a sample. Detection devices suitable for detecting mass distinguishable labels, include, without limitation, certain mass spectrometers and gel electrophoresis devices. Examples of mass spectrometry formats include, without limitation, Matrix-Assisted Laser Desorption/Ionization Time-of-Flight (MALDI-TOF) Mass Spectrometry (MS), MALDI orthogonal TOF MS (OTOF MS; two dimensional), Laser Desorption Mass Spectrometry (LDMS), Electrospray (ES) MS, Ion Cyclotron Resonance (ICR) MS, and Fourier Transform MS. Methods described herein are readily applicable to mass spectrometry formats in which analyte is volatized and ionized ("ionization MS," e.g., MALDI-TOF MS, LDMS, ESMS, linear TOF, OTOF). Orthogonal ion extraction MALDI-TOF and axial MALDI-TOF can give rise to relatively high resolution, and thereby, relatively high levels of multiplexing. Detection devices suitable for detecting light-emitting, light absorbing and/or light-scattering labels, include, without limitation, certain light detectors and photodetectors (e.g., for fluorescence, chemiluminescence, absorbtion, and/or light scattering labels).

Methods provided herein allow for high-throughput detection or discovery of a plurality of minor nucleic acid species present in a sample or combination of samples containing one or a plurality of major nucleic acid species. Multiplexing provides an advantage that a plurality of minor nucleic acid species (e.g., some having different sequence variations) can be identified in as few as a single mass spectrum or other detection system such as fluorescence or electric signal, as compared to having to perform a separate mass spectrometry or other analysis for each individual minor nucleic acid species. Methods provided herein lend themselves to high-throughput, highly-automated processes for analyzing sequence variations with high speed and accuracy, in some embodiments. In some embodiments, methods herein may be multiplexed at high levels in a single reaction. Multiplexing is applicable when the genotype at a polymorphic locus is not known, and in some embodiments, the genotype at a locus is known.

In certain embodiments, the number of target (minor and/or major) nucleic acid species multiplexed include, without limitation, about 2 to 1,000 species, and sometimes about 1-3, 3-5, 5-7, 7-9, 9-11, 11-13, 13-15, 15-17, 17-19, 19-21, 21-23, 23-25, 25-27, 27-29, 29-31, 31-33, 33-35, 35-37, 37-39, 39-41, 41-43, 43-45, 45-47, 47-49, 49-51, 51-53, 53-55, 55-57, 57-59, 59-61, 61-63, 63-65, 67-69, 69-71, 71-73, 73-75, 75-77, 77-79, 79-81, 81-83, 83-85, 85-87, 87-89, 89-91, 91-93, 93-95, 95-97, 97-101, 101-103, 103-105, 105-107, 107-109, 109-111, 111-113, 113-115, 115-117, 117-119, 121-123, 123-125, 125-127, 127-129, 129-131, 131-133, 133-135, 135-137, 137-139, 139-141, 141-143, 143-145, 145-147, 147-149, 149-151, 151-153, 153-155, 155-157, 157-159, 159-161, 161-163, 163-165, 165-167, 167-169, 169-171, 171-173, 173-175, 175-177, 177-179, 179-181, 181-183, 183-185, 185-187, 187-189, 189-191, 191-193, 193-195, 195-197, 197-199, 199-201, 201-203, 203-205, 205-207, 207-209, 209-211, 211-213, 213-215, 215-217, 217-219, 219-221, 221-223, 223-225, 225-227, 227-229, 229-231, 231-233, 233-235, 235-237, 237-239, 239-241, 241-243, 243-245, 245-247, 247-249, 249-251, 251-253, 253-255, 255-257, 257-259, 259-261, 261-263, 263-265, 265-267, 267-269, 269-271, 271-273, 273-275, 275-277, 277-279, 279-281, 281-283, 283-285, 285-287, 287-289, 289-291, 291-293, 293-295, 295-297, 297-299, 299-301, 301-303, 303-305, 305-307, 307-309, 309-311, 311-313, 313-315, 315-317, 317-319, 319-321, 321-323, 323-325, 325-327, 327-329, 329-331, 331-333, 333-335, 335-337, 337-339, 339-341, 341-343, 343-345, 345-347, 347-349, 349-351, 351-353, 353-355, 355-357, 357-359, 359-361, 361-363, 363-365, 365-367, 367-369, 369-371, 371-373, 373-375, 375-377, 377-379, 379-381, 381-383, 383-385, 385-387, 387-389, 389-391, 391-393, 393-395, 395-397, 397-401, 401-403, 403-405, 405-407, 407-409, 409-411, 411-413, 413-415, 415-417, 417-419, 419-421, 421-423, 423-425, 425-427, 427-429, 429-431, 431-433, 433-435, 435-437, 437-439, 439-441, 441-443, 443-445, 445-447, 447-449, 449-451, 451-453, 453-455, 455-457, 457-459, 459-461, 461-463, 463-465, 465-467, 467-469, 469-471, 471-473, 473-475, 475-477, 477-479, 479-481, 481-483, 483-485, 485-487, 487-489, 489-491, 491-493, 493-495, 495-497, 497-501 species or more.

Design methods for achieving resolved mass spectra with multiplexed assays can include primer and oligonucleotide design methods, relative concentrations of reagents such as chain terminating reagents, choice of detection labels and other reaction design methods. For primer and oligonucleotide design in multiplexed assays, the same general guidelines for primer design applies for uniplexed reactions, such as avoiding false priming and primer dimers, only more primers are involved for multiplex reactions. In addition, for analysis by mass spectrometry, analyte peaks in the mass spectra for one assay are sufficiently resolved from a product of any assay with which that assay is multiplexed, including pausing peaks and any other by-product peaks. Also, analyte peaks optimally fall within a user-specified mass window, for example, within a range of 5,000-8,500 Da. Extension oligonucleotides can be designed with respect to target sequences of a given SNP strand, in some embodiments. In such embodiments, the length often is between limits that can be, for example, user-specified (e.g., 17 to 24 bases or 17-26 bases) and often do not contain bases that are uncertain in the target sequence. Hybridization strength sometimes is gauged by calculating the sequence-dependent melting (or hybridization/dissociation) temperature, $T_m$. A particular primer choice may be disallowed, or penalized relative to other choices of primers, because of its hairpin potential, false priming potential, primer-dimer potential, low complexity regions, and problematic subsequences such as GGGG. Methods and software for designing extension oligonucleotides (e.g., according to these criteria) are known, and include, for example, SpectroDESIGNER (Sequenom).

As used herein, the term "call rate" or "calling rate" refers to the number of calls (e.g., genotypes or mutants determined) obtained relative to the number of calls attempted to be obtained. In other words, for a 12-plex reaction, if 10 genotypes are ultimately determined from conducting methods provided herein, then 10 calls have been obtained with a call rate of 10/12. Different events can lead to failure of a particular attempted assay, and lead to a call rate lower than 100%. Occasionally, in the case of a mix of dNTPs and ddNTPs for termination, inappropriate extension products can occur by pausing of a polymerase after incorporation of one non-terminating nucleotide (i.e., dNTP), resulting in a prematurely terminated extension primer, for example. The mass difference between this falsely terminated and a correctly terminated primer mass extension reaction at the polymorphic site sometimes is too small to resolve consistently and can lead to miscalls if an inappropriate termination mix is used. The mass differences between a correct termination and a false termination (i.e., one caused by pausing) as well between a correct termination and salt adducts as well as a correct termination and an unspecific incorporation often is maximized to reduce the number of miscalls.

Multiplex assay accuracy may be determined by assessing the number of calls obtained (e.g., correctly or accurately assessed) and/or the number of false positive and/or false negative events in one or more assays. Accuracy also may be assessed by comparison with the accuracy of corresponding uniplex assays for each of the targets assessed in the multiplex assay. In certain embodiments, one or more methods may be used to determine a call rate. For example, a manual method may be utilized in conjunction with an automated or computer method for making calls, and in some embodiments, the rates for each method may be summed to calculate an overall call rate. In certain embodiments, accuracy or call rates, when multiplexing two or more target nucleic acids (minor and/or major nucleic acid species), e.g., fifty or more target nucleic acids, can be about 99% or greater, 98%, 97%, 96%, 95%, 94%, 93%, 92%, 91%, 90%, 89%, 87-88%, 85-86%, 83-84%, 81-82%, 80%, 78-79% or 76-77%, for example. In some embodiments, a call rate for each target species in a multiplex assay that includes about 2 to 200 target species is greater than or equal to 80% or more (e.g., 81%, 82%, 83%, 84%, 85%, 86%, 87%, 88%, 89%, 90%, 91%, 92%, 93%, 94%, 95%, 96%, 97%, 98%, 99% or greater).

In certain embodiments the error rate may be determined based on the call rate or rate of accuracy. For example, the error rate may be the number of calls made in error. In some embodiments, for example, the error rate may be 100% less the call rate or rate of accuracy. The error rate may also be referred to as the "fail rate." Identification of false positives and/or false negatives can readjust both the call and error rates. In certain embodiments running more assays can also help in identifying false positives and/or false negatives, thereby adjusting the call and/or error rates. In certain embodiments, error rates, when multiplexing two or more target nucleic acids that are major and/or minor nucleic acid species, e.g., fifty or more target nucleic acid species, can be about 1% or less, 2%, 3%, 4,%, 5%, 6%, 7%, 8%, 9%, 10%, 11%, 12%, 13%, 14%, 15%, 16%, 17%, 18%, 19%, 20%, 21%, 22%, 23%, 24% or 25%, for example.

Applications

Following are examples of non-limiting applications of multiplex technology described herein.

1. Detection of Sequence Variations (e.g. Genetic Variants)

Provided are improved methods for identifying the genomic basis of disease and markers thereof. The sequence variation (e.g. genetic variant) candidates that can be identified by the methods provided herein include sequences containing sequence variations that are polymorphisms. Polymorphisms include both naturally occurring, somatic sequence variations and those arising from mutation. Polymorphisms include but are not limited to: sequence microvariants where one or more nucleotides in a localized region vary from individual to individual, insertions and deletions which can vary in size from one nucleotide to millions of bases, and microsatellite or nucleotide repeats which vary by numbers of repeats. Nucleotide repeats include homogeneous repeats such as dinucleotide, trinucleotide, tetranucleotide or larger repeats, where the same sequence in repeated multiple times, and also heteronucleotide repeats where sequence motifs are found to repeat. For a given locus the number of nucleotide repeats can vary depending on the individual.

A polymorphic marker or site is the locus at which divergence occurs. Such a site can be as small as one base pair (an SNP). Polymorphic markers include, but are not limited to, restriction fragment length polymorphisms (RFLPs), variable number of tandem repeats (VNTR's), hypervariable regions, minisatellites, dinucleotide repeats, trinucleotide repeats, tetranucleotide repeats and other repeating patterns, simple sequence repeats and insertional elements, such as Alu. Polymorphic forms also are manifested as different Mendelian alleles for a gene. Polymorphisms can be observed by differences in proteins, protein modifications, RNA expression modification, DNA and RNA methylation, regulatory factors that alter gene expression and DNA replication, and any other manifestation of alterations in genomic nucleic acid or organelle nucleic acids.

Furthermore, numerous genes have polymorphic regions. Since individuals have any one of several allelic variants of a polymorphic region, individuals can be identified based on the type of allelic variants of polymorphic regions of genes. This can be used, for example, for forensic purposes. In other situations, it is crucial to know the identity of allelic variants that an individual has. For example, allelic differences in certain genes, for example, major histocompatibility complex (MHC) genes, are involved in graft rejection or graft versus host disease in bone marrow transportation. Accordingly, it is highly desirable to develop rapid, sensitive, and accurate methods for determining the identity of allelic variants of polymorphic regions of genes or genetic lesions. A method or a kit as provided herein can be used to genotype a subject by determining the identity of one or more allelic variants of one or more polymorphic regions in one or more genes or chromosomes of the subject. Genotyping a subject using a method as provided herein can be used for forensic or identity testing purposes and the polymorphic regions can be present in mitochondrial genes or can be short tandem repeats.

Single nucleotide polymorphisms (SNPs) are generally biallelic systems, that is, there are two alleles that an individual can have for any particular marker. This means that the information content per SNP marker is relatively low when compared to microsatellite markers, which can have upwards of 10 alleles. SNPs also tend to be very population-specific; a marker that is polymorphic in one population cannot be very polymorphic in another. SNPs, found approximately every kilobase (see Wang et al. (1998) Science 280:1077-1082), offer the potential for generating very high density genetic maps, which will be extremely useful for developing haplotyping systems for genes or regions of interest, and because of the nature of SNPs, they can in fact be the polymorphisms associated with the disease phenotypes under study. The low mutation rate of SNPs also makes them excellent markers for studying complex genetic traits.

Much of the focus of genomics has been on the identification of SNPs, which are important for a variety of reasons. They allow indirect testing (association of haplotypes) and direct testing (functional variants). They are the most abundant and stable genetic markers. Common diseases are best explained by common genetic alterations, and the natural variation in the human population aids in understanding disease, therapy and environmental interactions.

Sensitive detection of somatic mutations is especially valuable to the cancer research community whose interest is the identification of genetic determinants for the initiation and proliferation of tumors. The information gained from a sensitive approach can also be used for profiling mutations to predict patient outcomes and inform a relevant treatment option. In some embodiments, a sensitive detection method, that can detect a genetic variant that represents less than or equal to 5% of its counterpart wild type sequence, is needed. In some embodiments, a detection method that can detect less than or equal to 1% of wild type is implemented. In some embodiments, a detection method that can detect less than or equal to 5%, 4%, 3%, 2%, 1%, 0.8%, 0.75%, 0.5%, 0.05%, or 0.01% of wild type is implemented. Additionally, within pre-natal diagnostics, this type of method could elucidate paternally derived mutations in utero.

In some embodiments, allelic analysis can be performed by generating extended oligonucleotides from nucleic acid targets carrying one or more somatic mutations (e.g., SNPs, disease markers, the like and combinations thereof) of interest. Detecting the presence or absence of a released, extended oligonucleotide representing an allele carrying a somatic mutation can be utilized as a rapid method of screening for the presence or absence of a particular mutation in a target population, in some embodiments. In certain embodiments involving generating an extended oligonucleotide from a mutant allele, the extended oligonucleotide can be detected as the appropriate mutant allele gives rise to an extended oligonucleotide product.

2. Identifying Disease Markers

Provided herein are methods for the rapid and accurate identification of sequence variations that are genetic markers of disease, which can be used to diagnose or determine the prognosis of a disease. Diseases characterized by genetic markers can include, but are not limited to, atherosclerosis, obesity, diabetes, autoimmune disorders, and cancer. Diseases in all organisms have a genetic component, whether inherited or resulting from the body's response to environmental stresses, such as viruses and toxins. The ultimate goal of ongoing genomic research is to use this information to develop new ways to identify, treat and potentially cure these diseases. The first step has been to screen disease tissue and identify genomic changes at the level of individual samples. The identification of these "disease" markers is dependent on the ability to detect changes in genomic markers in order to identify errant genes or sequence variants. Genomic markers (all genetic loci including single nucleotide polymorphisms (SNPs), microsatellites and other noncoding genomic regions, tandem repeats, introns and exons) can be used for the identification of all organisms, including humans. These markers provide a way to not only identify populations but also allow stratification of populations according to their response to disease, drug treatment, resistance to environmental agents, and other factors. A disease marker sometimes is a mutation, and can be a relatively rare allele such as, for example, a somatic mutation against the background of a wild type allele (e.g., cancer tissue versus normal tissue, mutant viral type versus normal viral type (e.g. HIV)), in some embodiments. In some embodiments the rare allele or mutation represents less than 5%, 4%, 3%, 2%, 1%, 0.8%, 0.75%, 0.1%, 0.05%, or 0.01% of the wild type. In some embodiment, the rare allele or mutation can represent less than 1% of the wild type.

3. Microbial Identification

Provided herein is a process or method for identifying genera, species, strains, clones or subtypes of microorganisms and viruses. The microorganism(s) and viruses are selected from a variety of organisms including, but not limited to, bacteria, fungi, protozoa, ciliates, and viruses. The microorganisms are not limited to a particular genus, species, strain, subtype or serotype or any other classification. The microorganisms and viruses can be identified by determining sequence variations in a target microorganism sequence relative to one or more reference sequences or samples. The reference sequence(s) can be obtained from, for example, other microorganisms from the same or different genus, species strain or serotype or any other classification, or from a host prokaryotic or eukaryotic organism or any mixed population.

Identification and typing of pathogens (e.g., bacterial or viral) is critical in the clinical management of infectious diseases. Precise identity of a microbe is used not only to differentiate a disease state from a healthy state, but is also fundamental to determining the source of the infection and its spread and whether and which antibiotics or other antimicrobial therapies are most suitable for treatment. In addition treatment can be monitored. Traditional methods of pathogen typing have used a variety of phenotypic features, including growth characteristics, color, cell or colony morphology, antibiotic susceptibility, staining, smell, serotyping, biochemical typing and reactivity with specific antibodies to identify microbes (e.g., bacteria). All of these methods require culture of the suspected pathogen, which suffers from a number of serious shortcomings, including high material and labor costs, danger of worker exposure, false positives due to mishandling and false negatives due to low numbers of viable cells or due to the fastidious culture requirements of many pathogens. In addition, culture methods require a relatively long time to achieve diagnosis, and because of the potentially life-threatening nature of such infections, antimicrobial therapy is often started before the results can be obtained. Some organisms cannot be maintained in culture or exhibit prohibitively slow growth rates (e.g., up to 6-8 weeks for *Mycobacterium tuberculosis*).

In many cases, the pathogens are present in minor amounts and/or are very similar to the organisms that make up the normal flora, and can be indistinguishable from the innocuous strains by the methods cited above. In these cases, determination of the presence of the pathogenic strain can require the higher resolution afforded by the molecular typing methods provided herein.

4. Detecting the Presence of Viral or Bacterial Nucleic Acid Sequences Indicative of an Infection The methods provided herein can be used to determine the presence of viral or bacterial nucleic acid sequences indicative of an infection by identifying sequence variations that are present in the viral or bacterial nucleic acid sequences relative to one or more reference sequences. The reference sequence(s) can include, but are not limited to, sequences obtained from an infectious organism, related non-infectious organisms, or sequences from host organisms. Viruses, bacteria, fungi and other infectious organisms contain distinct nucleic acid sequences, including sequence variants, which are different from the sequences contained in the host cell. A target DNA sequence can be part of a foreign genetic sequence such as the genome of an invading microorganism, including, for example, bacteria and their phages, viruses, fungi, protozoa, and the like. The processes provided herein are particularly applicable for distinguishing between different variants or strains of a microorganism (e.g., pathogenic, less pathogenic, resistant versus non-resistant and the like) in order, for example, to choose an appropriate therapeutic intervention. Examples of disease-causing viruses that infect humans and animals and that can be detected by a disclosed process include but are not limited to Retroviridae (e.g., human immunodeficiency viruses such as HIV-1 (also referred to as HTLV-III, LAV or HTLV-III/LAV; Ratner et al., Nature, 313:227-284 (1985); Wain Hobson et al., Cell, 40:9-17 (1985), HIV-2 (Guyader et al., Nature, 328:662-669 (1987); European Patent Publication No. 0 269 520; Chakrabarti et al., Nature, 328:543-547 (1987); European Patent Application No. 0 655 501), and other isolates such as HIV-LP (International Publication No. WO 94/00562); Picornaviridae (e.g., polioviruses, hepatitis A virus, (Gust et al., Intervirology, 20:1-7 (1983)); enteroviruses, human coxsackie viruses, rhinoviruses, echoviruses); Calcivirdae (e.g. strains that cause gastroenteritis); Togaviridae (e.g., equine encephalitis viruses, rubella viruses); Flaviridae (e.g., dengue viruses, encephalitis viruses, yellow fever viruses); Coronaviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses); Bungaviridae (e.g., Hantaan viruses, bunga viruses, phleboviruses and Nairo viruses); Arenaviridae (hemorrhagic fever viruses); Reoviridae (e.g., reoviruses, orbiviruses and rotaviruses); Birnaviridae; Hepadnaviridae (Hepatitis B virus); Parvoviridae (parvoviruses); Parvoviridae (most adenoviruses); Papovaviridae (papilloma viruses, polyoma viruses); Adenoviridae (most adenoviruses); Herpesviridae (herpes simplex virus type 1 (HSV-1) and HSV-2, varicella zoster virus, cytomegalovirus, herpes viruses; Poxviridae (variola viruses, vaccinia viruses, pox viruses); Iridoviridae (e.g., African swine fever virus); and unclassified viruses (e.g., the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted, i.e., Hepatitis C); Norwalk and related viruses, and astroviruses.

Examples of infectious bacteria include but are not limited to *Helicobacter* pyloris, Borelia *burgdorferi, Legionella* pneumophilia, Mycobacteria sp. (e.g. *M. tuberculosis, M. avium, M. intracellulare, M. kansaii, M. gordonae*), *Salmonella, Staphylococcus aureus, Neisseria gonorrheae, Neisseria meningitidis, Listeria monocytogenes, Streptococcus pyogenes* (Group A *Streptococcus*), *Streptococcus agalactiae* (Group B *Streptococcus*), *Streptococcus* sp. (*viridans* group), *Streptococcus faecalis, Streptococcus bovis, Streptococcus* sp. (anaerobic species), *Streptococcus pneumoniae*, pathogenic *Campylobacter* sp., *Enterococcus* sp., *Haemophilus influenzae, Bacillus anthracis, Corynebacterium diphtheriae, Corynebacterium* sp., Erysipelothrix rhusiopathiae, *Clostridium perfringens, Clostridium tetani, Escherichia coli, Enterobacter aerogenes, Klebsiella pneumoniae, Pasteurella multocida, Bacteroides* sp., *Fusobacterium nucleatum, Streptobacillus moniliformis, Treponema pallidium, Treponema* pertenue, Leptospira, and *Actinomyces* israelli and any variants including antibiotic resistance variants Examples of infectious fungi include but are not limited to *Cryptococcus neoformans, Histoplasma capsulatum, Coccidioides immitis, Blastomyces dermatitidis, Chlamydia trachomatis, Candida albicans*. Other infectious organisms include protists such as *Plasmodium falciparum* and *Toxoplasma gondii.*

Antibiotic Profiling

Methods provided herein can improve the speed and accuracy of detection of nucleotide changes involved in drug resistance, including antibiotic resistance. Genetic loci involved in resistance to isoniazid, rifampin, streptomycin, fluoroquinolones, and ethionamide have been identified [Heym et al., Lancet 344:293 (1994) and Morris et al., J. Infect. Dis. 171:954 (1995)]. A combination of isoniazid (inh) and rifampin (rif) along with pyrazinamide and ethambutol or streptomycin, is routinely used as the first line of attack against confirmed cases of *M. tuberculosis* [Banerjee et al., Science 263:227 (1994)]. The increasing incidence of such resistant strains necessitates the development of rapid assays to detect them and thereby reduce the expense and community health hazards of pursuing ineffective, and possibly detrimental, treatments. The identification of some of the genetic loci involved in drug resistance has facilitated the adoption of mutation detection technologies for rapid screening of nucleotide changes that result in drug resistance. In addition, the technology facilitates treatment monitoring and tracking or microbial population structures as well as surveillance monitoring during treatment. In addition, correlations and surveillance monitoring of mixed populations can be performed.

6. Haplotyping

The methods provided herein can be used to detect haplotypes. In any diploid cell, there are two haplotypes at any gene or other chromosomal segment that contain at least one distinguishing variance. In many well-studied genetic systems, haplotypes are more powerfully correlated with phenotypes than single nucleotide variations. Thus, the determination of haplotypes is valuable for understanding the genetic basis of a variety of phenotypes including disease predisposition or susceptibility, response to therapeutic interventions, and other phenotypes of interest in medicine, animal husbandry, and agriculture.

Haplotyping procedures as provided herein permit the selection of a portion of sequence from one of an individual's two homologous chromosomes and to genotype linked SNPs on that portion of sequence. The direct resolution of haplotypes can yield increased information content, improving the diagnosis of any linked disease genes or identifying linkages associated with those diseases.

7. Microsatellites

Methods provided herein allow for rapid, unambiguous detection of microsatellite sequence variations. Microsatellites (sometimes referred to as variable number of tandem repeats or VNTRs) are short tandemly repeated nucleotide units of one to seven or more bases, the most prominent among them being di-, tri-, and tetranucleotide repeats. Microsatellites are present every 100,000 bp in genomic DNA (J. L. Weber and P. E. Can, Am. J. Hum. Genet. 44, 388 (1989); J. Weissenbach et al., Nature 359, 794 (1992)). CA dinucleotide repeats, for example, make up about of the human extra-mitochondrial genome; CT and AG repeats together make up about 0.2%. CG repeats are rare, most probably due to the regulatory function of CpG islands. Microsatellites are highly polymorphic with respect to length and widely distributed over the whole genome with a main abundance in non-coding sequences, and their function within the genome is unknown. Microsatellites can be important in forensic applications, as a population will maintain a variety of microsatellites characteristic for that population and distinct from other populations which do not interbreed.

Many changes within microsatellites can be silent, but some can lead to significant alterations in gene products or expression levels. For example, trinucleotide repeats found in the coding regions of genes are affected in some tumors (C. T. Caskey et al., Science 256, 784 (1992) and alteration of the microsatellites can result in a genetic instability that results in a predisposition to cancer (P. J. McKinnen, Hum. Genet. 1 75, 197 (1987); J. German et al., Clin. Genet. 35, 57 (1989)).

8. Short Tandem Repeats

The methods provided herein can be used to identify short tandem repeat (STR) regions in some target sequences of the human genome relative to, for example, reference sequences in the human genome that do not contain STR regions. STR regions are polymorphic regions that are not related to any disease or condition. Many loci in the human genome contain a polymorphic short tandem repeat (STR) region. STR loci contain short, repetitive sequence elements of 3 to 7 base pairs in length. It is estimated that there are 200,000 expected trimeric and tetrameric STRs, which are present as frequently as once every 15 kb in the human genome (see, e.g., International PCT application No. WO 9213969 A1, Edwards et al., Nucl. Acids Res. 19:4791 (1991); Beckmann et al. (1992) Genomics 12:627-631). Nearly half of these STR loci are polymorphic, providing a rich source of genetic markers. Variation in the number of repeat units at a particular locus is responsible for the observed sequence variations reminiscent of variable nucleotide tandem repeat (VNTR) loci (Nakamura et al. (1987) Science 235:1616-1622); and minisatellite loci (Jeffreys et al. (1985) Nature 314:67-73), which contain longer repeat units, and microsatellite or dinucleotide repeat loci (Luty et al. (1991) Nucleic Acids Res. 19:4308; Litt et al. (1990) Nucleic Acids Res. 18:4301; Litt et al. (1990) Nucleic Acids Res. 18:5921; Luty et al. (1990) Am. J. Hum. Genet. 46:776-783; Tautz (1989) Nucl. Acids Res. 17:6463-6471; Weber et al. (1989) Am. J. Hum. Genet. 44:388-396; Beckmann et al. (1992) Genomics 12:627-631). VNTR typing is a very established tool in microbial typing e.g. *M. tuberculosis* (MIRU typing).

Examples of STR loci include, but are not limited to, pentanucleotide repeats in the human CD4 locus (Edwards et al., Nucl. Acids Res. 19:4791 (1991)); tetranucleotide repeats in the human aromatase cytochrome P-450 gene (CYP19; Polymeropoulos et al., Nucl. Acids Res. 19:195 (1991)); tetranucleotide repeats in the human coagulation factor XIII A subunit gene (F13A1; Polymeropoulos et al., Nucl. Acids Res. 19:4306 (1991)); tetranucleotide repeats in the F13B locus (Nishimura et al., Nucl. Acids Res. 20:1167 (1992)); tetranucleotide repeats in the human c-les/fps, proto-oncogene (FES; Polymeropoulos et al., Nucl. Acids Res. 19:4018 (1991)); tetranucleotide repeats in the LFL gene (Zuliani et al., Nucl. Acids Res. 18:4958 (1990)); trinucleotide repeat sequence variations at the human pancreatic phospholipase A-2 gene (PLA2; Polymeropoulos et al., Nucl. Acids Res. 18:7468 (1990)); tetranucleotide repeat sequence variations in the VWF gene (Ploos et al., Nucl. Acids Res. 18:4957 (1990)); and tetranucleotide repeats in the human thyroid peroxidase (hTPO) locus (Anker et al., Hum. Mol. Genet. 1:137 (1992)).

9. Organism Identification

Polymorphic STR loci and other polymorphic regions of genes are sequence variations that are extremely useful markers for human identification, paternity and maternity testing, genetic mapping, immigration and inheritance disputes, zygosity testing in twins, tests for inbreeding in humans, quality control of human cultured cells, identification of human remains, and testing of semen samples, blood stains, microbes and other material in forensic medicine. Such loci also are useful markers in commercial animal breeding and pedigree analysis and in commercial plant breeding. Traits of economic importance in plant crops and animals can be identified through linkage analysis using polymorphic DNA markers. Efficient and accurate methods for determining the identity of such loci are provided herein.

10. Detecting Allelic Variation

The methods provided herein allow for high-throughput, fast and accurate detection of allelic variants. Studies of allelic variation involve not only detection of a specific sequence in a complex background, but also the discrimination between sequences with few, or single, nucleotide differences. One method for the detection of allele-specific variants by PCR is based upon the fact that it is difficult for Taq polymerase to synthesize a DNA strand when there is a mismatch between the template strand and the 3' end of the primer. An allele-specific variant can be detected by the use of a primer that is perfectly matched with only one of the possible alleles; the mismatch to the other allele acts to prevent the extension of the primer, thereby preventing the amplification of that sequence. The methods herein also are applicable to association studies, copy number variations, detection of disease marker and SNP sets for typing and the like.

11. Determining Allelic Frequency

The methods herein described are valuable for identifying one or more genetic markers whose frequency changes within the population as a function of age, ethnic group, sex or some other criteria. For example, the age-dependent distribution of ApoE genotypes is known in the art (see, e.g., Schechter et al. (1994) Nature Genetics 6:29-32). The frequencies of sequence variations known to be associated at some level with disease can also be used to detect or monitor progression of a disease state. For example, the N291S polymorphism (N291S) of the Lipoprotein Lipase gene, which results in a substitution of a serine for an asparagine at amino acid codon 291, leads to reduced levels of high density lipoprotein cholesterol (HDL-C) that is associated with an increased risk of males for arteriosclerosis and in particular myocardial infarction (see, Reymer et al. (1995) Nature Genetics 10:28-34). In addition, determining changes in allelic frequency can allow the identification of previously unknown sequence variations and ultimately a gene or pathway involved in the onset and progression of disease.

12. Epigenetics

The methods provided herein can be used to study variations in a target nucleic acid or protein relative to a reference nucleic acid or protein that are not based on sequence, e.g., the identity of bases or amino acids that are the naturally occurring monomeric units of the nucleic acid or protein. For example, methods provided herein can be used to recognize differences in sequence-independent features such as methylation patterns, the presence of modified bases or amino acids, or differences in higher order structure between the target molecule and the reference molecule, to generate fragments that are cleaved at sequence-independent sites. Epigenetics is the study of the inheritance of information based on differences in gene expression rather than differences in gene sequence. Epigenetic changes refer to mitotically and/or meiotically heritable changes in gene function or changes in higher order nucleic acid structure that cannot be explained by changes in nucleic acid sequence. Examples of features that are subject to epigenetic variation or change include, but are not limited to, DNA methylation patterns in animals, histone modification and the Polycomb-trithorax group (Pc-G/tx) protein complexes (see, e.g., Bird, A., Genes Dev., 16:6-21 (2002)).

Epigenetic changes usually, although not necessarily, lead to changes in gene expression that are usually, although not necessarily, inheritable. For example, as discussed further below, changes in methylation patterns is an early event in cancer and other disease development and progression. In many cancers, certain genes are inappropriately switched off or switched on due to aberrant methylation. The ability of methylation patterns to repress or activate transcription can be inherited. The Pc-G/trx protein complexes, like methylation, can repress transcription in a heritable fashion. The Pc-G/trx multiprotein assembly is targeted to specific regions of the genome where it effectively freezes the embryonic gene expression status of a gene, whether the gene is active or inactive, and propagates that state stably through development. The ability of the Pc-G/trx group of proteins to target and bind to a genome affects only the level of expression of the genes contained in the genome, and not the properties of the gene products. The methods provided herein can be used with specific cleavage reagents or specific extension reactions that identify variations in a target sequence relative to a reference sequence that are based on sequence-independent changes, such as epigenetic changes.

13. Methylation Patterns

The methods provided herein can be used to detect sequence variations that are epigenetic changes in the target sequence, such as a change in methylation patterns in the target sequence. Analysis of cellular methylation is an emerging research discipline. The covalent addition of methyl groups to cytosine is primarily present at CpG dinucleotides (microsatellites). Although the function of CpG islands not located in promoter regions remains to be explored, CpG islands in promoter regions are of special interest because their methylation status regulates the transcription and expression of the associated gene. Methylation of promoter regions leads to silencing of gene expression. This silencing is permanent and continues through the process of mitosis. Due to its significant role in gene expression, DNA methylation has an impact on developmental processes, imprinting and X-chromosome inactivation as well as tumor genesis, aging, and also suppression of parasitic DNA. Methylation is thought to be involved in the cancerogenesis of many widespread tumors, such as lung, breast, and colon cancer, and in leukemia. There is also a relation between methylation and protein dysfunctions (long Q-T syndrome) or metabolic diseases (transient neonatal diabetes, type 2 diabetes).

Bisulfite treatment of genomic DNA can be utilized to analyze positions of methylated cytosine residues within the DNA. Treating nucleic acids with bisulfite deaminates cytosine residues to uracil residues, while methylated cytosine remains unmodified. Thus, by comparing the sequence of a target nucleic acid that is not treated with bisulfite with the sequence of the nucleic acid that is treated with bisulfite in the methods provided herein, the degree of methylation in a nucleic acid as well as the positions where cytosine is methylated can be deduced.

Methylation analysis via restriction endonuclease reaction is made possible by using restriction enzymes which have methylation-specific recognition sites, such as HpaII and MSPI. The basic principle is that certain enzymes are blocked by methylated cytosine in the recognition sequence. Once this differentiation is accomplished, subsequent analysis of the resulting fragments can be performed using the methods as provided herein.

These methods can be used together in combined bisulfite restriction analysis (COBRA). Treatment with bisulfite causes a loss in BstUI recognition site in amplified PCR product, which causes a new detectable fragment to appear on analysis compared to untreated sample. Methods provided herein can be used in conjunction with specific cleavage of methylation sites to provide rapid, reliable information on the methylation patterns in a target nucleic acid sequence.

14. Resequencing

The dramatically growing amount of available genomic sequence information from various organisms increases the need for technologies allowing large-scale comparative sequence analysis to correlate sequence information to function, phenotype, or identity. The application of such technologies for comparative sequence analysis can be widespread, including SNP discovery and sequence-specific identification of pathogens. Therefore, resequencing and high-throughput mutation screening technologies are critical to the identification of mutations underlying disease, as well as the genetic variability underlying differential drug response.

Several approaches have been developed in order to satisfy these needs. Current technology for high-throughput DNA sequencing includes DNA sequencers using electrophoresis and laser-induced fluorescence detection. Electrophoresis-based sequencing methods have inherent limitations for detecting heterozygotes and are compromised by GC compressions. Thus a DNA sequencing platform that produces digital data without using electrophoresis can overcome these problems. Matrix-assisted laser desorption/ionization time-of-flight mass spectrometry (MALDI-TOF MS) measures nucleic acid fragments with digital data output. Methods provided herein allow for high-throughput, high speed and high accuracy in the detection of sequence identity and sequence variations relative to a reference sequence. This approach makes it possible to routinely use MALDI-TOF MS sequencing for accurate mutation detection, such as screening for founder mutations in BRCA1 and BRCA2, which are linked to the development of breast cancer.

15. Disease Outbreak Monitoring

In times of global transportation and travel outbreaks of pathogenic endemics require close monitoring to prevent their worldwide spread and enable control. DNA based typing by high-throughput technologies enable a rapid sample throughput in a comparatively short time, as required in an outbreak situation (e.g. monitoring in the hospital environment, early warning systems). Monitoring is dependent of the microbial marker region used, but can facilitate monitoring to the genus, species, strain or subtype specific level. Such approaches can be useful in biodefense, in clinical and pharmaceutical monitoring and metagenomics applications (e.g. analysis of gut flora). Such monitoring of treatment progress or failure is described in U.S. Pat. Nos. 7,255,992, 7,217,510, 7,226,739 and 7,108,974, which are incorporated by reference herein.

16. Vaccine Quality Control and Production Clone Quality Control

Methods provided herein can be used to control the identity of recombinant production clones (not limited to vaccines), which can be vaccines or e.g. insulin or any other production clone or biological or medical product.

17. Microbial Monitoring in Pharmacology for Production Control and Quality

Methods provided herein can be used to control the quality of pharmacological products by, for example, detecting the presence or absence of certain microorganism target nucleic acids in such products.

Kits

In some embodiments, provided are kits for carrying out methods described herein. Kits often comprise one or more containers that contain one or more components described herein. A kit comprises one or more components in any number of separate containers, packets, tubes, vials, multi-well plates and the like, or components may be combined in various combinations in such containers. One or more of the following components, for example, may be included in a kit: (i) one or more nucleotides (e.g., terminating nucleotides and/or non-terminating nucleotides); one or more of which can include a detection label (ii) one or more nucleotides comprising a capture agent; (iii) one or more oligonucleotides, one or more of which can include a detection label (e.g., amplification primers, one or more extension primers (UEPs), oligonucleotides comprising a tag, oligonucleotides comprising a capture agent); (iv) one or more enzymes (e.g., a polymerase, endonuclease, restriction enzyme, etc.); (v) controls components (e.g. control genomic DNA, primers, synthetic templates, target nucleic acids, etc.) (vi) one or more buffers and (vii) printed matter (e.g. directions, labels, etc). In embodiments of the kit, the relative amounts of terminating nucleotides are present in solution or are present in relative amounts such that upon dissolution according to the directions provided, the concentration of the chain terminating nucleotide specific for a major nucleic acid species (C[WT]) is less than the concentration of chain terminating nucleotide(s) specific for the minor nucleic acid species (C[Mut]). In embodiments, the concentration of the chain terminating reagent specific for the majority nucleic acid species C[WT] is less than 20% of the concentration of the chain terminating reagents specific for the minority nucleic acid species (C[Mut]), C[WT] generally being between about 0.5% to less than about 20% of C[Mut], about 0.5% to less than about 15% of C[Mut], about 1% to about 15% of C[Mut], about 1% to about 10% of C[Mut], about 2% to about 10% of C[Mut] or about 1%, 1.5%, 2%, 2.5%, 3%, 3.5%, 4%, 4.5%, 5%, 5.5%, 6%, 6.5%, 7%, 7.5%, 8%, 8.5%, 9%, 9.5% or 10% of C[Mut]. In certain embodiments, C[WT] is between about 0.1% to about 10% of C[Mut], between about to about 10% of C[Mut] or about 0.01%, 0.05%, 0.1%, 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5% or 10% of C[Mut].

A kit sometimes is utilized in conjunction with a process, and can include instructions for performing one or more processes and/or a description of one or more compositions. A kit may be utilized to carry out a process described herein. Instructions and/or descriptions may be in tangible form (e.g., paper and the like) or electronic form (e.g., computer readable file on a tangle medium (e.g., compact disc) and the like) and may be included in a kit insert. A kit also may include a written description of an internet location that provides such instructions or descriptions.

EXAMPLES

The examples set forth below illustrate, and do not limit, the technology.

Example 1—PCR Amplification

In embodiments of the methods provided herein, a sample or combination of samples containing a mixture of one or more major nucleic acid species and one or more minor nucleic acid species is subjected to PCR amplification, using suitable amplification primers. Exemplary amplification conditions are as set forth, for example, in U.S. Published Patent Application No. 2013/0237428 A1, U.S. Pat. Nos. 8,349,566, and 8,003,317, and in Oeth et al., SEQUENOM® Application Note, Document No. 8876-006, R04, published Nov. 10, 2006, the contents of which are incorporated in their entirety by reference herein. For example, amplification conditions can be set up as follows:

TABLE 1

PCR Cocktail Mix

| Reagent | Final Concentration per 5 μl Reaction | Volume (μl) (1 rxn) |
|---|---|---|
| Nanopure $H_2O$ | N/A | 1.850 |
| 10X PCR Buffer with $MgCl_2$ | 1.25X | 0.625 |
| Primer mix (500 nM each) | 100 nM | 1.000 |
| dNTP mix (25 mM) | 500 μM | 0.100 |
| Sample DNA (major/minor nucleic acid species; 5-10 ng/μl) | 5-10 ng/rxn | 1.000 |
| Hotstar Taq ® polymerase (5U/μl) | 0.5 U/rxn | 0.100 |

The components of Table 1 are mixed and gently vortexed. Exemplary conditions for PCR cycling are as follows: 94° C. for 15 minutes; 45 cycles of 94° C. for 20 seconds/56° C. for 30 seconds/72° C. for 1 minute; 72° C. for 3 minutes; cooling to 4° C.

Example 2—Treatment with Shrimp Alkaline Phosphatase (SAP)

Following amplification, unincorporated dNTPs are dephosphorylated by treatment with SAP. The “SAP Mix” is prepared using the combination of reagents set forth in Table 2:

TABLE 2

SAP Mix

| Reagent | Volume (μl) (1 rxn) |
|---|---|
| Nanopure $H_2O$ | 1.330 |
| 10X SAP Buffer | 0.170 |
| SAP enzyme (1U/μl) | 0.500 |

The SAP Mix prepared according to Table 2 (total volume: 2 μl) is added to the 5 μl PCR reaction from Example 1. Each 5 μl PCR reaction treated in this manner is gently mixed or vortexed. The treated samples are incubated in a standard thermocycler as follows: 37° C. for 40 minutes; 85° C. for 5 minutes; cooling to 4° C.

Example 3—UEP Primer Extension

To each of the SAP-treated samples from Example 2 is added 2 μl of an Extension Cocktail Mix, an exemplary one of which is prepared as set forth in Table 3 below:

TABLE 3

Extension Cocktail Mix

| Reagent | Final Concentration in 9 μl Reaction | Volume (μl) (1 rxn) |
|---|---|---|
| Nanopure $H_2O$ | N/A | 0.755 |
| iPLEX Buffer Plus (10X) | 0.222X | 0.200 |
| UEP Primer mix (7 μM low mass; 14 μM high mass) | 0.625 μM low mass; 1.25 μM high mass | 0.804 |

TABLE 3-continued

| Extension Cocktail Mix | | |
|---|---|---|
| Reagent | Final Concentration in 9 µl Reaction | Volume (µl) (1 rxn) |
| ddNTP mix | 50-200 µM $C[Mut]_{ddNTP}$; 1-20 µM $C[WT]_{ddNTP}$ | 0.200 |
| iPLEX Enzyme | 1X | 0.041 |

The components of Table 1 are mixed and gently vortexed. Exemplary conditions for extension cycling can be as follows: 2-step 200 short cycles program in a standard thermocycler with 94° C. for 30 seconds; 40 cycles of 94° C. for 5 seconds/(52° C. for 5 seconds/80° C. for 5 seconds—cycle through this 5 times, for a total of 200 short cycles); 72° C. for 3 minutes; cooling to 4° C. The 200 short cycle program uses two cycling loops, one of 5 cycles within a loop of 40 cycles, thereby resulting in a 200 cycle program.

Example 4—MALDI-TOF Analysis

Desalting of the extended products formed according to Example 3 is achieved by the addition of 6 mg CLEAN Resin (Sequenom). 15 nl of the cleavage reactions are dispensed robotically onto silicon chips preloaded with matrix (SpectroCHIP®, SEQUENOM®), using a nanodispenser. Mass spectra are acquired using a MassARRAY Compact Analyser (MALDI-TOF mass spectrometer). The samples are transferred onto a 384-well SPECTROCHIP®-(SEQUENOM®; San Diego, CA). The entire SPECTROCHIP® microchip is transferred into a BRUKER/SEQUENOM® mass spectrometer, which allows automated measurement of the samples. Positive ions are analyzed and ~100 single shot spectra are accumulated (e.g., 5 raster positions×20 shots/position). All samples are analyzed in linear time-of-flight mode using delayed ion extraction and a total acceleration voltage of 20 kV. See the "Dispensing Primer Mass Extension Reaction Products onto SPECTROCHIP®" chapter in MASSARRAY® Nanodispenser User's Guide available from SEQUENOM® (San Diego, CA) for instructions. The MASSARRAY® Typer system (Typer version 3.0) is used to acquire spectra from the SPECTROCHIP® as described in the "SPECTROACQUIRE" chapter in MASSARRAY® Typer User's Guide also available from SEQUENOW-(San Diego, CA).

Example 5—Exemplary Protocol and Results Using Skewed ddNTP Concentrations

As discussed, the methods provided herein combine improved detection sensitivity of minor nucleic acid species in a sample, such as minor alleles, with the ability to quantify their frequency, amount or copy number relative to a major nucleic acid species, such as major alleles. This is accomplished by adjusting, in the extension reactions, the concentration range of the chain terminator reagent (e.g., ddNTP) that is specific for the major nucleic acid species so that it is less than the concentration of the chain terminator reagent specific for the minor nucleic acid species, thereby increasing the detection limit of the signal from the minor nucleic acid species, yet not so low that the major nucleic acid species signal is reduced to the level of background noise, thereby precluding its use as a positive control (to ensure the integrity of the method, i.e., when detecting the presence or absence of a signal corresponding to a minor nucleic acid species, ensuring that the observed result is real) or as a basis for quantifying the relative amount (frequency, copy number, e.g.) of the minor nucleic acid species.

An exemplary protocol is as follows:

Assay Design

Each assay consists of three primers, two PCR primers and one single base extension primer. Amplicon (nucleic lengths can be varied but usually recommended to be under 150 bp in length to ensure amplification success in samples such as circulating cell free DNA and degraded DNA isolated from FFPE (formalin-fixed paraffin embedded tissue). Mass tags are added to the 5' end of the primer to move unincorporated PCR primers out of the analytical mass window or allow for validation using next generation sequencing. Extension probe design also has a few requirements. First, the mass of the extended products must be sufficiently spaced by a mass difference to ensure no conflicts between assays (e.g., overlap of signal). Second, multiplexing is based on reactions designed so that each reaction container is restricted to nucleic acid species that have the same specific chain terminator nucleotide incorporated. For example, in an "A" multiplexed reaction, the chain terminator nucleotide for all the nucleic acid species in the reaction is ddA and all assays with this terminator nucleotide can be combined together. Additional liberty in design is obtained by allowing reverse design, i.e., probing a sequence on the opposite stand in this case a "T" can be investigated as the probe would target the "A" on the opposite strand.

PCR Amplification

PCR was carried out in a total volume of 20 µL, with 10 µL of DNA template supplemented with 10 µL of a master mix consisting of 1×PCR Buffer supplemented with 1 mM $MgCl_2$, 125 µM dNTPs, 0.125U Uracil-DNA glycosylase (New England Biolabs®, Ipswich, MA, USA), 4U Taq polymerase, and 100 nM of each PCR primer. Reactions were initially incubated at 30° C. for 10 minutes followed by 94° C. for 2 minutes. 45 cycles of PCR were performed at 94° C. for 30 seconds, 56° C. for 30 seconds, and 72° C. for 1 minute. The PCR was completed with a final incubation of 5 minutes at 72° C. 5 µL of amplified products were conditioned with the addition of 2 µL of 0.5U shrimp alkaline phosphatase (SAP) in 0.24×SAP buffer in a total volume of 7 µL for 40 minutes at 37° C., followed by SAP enzyme denaturation for 10 minutes at 85° C. All reagents used were obtained from Agena Bioscience, Inc., unless otherwise stated.

Single Base Extension

Single base extension was performed by adding 2 µL of a Mastermix consisting of 0.2× extension buffer, 200 µM of the minor allelic variant nucleotide amplicons and different concentrations of the major allele variant nucleotide amplicons ranging from 0.25 µM-20 µM, extension primers at various concentrations, and 0.14U iPLEX® Pro enzyme. Single base extension reactions were performed in a total volume of 94. Reaction parameters included an initial incubation at 94° C. for 30 seconds followed by 40 cycles at 94° C. for 5 seconds with five nested cycles of 52° C. for 5 seconds then 80° C. for 5 seconds. The single base extension was completed with an incubation at 72° C. for 3 minutes.

Capture and Data Acquisition

Prior to nanodispensing, the products were conditioned with 5 μL (3 mg) of anion exchange resin slurry for desalting. Finally, the analyte was dispensed onto a Spectrochip® II solid support using an RS1000 Nanodispenser. Data was acquired via MALDI-TOF mass spectrometry using the MassARRAY® 4 instrument.

Exemplary results of analyses according to the methods provided herein are illustrated in FIGS. 1A-C, 2A-D and 3A-I. As shown in FIGS. 1A-C, a sample containing a mixture of a minor nucleic acid species (minority allele) and a major nucleic acid species (majority allele), where the minority allele is present at 5% frequency relative to the majority allele, is subjected to amplification and extension reactions according to the iPLEX™ method or according to the methods provided herein. The extreme left panel (FIG. 1A) shows the results of analysis using the iPLEX™ method, in which equimolar concentrations of the chain terminating reagents are used. As the panel shows, the signal peak on the left, which corresponds to the extension product from the majority allele, is so predominant that the minority peak on the right is reduced to the level of background noise and is undetectable. The middle panel (FIG. 1B) shows the results obtained when the concentration of the chain terminating reagent specific for the majority allele is 20% (one fifth) that of the concentration of the chain terminating reagent specific for the minority allele. As seen in the middle panel, the intensity of the detection signal from the minority allele extension product (right peak) is now higher and more visible relative to the signal from the majority allele extension product (left peak). The minority allele signal, however, is still small and close to the level of background noise. The extreme right panel (FIG. 1C) shows the results obtained when the concentration of the of the chain terminating reagent specific for the majority allele is about 6-7% (one fifteenth) that of the concentration of the chain terminating reagent specific for the minority allele. As seen in the right panel, the signal from the minority allele extended product (right peak) is now comparable to the signal from the majority allele (left peak). Thus, FIGS. 1A-C demonstrates that by skewing the concentration of the chain terminating reagents in favor of the minor nucleic acid species, minor nucleic acid species at frequencies of less than 10%, which could not effectively be detected by methods such as iPLEX™, can be detected by the methods provided herein.

Further, as shown in FIGS. 3A-I, the methods provided herein can be useful for the detection of minor nucleic acid species that are present at a frequency of less than 2%, as low as 1.25%, relative to the major nucleic acid species in a sample. FIGS. 3A-I show a comparison of the results obtained when the sample is subjected to amplification, followed by extension under three conditions: (A) concentration of chain terminator ddNTP specific for the major nucleic acid species (wild type allele; $C[WT]_{ddNTP}$) is equal to the concentration of chain terminator ddNTP specific for the minor nucleic acid species (mutant allele; $C[Mut])_{ddNTP}$); (B) $C[WT]_{ddNTP}$) is less than about 20% of the concentration of $C[Mut])_{ddNTP}$ (i.e., ratio of $C[WT]_{ddNTP}$:$C[Mut])_{ddNTP}$ is 0.2); and (C) $C[WT]_{ddNTP}$) is less than about 5% of the concentration of $C[Mut])_{ddNTP}$ (i.e., ratio of $C[WT]_{ddNTP}$:$C[Mut])_{ddNTP}$ is 0.05). As seen in FIGS. 3A, 3D and 3G, when the ratio of $C[WT]_{ddNTP}$:$C[Mut])_{ddNTP}$ is 1, i.e., the two chain terminator concentrations are equal (as used, e.g., in the iPLEX™ method) mutant allele frequencies of 5%, 2.5% and 1.25% were all below the limit of detection (LOD). When the ratio of $C[WT]_{ddNTP}$:$C[Mut])_{ddNTP}$ was decreased to 0.2, mutant allele frequencies of 5% could be detected, while the 2.5% and 1.25% mutant allele frequencies were still below the limit of detection (see FIGS. 3B, 3E, 3H). When the ratio of $C[WT]_{ddNTP}$:$C[MUt])_{ddNTP}$ was further decreased to 0.05, all three mutant allele frequencies (5%, 2.5% and 1.25%) could be detected (see FIGS. 3C, 3F and 3I).

Example 6—iPLEX+ Feasibility Study

The iPLEX chemistry implemented on the MassARRAY system offers accurate and sensitive detection of single nucleotide polymorphisms (SNPs), somatic mutations and copy number variations (CNVs). Without being limited by theory, the sensitivity of the iPLEX chemistry for the somatic mutation minor variant detection is 10% and higher. The 10% minor allele frequency threshold is the practical limitation of the iPLEX method that stems from the MassARRAY platform properties. MassARRAY is a MALDI-TOF mass spectrometer that features an 80 cm linear TOF analyzer which has the maximum dynamic range of 50× (smallest-to-highest peak in the spectrum). This 50× dynamic range is further reduced by the ion signal quantity and the amount of noise. For example, the conservative 10× dynamic range threshold (10% minor variant frequency) has been adopted for the iPLEX somatic mutation applications. iPLEX+ chemistry attempts to increase the sensitivity of the existing iPLEX chemistry to the levels below 10% of minor variant.

In somatic mutation applications the mutation frequency is determined as either the ratio of the intensities of the minor mutant peak to the dominant wild type (WT) peak or the percentage of the minor mutant peak. In either case the intensity of the WT peak serves as the background against which the mutant peak is measured. For example, given the theoretical 50× dynamic range of the MassARRAY instrument and the practical 10× dynamic range, the hypothetical 5% minor allele would be detected at the level below the limit of detection (LOD) threshold and, therefore, will not be reported as a high confidence mutation.

Alteration of the dynamic range limitations of regular iPLEX were investigated by depleting the amount of the WT ion peak compared to that of regular iPLEX. This modified version of the iPLEX is referred to as iPLEX+.

During the iPLEX reaction the unextended primer nucleotide (UEP) is converted into product by incorporating a template-specific single terminator nucleotide (acyclonucleotide) over the course of 200 extend reaction cycles. The extend reaction is a bi-molecular reaction where the amount of the product (observed peak) is proportional to the product of the DNA template concentration for either the WT or the minor peak and the amount of the terminator nucleotide:

$$[WT_{product}]\sim[DNA_{WT}]\times[WT_{terminator}],$$

$$[Minor_{product}]\sim[DNA_{Minor}]\times[Minor_{terminator}]$$

Given the higher concentration of the WT DNA template and the equal concentrations of the WT and the minor terminators of regular iPLEX, the relative intensities of the detected peaks will be proportional to the DNA template amounts. One way to decrease the amount of the WT peak and "shift" the equilibrium towards the minor product is to reduce the amount of the WT terminator nucleotide compared to the minor terminator nucleotides. iPLEX+ is a WT-depleted version of the regular iPLEX where the previously equimolar mixture of four terminating nucleotides is now depleted for the WT allele (for example, depleted to the levels below 1% of the total). By reducing the amount of WT-specific terminator the equilibrium of the extend reaction is shifted toward formation of the minor product. The enrichment of the minor peak will vary according to the amount of the WT terminator available to the reaction.

A feasibility study was conducted to determine whether the WT-depleted iPLEX method (WT-depleted mixture of the terminator nucleotides) called iPLEX+ will allow for minor allele detection at levels below 10%. The performance of iPLEX+ was investigated using a comprehensive panel of assays that cover all potential WT-mutant scenarios (transitions) using a model system where 0%, 1%, 2.5% and 5% were created as a dilution series of human-chimp DNA. The model system was verified with an orthogonal technology (Ion Torrent PGM). Three rounds of comprehensive studies were carried out where the iPLEX+ panel of over 300 assays was interrogated against multiple technical replicated of the entire dilution series. After each feasibility round several extend reaction parameters were evaluated in an attempt improve the overall panel performance. Additional goals include establishing the sensitivity of the iPLEX+ method, determining whether iPLEX+ is quantitative and establishing the initial parameters of the biochemistry (terminator nucleotide mixture, terminator nucleotide amounts and the extend reaction parameters). The study demonstrated that the iPLEX+ method allows for near 100% sensitivity of detection of 5% mutants, higher than 90% sensitivity toward 2.5% mutants and 35-61% average sensitivity (depending on the conditions of the method, with 50% being the average sensitivity) toward 1% mutants.

Model System

The model system used to mimic low frequency mutations and interrogate all possible WT-mutant allele combinations was a mixture of human and chimp (*Pan Troglodytes*) genomic DNA. Whole-genome sequence alignment was carried out between human hg19 reference assemble and *P. troglodytes* 2013 assembly to select short orthologous sequences with a single stable nucleotide mismatch between human and chimp. These regions became the iPLEX+ assay candidates. Another set of criteria applied to the orthologous regions is that they have to map to human exons inside ORFs of 5 exons or larger, and that the distance between the regions on the same chromosome has to be higher than 5,000 b.p. The final number of the qualified assay candidates was 5,822.

Assay Design

Agena Bioscience Assay Design Suite 2.0 was used to design iPLEX+ assays using the candidates from the human-chimp model. The assay design was implemented using "somatic mutation" settings with the maximum multiplex level of 15. iPLEX+ presents a multiplexing constraint that is not part of generic iPLEX assay design. The WT-depleted composition of the termination mix creates scenarios where one of four nucleotides is the WT for all assays in the "channel." A multiplex of assays all having the WT major allele as A is called an A-channel or A-transition. The A transition has the depleted A nucleotide extending all major WT products and the C, G and T nucleotides extending minor products. The assay design was carried out with the input sequences that had the assay directionality specified prior to design to eliminate a reverse assay design with complimentary nucleotides (a common feature of assay designer). The assay design was carried out separately for the four channels (WT-A, C, G, T) and the multiplexes were combined into the final design. The final design featured all of the 12 possible WT-minor transitions, three transitions per WT terminator (for example, the A-channel has three WT-minor transitions a/C, a/G, a/T). The combined assay design features 334 assays in 24 multiplexes and has all possible transitions represented by at least 20 assays.

Biological Samples

Biological samples were created using the pooled human genomic HapMap01 (Coriell) DNA samples and the chimp DNA from a single individual, Max (Coriell). In all human-chimp mixtures the human DNA was the major component that provided the WT allele while chimp DNA was used as the minor component. The total amount of DNA per sample (either pure or a mixture) was set to around 3,300 genomic DNA copies which corresponds to 10 ng of DNA per sample.

Assay Validation with iPLEX

The 334 assays were validated using the regular iPLEX chemistry using 100% human sample, 100% chimp samples and the 50% human-chimp mixture. The initial validation with regular iPLEX was carried out to determine poor performing assays. Poor performing assays are the assays with low extension rates (usually below 80%) and the assays that have poor template specificity, which manifests in the assay skew (non-specific extension of the non-template allele). The assay extension rate is calculated as the fraction of the assay product peaks over all assay peaks, including the UEP:

$$ExtRate = \frac{\Sigma products}{UEP + \Sigma products}$$

The iPLEX validation was carried out to determine the assays that have failed because of either technical or biological reasons. These reasons include poor design (poor primer specificity, poor annealing characteristics, poor multiplexing, etc.), biology (unexpected SNP or sequence variation within the amplicon at the position of either the PCR or the extend primers, non-specific annealing of the assay primers), or a technical reason (the assay is located at the position of salt adducts, poor quality of the assay primers). Of 334 designed assays, 15 assays had the extension rate below 80% and, therefore, were flagged as poor. In addition to the extension rate, the regular iPLEX data was used to determine the assays that were either skewed or had non-specific extension. Since the assays interrogate stable regions in both human and chimp DNA the expectation is that the 100% human and 100% chimp samples will be homozygous. 41 assays, however had 10% or higher minor allele frequency at the position of the heterozygous allele. For example, an assay that is heterozygous in 100% chimp sample exhibited non-template extension of the G allele (human) and resulted in a heterozygous call where only the homozygous T allele is expected. Therefore, a total of 49 unique assays were discovered to have either poor extension rates or non-specific extension. The design-to-panel success rate was 85%, which lies within the ADS 2.0 acceptance criterion of >80% success rate of the designed assays. Of the 49 poor assays 24 failing assays (very poor extension rate<0.5 and non-template allele extension) were removed from further analysis.

iPLEX+ First Round

The first round of the iPLEX+ experiments consisted of the following study. Human/Chimp DNA was pooled into dilution series to represent 0%, 1%, 2.5% and 5% chimp contribution. The 0% chimp samples are 100% human WT control samples. The WT terminator nucleotide fraction was set to 1% in all four terminator mixes (a/CGT, c/AGT, g/CAT and t/ACG). Each dilution series was interrogated in 16 technical replicates. The following criteria were evaluated when determining the method performance:

assay extension in 0% chimp samples,
chimp frequency in 0% chimp samples,
assay sensitivity,
transition performance and sensitivity,
overall sensitivity.

The first two criteria were used to as a quality control measure to remove the assays that have failed during the experiment. In order to evaluate sensitivity of the individual assay it has to extend in 0% chimp (100% human WT DNA samples) to produce the minimum detectable WT peak (SNR of 5 or higher). Without the viable WT signal at 0% chimp the assay performance at 1%, 2.5% and 5% chimp cannot be evaluated because of the lack of comparison to the baseline. The second criterion—observed chimp minor allele in WT samples, was used to remove non-specific assays that fail due to the assay design, not the iPLEX+ methodology.

Given the WT-depleted principle of iPLEX+, it was expected to observe lower extension rates of iPLEX+ assays at 100% WT, than the extension rates at 5% chimp and the regular iPLEX. The average assay extension rate of the regular iPLEX was 0.95 while the extension rate of iPLEX+ 0% chimp samples was 0.40 and the iPLEX+5% chimp samples was 0.78. The WT-depleted formulation of the nucleotide terminator mixes shifted the equilibrium toward minor allele products, therefore the 100% human WT samples, where there is no minor product, showed much lower assay extension rates. One of the tasks of the feasibility study was to establish the WT nucleotide concentration that would ensure assay extension in 100% WT samples. After evaluating the method performance in the 1st round, 96 assays did not extend in 100% human WT samples and 36 assays had non-specific chimp extension in WT samples. Therefore, only 57% of the assays were functional.

After removing poor assays the assay performance and the panel sensitivity were estimated. The main criterion that was used to estimate assay performance was whether the experimentally observed chimp frequency from 1%, 2.5% and 5% chimp dilution can be differentiated from the 0% chimp WT samples. The chimp frequency was derived from the allele ratios between the two peaks, the human allele peak and the chimp allele peak. The allele peak ratios were expressed as numeric genotypes as follows:

$$\text{Numeric Genotype} = \frac{\text{Intensity}_{low\ mass}}{(\text{Intensity}_{low\ mass} + \text{Intensity}_{high\ mass})}$$

Where $\text{Intensity}_{low\ mass}$ is the peak intensity of the low mass allele and $\text{Intensity}_{high\ mass}$ is the peak intensity of the high mass allele. The numeric genotype represents the chimp minor allele frequency in instances when the chimp allele is at the low mass. In cases when the chimp allele is at the high mass, chimp frequency was calculated as 1—numeric genotype.

Figure 4:
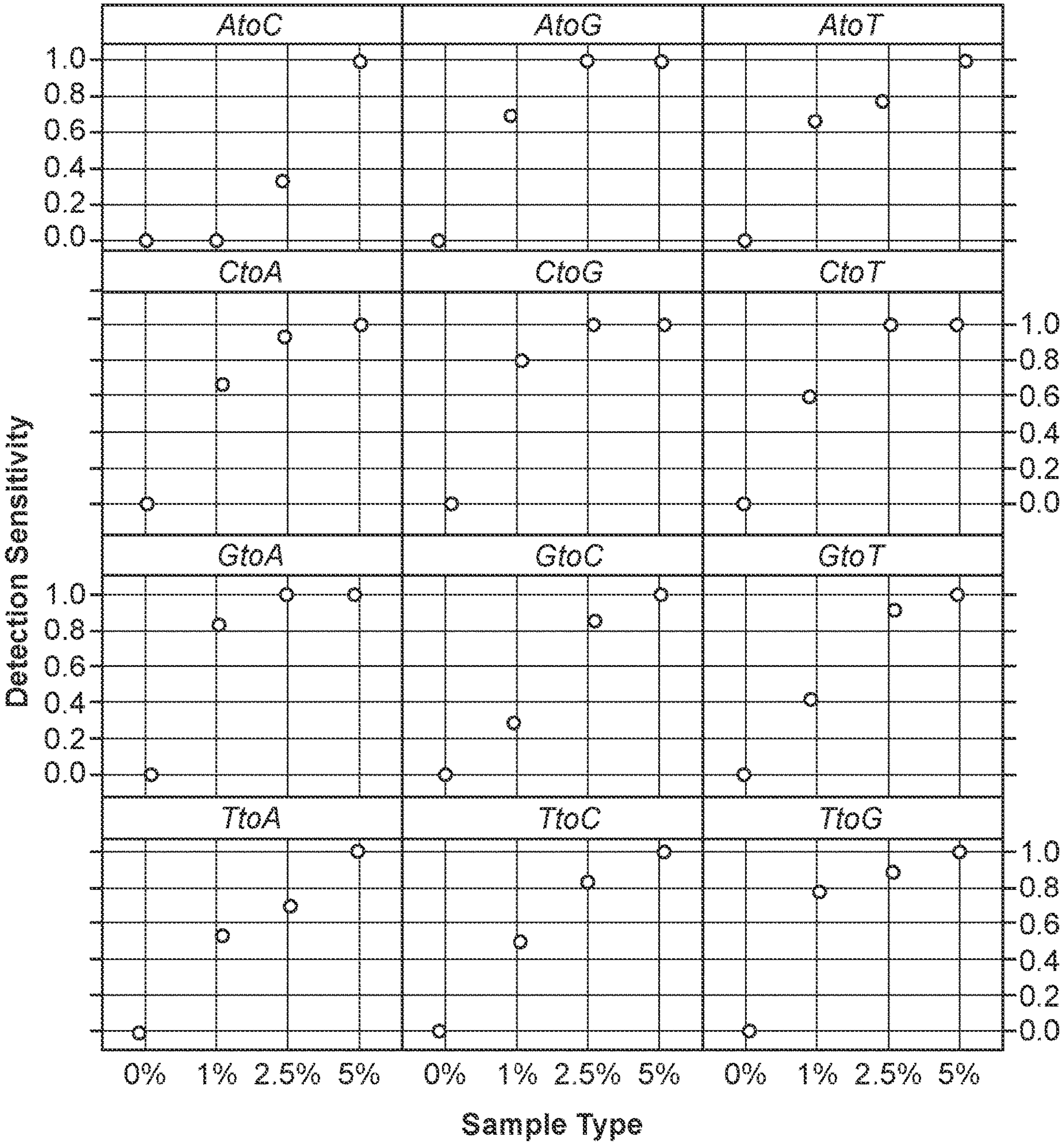
FIG. 4 shows per transition (individual panels) sensitivity of detection (y-axis) for each dilution series sample type (0%, 1%, 2.5% and 5%).

The per-assay performance for 16 technical replicates was evaluated. Data (observed chip frequency) was plotted as lattice plots per assay with the y-axis as the observed chimp frequency and the x-axis as the dilution series with the WT samples being 0% chimp. The data was evaluated according to whether the samples could be differentiated from 0% chimp with a degreed of statistical significance. The statistics used was t-tests with Bonferroni correction for multiple comparisons and the critical alpha value was set to 0.95. The assay chr2_AtoC_104 could significantly differentiate the 2.5% and the 5% chimp samples from 0% chimp samples. The following two assays, chr20_AtoC_118 and chr4_AtoC_146 could only distinguish 5% from 0% chimp, while the chr1_AtoG_115 assay could differentiate all dilutions from 0% chimp. The per-transition and the overall sensitivity of iPLEX+ was calculated by using the significance outcomes from each assay. FIG. 4 shows the per-transition sensitivity of iPLEX+. The sensitivity at each dilution level (0%, 1%, 2.5% and 5% chimp) were calculated as an average number of the assays that are statistically significantly different (from 0% chimp) for that dilution level. For example, the top left corner of FIG. 4 shows that the sensitivity at 1% chimp is 0, the sensitivity at 2.5% chimp is 0.33 and the sensitivity at 5% chimp is 1.0 based on the assays that represent A-to-C transition. This means that the 1% cannot be distinguished from 0 in any assays for that transition, the 2.5% dilution can be distinguished 33% of the time and the 5% dilution can be distinguished 100% of the time. The overall panel sensitivity for each dilution series was 0.61 for the 1%, 0.88 for the 2.5% and 1.0 for the 5% chimp frequency samples.

Figure 5:
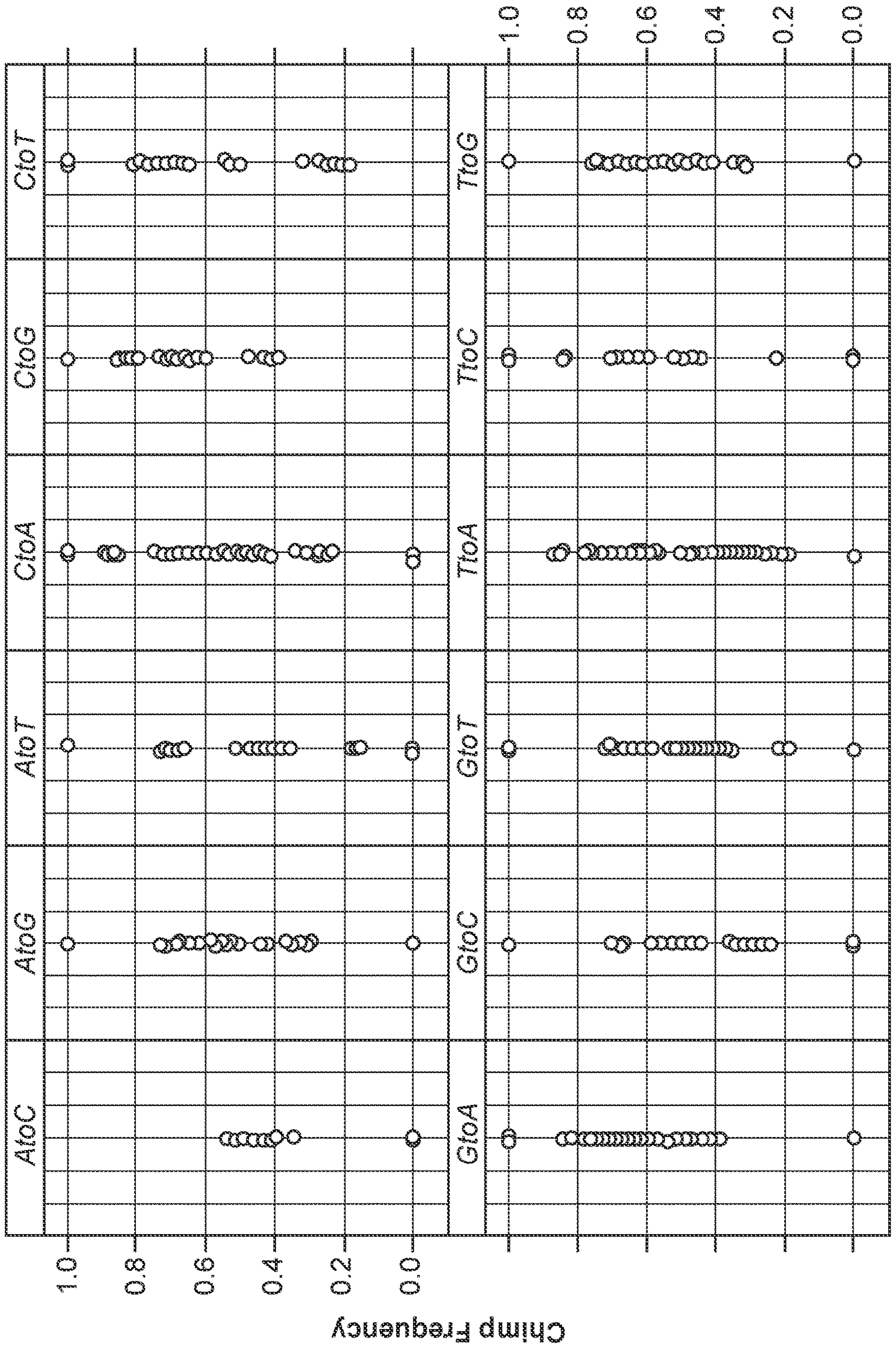
FIG. 5 shows observed chimp frequency (y-axis) for the 5% chimp dilution series. The panels represent unique transitions and the data points represent the observed chimp frequencies for the assays in those transitions.

The iPLEX+ sensitivity differed according to the assay and transition. Significant assay-specific and transition-specific biases that challenge the quantitative aspect of iPLEX+ was observed. FIG. 5 shows the observed chimp frequency for the assays in different transitions using 5% dilution of chimp DNA into human.

During the round 1 of the feasibility study it was shown that the WT nucleotide depleted approach of iPLEX+ can be used to successfully reduce the WT allele signal and increase the assay sensitivity to the levels below 10%. According to the data iPLEX+ can be used to detect minor variants below 10% with the excellent sensitivity of 100% for the 5% mutants, 88% for the 2.5% mutants and 61% for the 1% mutants. Some of the drawbacks of the method as of round 1 include poor assay extension in WT samples and assay-specific nucleotide incorporation. In order to overcome low assay extension, low intensities of the products and mitigate some of the assay-specific incorporation bias a round of optimization was conducted where the nucleotide termination mixes (set to 1% for the WT nucleotide and equimolar for the mutant alleles in round 1) were optimized for each transition.

Nucleotide Terminator Optimization

The nucleotide terminator optimization was carried out using technical replicates of the 5% chimp dilution resulting in 16 data points acquired for each assay (14 replicates and 2 NICs). The following termination mixes were evaluated: 2%, 4%, 8% and 16% WT nucleotide. The goal of the nucleotide terminator optimization was to determine the optimal proportion of the WT nucleotide terminator for each transition. The optimization criterion was the relative peak height of the 5% chimp minor allele peak to the WT peak. The optimization goal was to create the terminator mixtures that would result in equal peak heights of the WT and the 5% chimp peaks.

The different concentrations of the WT nucleotide produced different response of the chimp minor product. Increasing the amount of the WT terminator from 1% to 16% decreases the observed minor allele fraction for all transitions. Increasing the WT nucleotide fraction from 8% to 16% results in diminished signal from the 5% chimp minor allele, which makes iPLEX+ behave similar to the regular iPLEX. As with the previous iPLEX+ experiments transition-specific allele incorporation was indicated by the general spread of data points for each WT percent. However, the 2% WT nucleotide amount is the optimal amount on average to detect 5% chimp minor allele as a 0.5 chimp allele frequency.

The adjusted WT nucleotide percentage for each transition (based on the mean for that transition) to yield 0.5 chimp allele frequency was calculated. These data are presented in Table 4. The adjusted WT nucleotide percentages (bottom row) were selected to be used in the next round of iPLEX+ feasibility.

chimp (compared to 0.88 in round 1) and 0.98 for the 5% chimp (compared to 1.0 in round 1). In addition, as in round 1, a significant degree of assay-specific extension which resulted in high variability of the observed minor allele fraction at each dilution series was observed. Therefore, the main benefit of the transition-specific WT nucleotide approach is that there were fewer assays that failed to extend at 0% in round 2 (44 assays) than those in round 1 (96 assays).

TABLE 4

| Percent WT | AtoC | AtoG | AtoT | CtoA | CtoG | CtoT | GtoA | GtoC | GtoT | TotA | TtoC | TtoG |
|---|---|---|---|---|---|---|---|---|---|---|---|---|
| 1 | 0.63 | 0.68 | 0.68 | 0.7 | 0.74 | 0.71 | 0.71 | 0.57 | 0.48 | 0.68 | 0.72 | 0.69 |
| 2 | 0.38 | 0.46 | 0.44 | 0.54 | 0.57 | 0.53 | 0.58 | 0.39 | 0.33 | 0.49 | 0.5 | 0.48 |
| 4 | 0.22 | 0.28 | 0.19 | 0.4 | 0.42 | 0.35 | 0.4 | 0.22 | 0.2 | 0.37 | 0.32 | 0.34 |
| 8 | 0.16 | 0.21 | 0.11 | 0.29 | 0.3 | 0.23 | 0.27 | 0.12 | 0.12 | 0.25 | 0.17 | 0.21 |
| 16 | 0.13 | 0.17 | 0.07 | 0.2 | 0.21 | 0.13 | 0.19 | 0.06 | 0.09 | 0.2 | 0.12 | 0.18 |
| Projected % WT for 0.5 chimp allele frequency (Chimp/(Chimp + Human) | 1.5 | 2.15 | 1.9 | 3 | 3.5 | 2.8 | 3.25 | 1.15 | 1 | 2.5 | 2.5 | 2.5 |

iPLEX+ Second Round

The second round of iPLEX+ feasibility study was identical to the first round in its layout and scope with the exception of the termination mix. The round 1 was performed using 1% WT nucleotide terminator in its universal nucleotide mixture while the round 2 was carried out using the transition-specific WT nucleotide amounts (Table 4). The round two of iPLEX+ feasibility consisted of the following study. Human/Chimp DNA was pooled into dilution series to represent 0%, 1%, 2.5% and 5% chimp contribution. Each dilution series was interrogated in 16 technical replicates. As the case in round 1 the following criteria were evaluated when determining the method performance:

- assay extension in 0% chimp samples,
- chimp frequency in 0% chimp samples,
- assay sensitivity,
- transition performance and sensitivity,
- overall sensitivity.

Similar to that in round 1 poor performing assays were identified in round 2. 44 assays (compared to 96 in round 1) did not yield sufficient signal in 100% WT samples. That is a 2.2 fold improvement over the round 1 that is due entirely to an increased WT nucleotide concentration in round 2. In addition to the failing assays, 33 assays extended chimp allele in 100% WT samples (compared to 36 in round 1). A total of 77 assays (25% of the panel) were poor in round 2 compared to 136 assays in round 1 (43% of the panel). The assays were removed from further analysis.

The effect of increasing the WT nucleotide contribution on the extension rates was investigated. (0% chimp, the 5% chimp and the regular iPLEX). A significant change from the extension rates in round 1 was not observed. The average extension rate for the 0% chimp samples was 0.41 (compared to 0.40 in round 1) and that for the 5% chimp samples was 0.63 (compared to 0.78 in round 1).

Using the same approach that was used in round 1 the sensitivity of each transition and the overall sensitivity of the panel was examined. Moderate changes at the level of each transition were observed, however, the overall performance of the round 2 panel was similar to that of the round 1. The overall sensitivity of the round 2 panel was 0.52 for the 1% chimp (compared to 0.61 in round 1) 0.91 for the 2.5%

Orthogonal Verification of the Model System

Following the round 1, the nucleotide optimization and the round 2 studies a set of experiments to validate the human-chimp model system that was used in iPLEX+ development was carried out. The assays (as previously described in Model System) were created to interrogate target regions that are different in human and chimp genomes and the dilution series samples were created to represent 0% chimp, 1% chimp, 2.5% chimp and 5% chimp minor allele frequency on the background of the major human allele. A set of experiments was carried using Ion Torrent PGM (Life Technologies) to validate the target regions and to verify the extent of dilutions. Libraries for sequencing were prepared by amplifying the iPLEX(+) designed amplicons using the iPLEX PCR cocktail and dNTPS. The recommended gDNA input into this PCR reaction was 10-20 ng per multiplex. DNA quantity in each multiplex was measured with the BioAnalyzer DNA 1000 kit and pooled in equimolar parts. The input amplicon library into the NEBNext® Fast DNA Fragmentation & Library Prep Set for Ion Torrent was 50 ng for each multiplex. The Ion Torrent library preparation involved end repair, adaptor ligation with the P1 and A adapters, nick translation, and a small 6× cycle PCR. Cleanup following individual steps was with the Ampure XP Beads. Library QC and quantification was performed using the BioAnalyzer DNA 1000 kit, and library input into the Ion Torrent-PGM OT2 200 kit was 26 pmol. Enrichment for templated-ISPs was performed using the Ion Torrent OT2 ES machine. The sequencing of these templated-ISPs was performed on the PGM system using the Ion Torrent 200 Sequencing kit and 240 flows of nucleotides. Each model was sequenced using a singular 318 or 318 v2 chip. Data analysis was performed by aligning sequencing reads to a BED file containing genomic coordinates of the iPLEX(+) designed target amplicons. The Ion Torrent coverage analysis and the variant caller plugins were used to automatically calculate and validate the target representation and the minor variant frequency.

Using the Ion data 278 out of 310 targets (90% of the targets) for the 5% chimp dilution library were confirmed. The median chimp minor allele variant frequency was 4.9% for the 5% chimp library and the median target coverage was 10,000×. The minimum coverage cutoff was 5,000× for the analysis. The 2.5% dilution series library resulted in 189 targets being confirmed (61%) with the median minor allele variant frequency 3.6% and the median coverage of 8,200×.

Each dilution library contained less than 5% outliers with much higher chimp allele frequencies than the intended 5% and 2.5%. Examination of the correlation between the 5% and the 2.5% dilution series targets made evident that the variant outliers found in the 5% and the 2.5% data belong to the same target assays.

No 1% variants in 1% Ion PGM runs were identified primarily due to poor chip loading that did not yield the sufficient target coverage to identify 1% chimp variants. The 0% chimp libraries did not produce any variants as expected.

The overall quality of the human-chimp libraries was excellent as confirmed by the PGM data with 90% of the assays targets from the 5% chimp dilutions confirmed via PGM to a nearly-identical 4.9% median minor variant frequency. The evidence that the library outliers belong to the same assay targets indicates that these artefacts are due to challenges in assay design rather than the iPLEX+ methodology.

Nucleotide Amount Adjustment

Post round 2 of iPLEX+ feasibility work continued on improving extension rates of iPLEX+ assays in WT samples. Increasing the WT nucleotide concentration in transition-specific fashion resulted in 2.2 decrease of the number of assays that fail due to poor extension in WT. Additionally, the following parameters of the extend reaction were considered in a study where the iPLEX+ panel was interrogated using WT samples, and investigated for their influence on the assay extension rate in WT samples:

- PCR annealing time—increasing the annealing time during extend would allow the polymerase (Thermosequenase) more time to "find" the depleted WT nucleotide.
- Total nucleotide concentration—keeping the same WT nucleotide ratios as in round 2 but allowing for higher total amount would increase WT incorporation rates.
- 300-cycle PCR—increasing the number of cycles from 200 to 300 would yield more product and higher intensity allele peaks.
- Increasing the polymerase amount—increase in the polymerase concentration would increase the amount of product due to faster turnover and result in higher intensity allele peaks.

Figure 6:
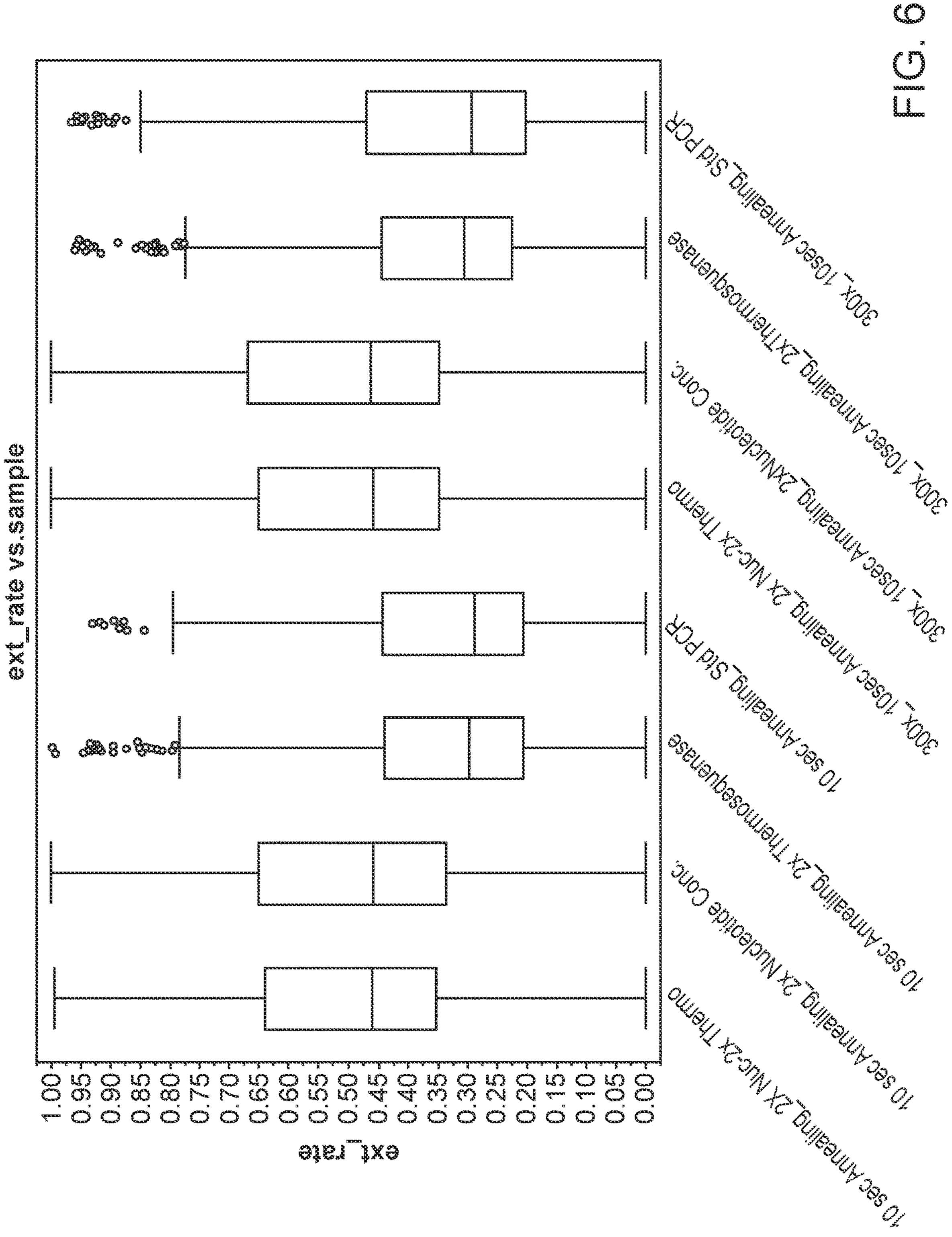
FIG. 6 shows box plots of the assay extension rates (y-axis) for different extend reaction condition (x-axis).

FIG. 6 shows the boxplots of the assay extension rates for each condition as outlined above.

The conditions that yield highest assay extension rates in 0% chimp WT samples are #1, #2, #5 and #6 (left to right on the x-axis). The constant component of these four conditions is 2× nucleotide amount. The 2× nucleotide amount represents two times the total concentration of the nucleotides with the WT transition-specific proportion kept as in round 2.

iPLEX+ Third Round

The third and final round of iPLEX+ feasibility study utilized the transition-specific WT nucleotide concentrations and 2× total nucleotide concentration as previously determined. Similar to the rounds 1 and 2 the round three of iPLEX+ feasibility consisted of the following study. Human/Chimp DNA was pooled into dilution series to represent 0%, 1%, 2.5% and 5% chimp contribution. Each dilution series was interrogated in 16 technical replicates. As the case in round 1 the following criteria were evaluated when determining the method performance:

- assay extension in 0% chimp samples,
- chimp frequency in 0% chimp samples,
- assay sensitivity,
- transition performance and sensitivity,
- overall sensitivity.

Thirty-seven (37) assays failed due to poor extension in 0% chimp WT samples and 33 samples extending chimp non-specifically in WT samples. It is a further improvement compared to the round 2 (44 assays). The resulting fraction of poor assays in round 3 is 23% (compared to 25% in round 2). Also observed was a moderate improvement of the assay extension rates by using 2N total terminator nucleotides. The average assay extension rate in 0% chimp samples is 0.53 and in the 0% and the 5% chimp samples. That's an improvement over the round 2 results (0.41 for the 0% chimp and 0.63 for the 5% chimp samples). As in rounds 1 and 2, the sensitivity of each transition and the overall sensitivity of the panel were determined. Moderate changes at the level of each transition were observed, however, the overall performance of the round 3 panel was again similar to that of the first two rounds with the exception of the 1% chimp sensitivity.

The overall sensitivity of the round 3 panel was 0.35 for the 1% chimp (compared to 0.52 in round 2), 0.89 for the 2.5% chimp (compared to 0.91 in round 2) and 0.99 for the 5% chimp (compared to in round 2). The sensitivity of the round 3 assays for 1% chimp samples decreased from 0.52 to 0.35. Without being limited by theory, two possible explanations for the observed decrease in panel sensitivity toward 1% chimp samples with increase in terminator nucleotide concentration (0.61 round 1, 0.52 round 2 and 0.35 round 3) are as follows:

- Increasing the WT nucleotide percentage and the total nucleotide concentration leads to increase in peak intensity of the major WT allele. This in turn results in the method performing similar to the regular iPLEX where 1% minor allele signals are low intensity noise peaks.
- Increasing the WT nucleotide percentage and the total nucleotide concentration reduced the number of poor extending assays from 96 in round 1 to 44 in round 2 and 37 in round 3. These "recently poor" assays that barely pass the QC in rounds 2 and 3 reduce the 1% chimp sensitivity because they have low signal to noise ratio, but now they are taken into account when the overall sensitivity is calculated.

Example 7—Optimal Nucleotide Concentration

The optimal nucleotide concentration in an iPLEX+ reaction for each possible transition is shown in Table 5. Also shown is the WT/Mut (major allele/minor allele) ratio.

TABLE 5

| Mix | Nucleotide | Concentration in Rxn (mM) | Wt/Mut Ratio |
|---|---|---|---|
| A | A | 0.007 | |
| | C | 2.222 | 0.003 |
| | G | 0.311 | 0.021 |
| | T | 0.889 | 0.008 |
| C | A | 2.222 | 0.006 |
| | C | 0.013 | |
| | G | 0.381 | 0.035 |
| | T | 0.889 | 0.015 |
| G | A | 1.111 | 0.013 |
| | C | 1.111 | 0.013 |
| | G | 0.014 | |
| | T | 1.111 | 0.013 |

TABLE 5-continued

| Mix | Nucleotide | Concentration in Rxn (mM) | Wt/Mut Ratio |
|---|---|---|---|
| T | A | 1.111 | 0.0125 |
| | C | 1.111 | 0.0125 |
| | G | 2.778 | 0.005 |
| | T | 0.0139 | |

Example 8—iPLEX Plus Verification Study

A study was conducted to verify the iPlex Plus assay. The assay was tested for functionality, sensitivity and reproducibility for somatic mutation detection of mutations in NRAS and EGFR genes (models).

Assay Functionality

Experiments used 200 copies/μl of mutant for 5% mutants. All other minor variants were titrated from this starting value. The wild type contribution was 4000 copies/μl.

- Assays were assessed for proper wild type extension using wild type template and standard iPLEX termination mix. Assays that failed to extend the proper wild type nucleotide were evaluated for non-specific interactions and re-designed or moved to another plex if appropriate.
- Assays were assessed for non-specific extension in non-template controls and moved to another plex if appropriate.
- Assays were assessed for proper extension in 5% mutant model using the custom nucleotide mix. All proper variant genotypes were observed.
- Assays were evaluated for exonuclease activity and additional signals.
- Assays were evaluated by peak SNR (signal to noise ratio). During development, three assays showed repeated poor performance in peak SNR. Each assay was inspected for cause. The proposed cause was mitigated with a new design and/or plex re-assignment.

Assay Sensitivity

Initial studies investigated nucleotide ratios necessary to achieve minor variant detection at and below 5% (initial nucleotide mix). Samples were run in triplicate with a WT sample run in triplicate for each plex as well. The initial nucleotide mix did not provide the required sensitivity. High wild type signals cause the mutant ratio to be low, which does not allow for the differentiation from other mutant classes (Data not shown).

To enhance sensitivity toward the mutant allele, the WT nucleotide contribution was reduced. This evaluation used a 5%, 2% and 1% minor variant with WT and NTC samples. Each sample was run in triplicate. Reduction of the wild type successfully increased the mutant ratio to allow greater minor variant discrimination, however the SNR of the WT peaks for several assays fell below cutoffs (SNR of 5) for calling a peak (Data not shown).

WT nucleotide concentrations were increased slightly in an adjusted nucleotide mix to increase the WT SNR. This evaluation utilized the same standards and minor variants as the previous experiment exploring the reduction of WT nucleotide. The WT samples were run in duplicate and one NTC for each plex. Increasing the WT contribution of the mixes to a concentration in between the original mix and the reduced WT mix successfully adjusted many assays with poor WT signal or poor discrimination between variant classes (Data not shown). Evaluating data from all three nucleotide mix trials suggest using custom nucleotide ratios between WT and Mutant.

The custom nucleotide mix was evaluated with the same twelve controls as the previous two experiments in quadruplicates. WT and NTC were also run in quadruplicate per plex. The custom nucleotide ratio mixes successfully give mutant ratios that can be differentiated, while maintaining enough WT SNR to allow a peak to be recognized and called by the software (SNR values greater than 5) (see Table 6). The custom nucleotide mix (Table 6) represents a further refinement of the optimal nucleotide concentration mix of Table 5.

TABLE 6

| Mix | Nucleotide | Concentration in Rxn (mM) | Wt/Mut Ratio |
|---|---|---|---|
| A | A | 0.007 | |
| | C | 2.222 | 0.003 |
| | G | 0.311 | 0.021 |
| | T | 0.889 | 0.008 |
| C | A | 2.222 | 0.006 |
| | C | 0.013 | |
| | G | 0.381 | 0.035 |
| | T | 0.889 | 0.015 |
| G | A | 1.111 | 0.013 |
| | C | 1.111 | 0.013 |
| | G | 0.014 | |
| | T | 1.111 | 0.013 |
| T | A | 1.111 | 0.0003 |
| | C | 1.111 | 0.0003 |
| | G | 2.778 | 0.0001 |
| | T | 0.0003 | |

Reproducibility

Each minor variant model (5%, 2.5%, 1%, and WT's) used in the sensitivity experiments was evaluated in 24 replicates (WT's in 96 replicates). Each model minor variant class produced statistically significant different distributions (Data not shown).

Example 9—Non-Limiting Examples of Embodiments

Provided hereafter are non-limiting examples of certain embodiments of the technology.

A1. A multiplexed method for identifying the presence or absence of one or more minor nucleic acid species in a nucleic acid population comprising a mixture of the one or more minor nucleic acid species and one or more major nucleic acid species, wherein each minor nucleic acid species is a variant of a corresponding major nucleic acid species and is present in a copy number that is less than the copy number of its corresponding major nucleic acid species, the method comprising:

(a) simultaneously amplifying target regions of the mixture with amplification primer pairs under amplification conditions comprising dNTPs, whereby an amplified mixture of nucleic acids comprising major and minor nucleic acid species is produced;

(b) contacting the amplified mixture with extension primers under extension conditions comprising chain terminating reagents, wherein:

(i) the one or more major nucleic acid species share a common chain terminating reagent that is specific for the major nucleic acid species and is not specific for the minor nucleic acid species, and (ii) each of the one or more minor nucleic acid species has a chain terminating reagent that is specific for the minor nucleic acid species and is not specific for the major nucleic acid species, wherein the chain terminating reagent that is specific for the minor nucleic acid species either: (A) is unique for a particular minor nucleic acid species in the amplified mixture and is not shared by the other minor nucleic acid species in the amplified mixture, or (B) at least one of the one or more minor nucleic acid species shares a common chain terminating reagent with at least one other minor nucleic acid species in the amplified mixture, whereby the primers are extended up to, or through, the nucleotide positions that are different in the minor nucleic acid species relative to the major nucleic acid species, thereby generating chain terminated extension products corresponding to the minor nucleic acid species and the major nucleic acid species, respectively, wherein the concentration of the chain terminating reagent specific for the major nucleic acid species is less than the concentration(s) of each of the chain terminating reagent(s) specific for the one or more minor nucleic acid species; and (c) analyzing the extension products of (b), thereby identifying the presence or absence of the one or more minor nucleic acid species.

A2. The method of embodiment A1, wherein the nucleic acid population comprises a plurality of minor nucleic acid species that are variants of a single major nucleic acid species and the plurality of minor nucleic acid species are identified in a single, multiplexed reaction.

A3. The method of embodiment A1, wherein (b) is performed in a set of at least two reaction vessels or compartments, wherein:

a first vessel or compartment comprises extension conditions comprising the chain terminating reagent that is specific for the major nucleic acid species and not comprising a chain terminating reagent that is specific for the one or more minor nucleic acid species; and each of the remaining vessels or compartments comprises extension conditions comprising a single chain terminating reagent specific for and common to one or more minor nucleic acid species and not comprising chain terminating reagents specific for the major nucleic acid species or specific for minor nucleic acid species that do not share the common, single chain terminating reagent.

A4. The method of any of embodiments A1-A3, wherein the concentrations of each of the chain terminating reagents are known.

B1. A method for quantifying one or more minor nucleic acid species in a nucleic acid population comprising a mixture of the one or more minor nucleic acid species and a major nucleic acid species, wherein the minor nucleic acid species are variants of the same major nucleic acid species and are each present in a copy number that is less than the copy number of the major nucleic acid species, the method comprising:

(a) simultaneously amplifying target regions of the mixture with amplification primer pairs under amplification conditions comprising dNTPs, whereby an amplified mixture of nucleic acids comprising major and minor nucleic acid species is produced;

(b) contacting the amplified mixture with extension primers under extension conditions comprising chain terminating reagents specific for (i) each of the one or more minor nucleic acid species, and (ii) the major nucleic acid species, whereby the primers are extended up to, or through, the nucleotide positions that are different in the minor nucleic acid species relative to the major nucleic acid species, thereby generating chain terminated extension products corresponding to the minor nucleic acid species and the major nucleic acid species, respectively, wherein: (1) the concentrations of each of the chain terminating reagents are known; and (2) the concentration of the chain terminating reagent specific for the major nucleic acid species is less than the concentration(s) of the chain terminating reagent(s) specific for the one or more minor nucleic acid species;

(c) determining the ratio of the amount(s) of extension products corresponding to each of the one or more minor nucleic acid species relative to the amount of extension product corresponding to the major nucleic acid species; and (d) based on the ratio of (c), and based on the concentration(s) of the chain terminating reagents specific for the one or more minor nucleic acid species relative to the concentration of the chain terminating reagent specific for the major nucleic acid species, quantifying the amount(s) of minor nucleic acid species relative to the amount of the major nucleic acid species.

C1. A multiplexed method for quantifying one or more minor nucleic acid species in a nucleic acid population comprising a mixture of the one or more minor nucleic acid species and a major nucleic acid species, wherein each minor nucleic acid species is a variant of a corresponding major nucleic acid species and is present in a copy number that is less than the copy number of its corresponding major nucleic acid species, the method comprising:

(a) simultaneously amplifying target regions of the mixture with amplification primer pairs under amplification conditions comprising dNTPs, whereby an amplified mixture of nucleic acids comprising major and minor nucleic acid species is produced;

(b) contacting the amplified mixture with extension primers under extension conditions comprising chain terminating reagents, wherein:

(i) the one or more major nucleic acid species share a common chain terminating reagent that is specific for the major nucleic acid species and is not specific for the minor nucleic acid species, and (ii) each of the one or more minor nucleic acid species has a chain terminating reagent that is specific for the minor nucleic acid species and is not specific for the major nucleic acid species, wherein the chain terminating reagent that is specific for the minor nucleic acid species either: (A) is unique for a particular minor nucleic acid species in the amplified mixture and is not shared by the other minor nucleic acid species in the amplified mixture, or (B) at least one of the one or more minor nucleic acid species shares a common chain terminating reagent with at least one other minor nucleic acid species in the amplified mixture, whereby the primers are extended up to, or through, the nucleotide positions that are different in the minor nucleic acid species relative to the major nucleic acid species, thereby generating chain terminated extension products corresponding to the minor nucleic acid species and the major nucleic acid species, respectively, wherein: (1) the concentrations of each of the chain terminating reagents are known; and (2) the concentration of the chain terminating reagent specific for the major nucleic acid species is less than the concentration(s) of the chain terminating reagent (s) specific for the one or more minor nucleic acid species;

(c) determining the ratio of the amount(s) of extension products corresponding to each of the one or more minor nucleic acid species relative to the amount of extension product corresponding to the major nucleic acid species; and (d) based on the ratio of (c), and based on the concentration(s) of the chain terminating reagents specific for the one or more minor nucleic acid species relative to the concentration of the chain terminating reagent specific for the major nucleic acid species, quantifying the amount(s) of minor nucleic acid species relative to the amount of the major nucleic acid species.

C2. The method of embodiment B1 or embodiment C1, wherein the nucleic acid population comprises a plurality of minor nucleic acid species that are variants of a single major nucleic acid species and the plurality of minor nucleic acid species are identified in a single, multiplexed reaction.

C3. The method of embodiment C1, wherein (b) is performed in a set of at least two reaction vessels or compartments, wherein:

a first vessel or compartment comprises extension conditions comprising the chain terminating reagent that is specific for the major nucleic acid species and not comprising a chain terminating reagent that is specific for the one or more minor nucleic acid species; and each of the remaining vessels or compartments comprises extension conditions comprising a single chain terminating reagent specific for and common to one or more minor nucleic acid species and not comprising chain terminating reagents specific for the major nucleic acid species or specific for minor nucleic acid species that do not share the common, single chain terminating reagent.

D1. The method of any of embodiments A1-A4, B1 and C1-C3, wherein the sequences of the minor and major nucleic acid species differ by a single base and the primers are extended up to, or through, the single base that is different.

D2. The method of any of embodiments A1-A4, B1, C1-C3 and D1, wherein the sequence of the minor nucleic acid species comprises an insertion or a deletion relative to the sequence of the major nucleic acid species.

D3. The method of any of embodiments A1-A4, B1, C1-C3, D1 and D2, wherein the one or more minor nucleic acid species are single nucleotide polymorphism (SNP) variants of the major nucleic acid species.

D4. The method of any of embodiments A1-A4, B1, C1-C3 and D1-D3, wherein the minor and major nucleic acid species are mutant and wild type alleles, respectively, of the same gene.

D5. The method of any of embodiments A1-A4, B1, C1-C3 and D1-D4, wherein the major nucleic acid species is from a host subject and the minor nucleic acid species are from a subject other than the host or the minor nucleic acid species is from a host subject and the major nucleic acid species are from a subject other than the host.

D6. The method of any of embodiments A1-A4, B1, C1-C3 and D1-D5, wherein the one or more minor nucleic acid species are each present in a copy number that is less than about 10% of the copy number of the major nucleic acid species.

D7. The method of embodiment D6, wherein the one or more minor nucleic acid species are each present in a copy number that is between about 1% to less than 10% of the copy number of the major nucleic acid species.

D8. The method of embodiment D7, wherein the one or more minor nucleic acid species are each present in a copy number that is between about 2% to less than 10% of the copy number of the major nucleic acid species.

D9. The method of embodiment D7, wherein the one or more minor nucleic acid species are each present in a copy number that is about 5% or less of the copy number of the major nucleic acid species.

D10. The method of embodiment D7, wherein the one or more minor nucleic acid species are each present in a copy number that is about 2% or less of the copy number of the major nucleic acid species.

D10. 1. The method of embodiment D7, wherein the one or more minor nucleic acid species are each present in a copy number that is about 1% of the copy number of the major nucleic acid species.

D11. The method of any of embodiments A1-A4, B1, C1-C3 and D1-D10.1, wherein the concentration of the chain terminating reagent specific for the major nucleic acid species is between about 1% to about 20% of the concentration of each of the chain terminating reagent(s) specific for the minor nucleic acid species.

D12. The method of any of embodiments A1-A4, B1, C1-C3 and D1-D10.1, wherein the concentration of the chain terminating reagent specific for the major nucleic acid species is between about 0.1% to about 10% of the concentration of each of the chain terminating reagent(s) specific for the minor nucleic acid species.

D13. The method of embodiment D12, wherein the concentration of the chain terminating reagent specific for the major nucleic acid species is between about 0.1% to about 4% of the concentration of each of the chain terminating reagent(s) specific for the minor nucleic acid species.

D13.1. The method of any of embodiments A1-A4, B1, C1-C3 and D1-D10.1, wherein the concentration of the chain terminating reagent specific for the major nucleic acid species is between about 0.01% to about 10% of the concentration of each of the chain terminating reagent(s) specific for the minor nucleic acid species.

D13.2. The method of embodiment D13.1, wherein the concentration of the chain terminating reagent specific for the major nucleic acid species is between about 0.01% to about 4% of the concentration of each of the chain terminating reagent(s) specific for the minor nucleic acid species.

D14. The method of any of embodiments A1-A4, B1, C1-C3 and D1-D13.2, wherein the concentration of the chain terminating reagent for the major nucleic acid species varies based on the specific major species/minor species transition.

D15. The method of any of embodiments A1-A4, B1, C1-C3 and D1-D14, wherein the chain terminating reagents are chain terminating nucleotides.

D16. The method of embodiment D15, wherein the chain terminating nucleotides independently are selected from among ddATP, ddGTP, ddCTP, ddTTP and ddUTP.

D17. The method of embodiment D15 or D16, wherein the chain terminating nucleotides specific for one or more of the minor nucleic acid species consist of one chain terminating nucleotide.

D18. The method of embodiment D15 or D16, wherein the chain terminating nucleotides specific for one or more of the minor nucleic acid species consist of two chain terminating nucleotides.

D19. The method of embodiment D15 or D16, wherein the chain terminating nucleotides specific for one or more of the minor nucleic acid species consist of three chain terminating nucleotides.

D20. The method of any of embodiments A1-A4, B1, C3 and D1-D19, wherein the chain terminating reagents comprise one or more acyclic terminators.

D21. The method of any of embodiments A1-A4, B1, C1-C3 and D1-D20, comprising between about 30 to about 45 PCR amplification cycles in (a).

D22. The method of any of embodiments A1-A4, B1, C1-C3 and D1-D21, wherein the extension conditions in (b) comprise between about 20 to about 300 cycles.

D23. The method of embodiment D22, wherein the extension conditions in (b) comprise at least 50 cycles.

D24. The method of any of embodiments A1-A4, B1, C1-C3 and D1-D23, wherein one or more of the chain terminating reagents comprises a detectable label.

D25. The method of embodiment D24, wherein the label is a fluorescent label or dye.

D26. The method of embodiment D24, wherein the label is a mass label.

D27. The method of any of embodiments D24 to D26, further comprising detection of the label, whereby the one or more minor nucleic acid species are identified or quantified.

D28. The method of embodiment D27, wherein the label is a mass label and detection is by mass spectrometry.

D28.1. The method of embodiment D27, wherein the label is a fluorescent label or dye and detection is by electrophoresis or real time PCR.

D29. The method of any of embodiments A1-A4, B1, C1-C3 and D1-D28.1, wherein the amplification reaction conditions in (a) comprise water, genomic DNA, a buffer, dNTPs, the primer pairs, $MgCl_2$, and a polymerase, wherein the ratio of the concentration of $MgCl_2$ to the concentration of each one of the dNTPs is selected from 0:1, 9:1, 8:1, 7:1, 6:1, or 5:1.

D30. The method of embodiment D29, wherein the polymerase is Taq polymerase at a concentration of at least about 0.03 units/μl.

D31. The method of any of embodiments A1-A4, B1, C1-C3 and D1-D30, wherein the amplification reaction conditions in (a) comprise between about 400-700 μM of each dNTP, about 100 nM primer pairs, and between about 1.6 up to about 4.8 mM $MgCl_2$.

D32. The method of any of embodiments A1-A4, B1, C1-C3 and D1-D31, wherein a sequence tag is attached to one or more primers in the amplification primer pair.

D33. The method of any of embodiments A1-A4, B1, C1-C3 and D1-D32, wherein the free $Mg^{2+}$ concentration is between 1.0-2.0 mM.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Modifications may be made to the foregoing without departing from the basic aspects of the technology. Although the technology has been described in substantial detail with reference to one or more specific embodiments, those of ordinary skill in the art will recognize that changes may be made to the embodiments specifically disclosed in this application, yet these modifications and improvements are within the scope and spirit of the technology.

The technology illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the technology claimed. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" is about 1, about 2 and about 3). For example, a weight of "about 100 grams" can include weights between 90 grams and 110 grams. Thus, it should be understood that although the present technology has been specifically disclosed by representative embodiments and optional features, modification and variation of the concepts herein disclosed may be resorted to by those skilled in the art, and such modifications and variations are considered within the scope of this technology.

Embodiments of the technology are set forth in the claim(s) that follow(s).

What is claimed is:

1. A method for identifying the presence or absence of one or more minor nucleic acid species in a sample, comprising:

(a) obtaining nucleic acids from a sample that includes a target nucleic acid, wherein the target nucleic acid has a major nucleic acid species and one or more minor nucleic acid species wherein each minor nucleic acid species is a lower frequency or copy number variant of the major nucleic acid species and is present at a frequency or copy number that is less than about 10% of the frequency or copy number of the major nucleic acid species, wherein "about" means±10% of the indicated value;

(b) contacting the nucleic acids of (a) with one or more extension primers, each of which comprises an oligonucleotide that hybridizes to the target nucleic acid, under extension conditions comprising a chain terminator specific for the major nucleic acid species and one or more chain terminators specific for the one or more minor nucleic acid species, wherein the concentration of the chain terminator specific for the major nucleic acid species is between 1% to 20%, or 0.5% to less than 20%, or 0.1% to 10%, or 0.01% to 10%, or 0.01% to 5% of the concentration of each of the chain terminator (s) specific for the minor nucleic acid species and wherein, if a ddNTP chain terminator is present in the extension conditions, the same dNTP is absent from the extension conditions, whereby the one or more extension primers are extended by the chain terminators, thereby generating chain terminated extension products corresponding to the minor nucleic acid species and/or chain terminated extension products corresponding to the major nucleic acid species; and (c) analyzing the extension products of (b), thereby identifying the presence or absence of the one or more minor nucleic acid species.

2. The method of claim 1, wherein the nucleic acids of (a) are obtained by amplifying the target nucleic acid in a sample with amplification primer pairs under amplification conditions comprising dNTPs.

3. The method of claim 1, wherein:

the extension conditions comprise a chain terminator specific for each of a plurality of minor nucleic acid species of the same major nucleic acid species;

chain terminated extension products corresponding to each one of the plurality of minor nucleic acid species present in the nucleic acids of (a) are generated in a single reaction; and the presence or absence of each of the plurality of minor nucleic acid species that are all variants of the same major nucleic acid species is identified.

4. The method of claim 1, wherein (b) is performed in a set of at least two reaction vessels or compartments, wherein:

a first vessel or compartment comprises extension conditions comprising the chain terminating reagent that is specific for the major nucleic acid species and not comprising a chain terminator that is specific for the one or more minor nucleic acid species; and each of the remaining vessels or compartments comprises extension conditions: (a) comprising a single chain terminator specific for and common to one or more minor nucleic acid species, and (b) not comprising a chain terminator specific for the major nucleic acid species or a chain terminator specific for minor nucleic acid species that do not share the common, single chain terminator.

5. The method of claim 1, wherein the sequences of the minor nucleic acid species and the major nucleic acid species differ by a single base and the primers are extended up to the single base that is different.

6. The method of claim 1, wherein the sequences of the minor nucleic acid species and the major nucleic acid species differ by a single base and the primers are extended through the single base that is different.

7. The method of claim 1, wherein the one or more minor nucleic acid species are each present in a frequency or copy number that is between 0.25% to less than 10%, or 0.5% to less than 10%, or 1% to less than 10% of the frequency or copy number of the major nucleic acid species.

8. The method of claim 1, wherein the one or more minor nucleic acid species represents less than 30%, 20%, 15%, 10%, 8%, 5%, 4%, 3%, 2%, 1%, 0.8%, 0.75%, 0.5%, 0.1%, 0.05%, or 0.01% of the total nucleic acid.

9. The method of claim 1, wherein the chain terminators are chain terminating nucleotides.

10. The method of claim 9, wherein the chain terminating nucleotides independently are selected from among ddATP, ddGTP, ddCTP, ddTTP and ddUTP.

11. The method of claim 9, wherein the chain terminating nucleotides specific for one or more of the minor nucleic acid species consist of one chain terminating nucleotide, two chain terminating nucleotides or three chain terminating nucleotides.

12. The method of claim 9, wherein the chain terminators further comprise one or more acyclic terminators.

13. The method of claim 1, wherein one or more chain terminators comprise a mass label, and the one or more minor nucleic acid species are identified by detection of the mass label.

14. The method of claim 13, wherein detection of the label is by mass spectrometry.

15. The method of claim 1, further comprising quantifying the one or more minor nucleic acid species by:

(1) detecting a detection signal corresponding to each of the extension products of the one or more minor nucleic acid species and a detection signal corresponding to the extension products of the major nucleic acid species, thereby determining the ratio of the amount(s) of extension products corresponding to each of the one or more minor nucleic acid species relative to the amount of extension product corresponding to the major nucleic acid species based on the proportion of the detection signal corresponding to each of the extension products of the one or more minor nucleic acid species relative to the detection signal corresponding to the extension products of the major nucleic acid species; and (2) based on the ratio as determined in (1), and based on the concentration(s) of the chain terminators specific for the one or more minor nucleic acid species relative to the concentration of the chain terminator specific for the major nucleic acid species, quantifying the amount (s) of minor nucleic acid species relative to the amount of the major nucleic acid species using a normalization coefficient.

16. The method of claim 15, wherein the normalization coefficient is inversely proportional to the ratio of the concentration of the chain terminator specific for the major nucleic acid species compared to the concentration of the chain terminator(s) specific for the minor nucleic acid species.

17. The method of claim 15, wherein detecting the detection signal is by mass spectrometry and wherein the ratio of the amount(s) of extension products corresponding to each of the one or more minor nucleic acid species relative to the amount of extension product corresponding to the major nucleic acid species is determined as the ratio of the signal for the minor nucleic acid species generated by mass spectrometry analysis to the signal for the major nucleic acid species generated by mass spectrometry analysis.

18. The method of claim 1, wherein the sequence of the minor nucleic acid species comprises an insertion or a deletion relative to the sequence of the major nucleic acid species, or the minor nucleic acid species is a single nucleotide polymorphism (SNP) variant of the major nucleic acid species.

19. The method of claim 1, wherein the minor and major nucleic acid species are mutant and wild type alleles, respectively, of the same gene.

20. A kit for analyzing a target nucleic acid, comprising:

one or more extension primers;

a chain terminating nucleotide specific for a major nucleic acid species of the target nucleic acid;

at least one chain terminating nucleotide specific for a minor nucleic acid species of the target nucleic acid, wherein the relative amounts of the chain terminating nucleotide specific for the major nucleic acid species and the chain terminating nucleotide specific for the minor nucleic acid species are present in solution such that the concentration of the chain terminating nucleotide specific for the major nucleic acid species is between 0.5% to less than 20% of the concentration of the chain terminating nucleotide(s) specific for the minor nucleic acid species; and instructions for performing the method of claim 9.

21. The kit of claim 20, wherein the concentration of the chain terminating nucleotide specific for the major nucleic acid species is between 1% to 10% of the concentration of the chain terminating nucleotide(s) specific for the minor nucleic acid species.

* * * * *